United States Patent [19]

Tominaga et al.

[11] 4,415,572
[45] Nov. 15, 1983

[54] PIPERAZINYLCARBOSTYRIL COMPOUNDS

[75] Inventors: Michiaki Tominaga; Yung h. Yang; Hidenori Ogawa; Kazuyuki Nakagawa, all of Tokushima, Japan

[73] Assignee: Otsuka Pharmaceutical Co., Ltd., Tokyo, Japan

[21] Appl. No.: 316,572

[22] Filed: Oct. 30, 1981

[30] Foreign Application Priority Data

Oct. 31, 1980 [JP] Japan .................. 55-154071

[51] Int. Cl.³ .................. C07D 401/00; A61K 31/495
[52] U.S. Cl. .................. 424/250; 544/360; 544/363; 546/157; 546/158
[58] Field of Search .................. 544/360, 363; 424/250

[56] References Cited

FOREIGN PATENT DOCUMENTS

| | | | |
|---|---|---|---|
| 54-130589 | 10/1979 | Japan | 544/238 |
| 54-135785 | 10/1979 | Japan | 544/238 |
| 54-138585 | 11/1979 | Japan | 238/ |
| 54-141785 | 11/1979 | Japan | 544/238 |
| 55-35284 | 4/1980 | Japan | 544/238 |
| 55-49319 | 4/1980 | Japan | 544/238 |
| 55-53283 | 4/1980 | Japan | 544/238 |
| 55-76872 | 6/1980 | Japan | 544/238 |
| 55-83781 | 6/1980 | Japan | 544/238 |

OTHER PUBLICATIONS

Endoh, M., et al, Tohoku J. Exp. Med., (1972), 106, pp. 165-173.
Endoh, M., British J. Pharmac., (1975), 55, pp. 475-486.
Gray's Anatomy, 35th Ed., 1973 Longman Group Ltd.
The Merck Index, 9th Ed., (1976), pp. 3422 & 6504, Merck & Co., Inc.

Primary Examiner—Donald G. Daus
Assistant Examiner—S. A. Gibson
Attorney, Agent, or Firm—Sughrue, Mion, Zinn, Macpeak, and Seas

[57] ABSTRACT

A piperazinylcarbostyril compound of the formula (I)

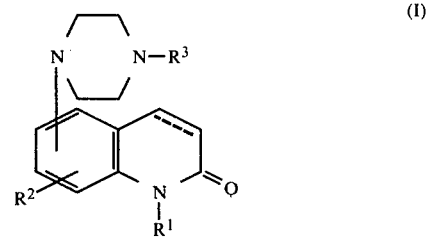

wherein
$R^1$ represents a hydrogen atom, a lower alkyl group, a lower alkenyl group, a lower alkynyl group, or a phenyl-lower alkyl group;
$R^2$ represents a hydrogen atom or a lower alkoxy group;
$R^3$ represents a hydrogen atom, a lower alkanoyl group, a furoyl group, a pyridylcarbonyl group, a lower alkanesulfonyl group, a lower alkoxycarbonyl group, a lower alkoxycarbonyl-lower alkyl group, a phenylsulfonyl group which may be substituted with a lower alkyl group on the benzene ring thereof, a lower alkyl group, a lower alkenyl group, a lower alkynyl group, a phenylcarbonyl group, a phenyl-lower alkyl group or a phenyl-lower alkanoyl group where each of said phenylcarbonyl group, phenyl-lower alkyl group and phenyl-lower alkanoyl group may be substituted with 1 to 3 of a lower alkoxy group, a halogen atom, a lower alkyl group, a cyano group, a nitro group, an amino group, a hydroxy group, a lower alkanoylamino group, a lower alkylthio group and a lower alkanoyloxy group, or with a lower alkylenedioxy group on the benzene ring thereof; and
the bonding between the 3- and 4-positions of the carbostyril nucleus is a single bond or a double bond; or its pharmaceutically acceptable salt, useful as a cardiotonic agent.

27 Claims, No Drawings

PIPERAZINYLCARBOSTYRIL COMPOUNDS

BACKGROUND OF THE INVENTION

This invention relates to certain carbostyril compounds and to pharmaceutically acceptable salts thereof which are useful as cardiotonic agents, processes for preparing the same, and pharmaceutical compositions containing the carbostyril compounds or salt thereof.

Various carbostyril compounds are known which have hypotensive, blood platelet coagulation inhibitory or antiallergic activity as described in Japanese Patent Application (OPI) Nos. 130589/79, 135785/79, 138585/79, 141785/79, 76872/80, 49319/80, 53283/80, 53284/80 and 83781/80 (the term "OPI" as used herein refers to a "published unexamined Japanese patent applicaton").

Further, EP-A1-7525 and EP-A1-8014 describe isoquinoline compounds which have cardiac and circulatory activities.

However, the carbostyril compounds of this invention are structurally different from the conventional carbostyril and isoquinoline compounds.

SUMMARY OF THE INVENTION

One object of this invention is to provide carbostyril compounds having a cardiotonic activity.

Another object of this invention is to provide a pharmaceutical composition containing the carbostyril compound in a cardiotonically effective amount.

A further object of this invention is to provide a process for preparing a carbostyril compound and its pharmaceutically acceptable salts thereof.

As a result of extensive research this invention has been accomplished which, in one aspect, provides a carbostyril compound of the formula (I).

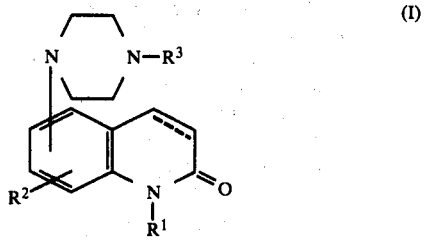

wherein
$R^1$ represents a hydrogen atom, a lower alkyl group, a lower alkenyl group, a lower alkynyl group, or a phenyl-lower alkyl group;
$R^2$ represents a hydrogen atom or a lower alkoxy group;
$R^3$ represents a hydrogen atom, a lower alkanoyl group, a furoyl group, pyridylcarbonyl group, a lower alkanesulfonyl group, a lower alkoxycarbonyl group, a lower alkoxycarbonyl-lower alkyl group, a phenylsulfonyl group which may be substituted with a lower alkyl group on the benzene ring thereof, a lower alkyl group, a lower alkenyl group, a lower alkynyl group, a phenylcarbonyl group, a phenyl-lower alkyl group, or a phenyl-lower alkanoyl group, where each of said phenylcarbonyl group, phenyl-lower alkyl group and phenyl-lower alkanoyl group may be substituted with 1 to 3 of a lower alkoxy group, a halogen atom, a lower alkyl group, a cyano group, a nitro group, an amino group, a hydroxy group, a lower alkanoylamino group, a lower alkylthio group and a lower alkanoyloxy group, or with a lower alkylenedioxy group on the benzene ring thereof; and the bonding between the 3 and 4 positions of the carbostyril nucleus is a single bond or a double bond, and the pharmaceutically acceptable salts thereof.

In another aspect, this invention provides a cardiotonic composition containing a compound of the formula (I) or a pharmaceutically acceptable salt thereof in a cardiotonically effective amount.

In a further aspect, this invention provides processes for preparing the compounds of the formula (I) and pharmaceutically acceptable salts thereof.

The compounds of the formula (I) above and pharmaceutically acceptable salts thereof have heart muscle contraction stimulating effect or positive inotropic effect and coronary blood flow increasing activity, and are useful as a cardiotonic agent for treating heart diseases such as congestive heart failure and the like. They are advantageous in that they do not or only slightly, if any, increase heart beats.

DETAILED DESCRIPTION OF THE INVENTION

The term "lower alkyl" as used herein refers to a straight or branched chain alkyl group having 1 to 6 carbon atoms such as a methyl group, an ethyl group, a propyl group, an isopropyl group, a butyl group, a tert-butyl group, a pentyl group, a hexyl group and the like.

The term "lower alkenyl" as used herein refers to a straight or branched chain alkenyl group having 2 to 6 carbon atoms, such as a vinyl group, an allyl group, a 2-butenyl group, a 3-butenyl group, a 1-methyallyl group, a 2-pentenyl group, a 2-hexenyl group and the like.

The term "lower alkynyl" as used herein refers to a straight or branched chain alkynyl group having 2 to 6 carbon atoms such as an ethynyl group, a 2-propynyl group, a 2-butynyl group, a 3-butynyl group, a 1-methyl-2-propynyl group, a 2-pentynyl group, a 2-hexynyl group and the like.

The term "phenyl-lower alkyl" as used herein refers to a phenyl-lower alkyl group having a straight or branched chain alkyl group having 1 to 6 carbon atoms in the alkyl moiety such as a benzyl group, a 2-phenylethyl group, a 1-phenylethyl group, a 3-phenylpropyl group, a 4-phenylbutyl group, a 1,1-dimethyl-2-phenylethyl group, a 5-phenylpentyl group, a 6-phenylhexyl group, a 2-methyl-3-phenylpropyl group and the like.

The term "lower alkoxy" as used herein refers to a straight or branched chain alkoxy group having 1 to 6 carbon atoms such as a methoxy group, an ethoxy group, a propoxy group, an isopropoxy group, a butoxy group, a tert-butoxy group, a pentyloxy group, a hexyloxy group and the like.

The term "lower alkanoyl" as used herein refers to a straight or branched chain alkanoyl group having 1 to 6 carbon atoms such as a formyl group, an acetyl group, a propionyl group, a butyryl group, an isobutyryl group, a pentanoyl group, a tert-butylcarbonyl group, a hexanoyl group and the like.

The term "halogen" as used herein refers to fluorine, chlorine, bromine and iodine.

The term "lower alkylenedioxy" as used herein refers to a straight or branched chain alkylenedioxy group having 1 to 4 carbon atoms such as a methylenedioxy group, an ethylenedioxy group, a trimethylenedioxy group and the like.

The term "lower alkanesulfonyl" as used herein refers to a straight or branched chain alkanesulfonyl group having 1 to 6 carbon atoms such as methanesulfonyl group, an ethanesulfonyl group, a propanesulfonyl group, an isopropanesulfonyl group, a butanesulfonyl group, a tert-butanesulfonyl group, a pentanesulfonyl group, a hexanesulfonyl group and the like.

The term "lower alkoxycarbonyl" as used herein refers to a straight or branched chain alkoxycarbonyl group having 1 to 6 carbon atoms in the alkoxy moiety such as a methoxycarbonyl group, an ethoxycarbonyl group, a propoxycarbonyl group, an isopropoxycarbonyl group, a butoxycarbonyl group, a tert-butoxycarbonyl group, a pentyloxycarbonyl group, a hexyloxycarbonyl group and the like.

The term "lower alkoxycarbonyl-lower alkyl" as used herein refers to a straight or branched chain lower alkoxycarbonyl-lower alkyl group having 1 to 6 carbon atoms in the alkoxy moiety and 1 to 6 carbon atoms in the alkyl moiety such as a methoxycarbonylmethyl group, a 3-methoxycarbonylpropyl group, a 4-ethoxycarbonylbutyl group, a 6-propoxycarbonylhexyl group, a 5-isopropoxycarbonylpentyl group, a 1,1-dimethyl-2-butoxycarbonylethyl group, a 2-methyl-3-tert-butoxycarbonylpropyl group, a 2-pentyloxycarbonylethyl group, a hexyloxycarbonylmethyl group and the like.

The term "phenylsulfonyl group which may be substituted with a lower alkyl group on the benzene ring" as used herein refers to phenylsulfonyl group which may be substituted with a straight or branched chain alkyl group having 1 to 6 carbon atoms on the benzene ring such as a phenylsulfonyl group, a p-toluenesulfonyl group, a 2-methylphenylsulfonyl group, a 3-ethylphenylsulfonyl group, a 4-propylphenylsulfonyl group, a 2-butylphenylsulfonyl group, a 3-tert-butylphenylsulfonyl group, a 4-pentylphenysulfonyl group, a 2-hexylphenylsulfonyl group and the like.

The term "phenylcarbonyl group substituted with 1 to 3 of a lower alkoxy group, a halogen atom, a lower alkyl group, a cyano group, a nitro group, an amino group, a hydroxy group, a lower alkanoylamino group, a lower alkylthio group and a lower alkanoyloxy group or with a lower alkylenedioxy group" refers to a phenylcarbonyl group substituted with 1 to 3 of a straight or branched chain alkoxy group having 1 to 6 carbon atoms, a halogen atom, a straight or branched chain alkyl group having 1 to 6 carbon atoms, a cyano group, a nitro group, an amino group, a hydroxy group, a straight or branched chain alkanoylamino group having 1 to 6 carbon atoms, a straight or branched chain alkylthio group having 1 to 6 carbon atoms and a straight or branched chain alkanoyloxy group having 1 to 6 carbon atoms, or with an alkylenedioxy group having 1 to 4 carbon atoms such as a 2-chlorobenzoyl group, a 3-chlorobenzoyl group, a 4-chlorobenzoyl group, a 2-fluorobenzoyl group, a 3-fluorobenzoyl group, a 4-fluorobenzoyl group, a 2-bromobenzoyl group, a 3-bromobenzoyl group, a 4-bromobenzoyl group, a 2-iodobenzoyl group, a 4-iodobenzoyl group, a 3,5-dichlorobenzoyl group, a 2,6-dichlorobenzoyl group, a 3,4-dichlorobenzoyl group, a 3,4-difluorobenzoyl group, a 3,5-dibromobenzoyl group, a 3,4,5-trichlorobenzoyl group, a 2-methylbenzoyl group, a 3-methylbenzoyl group, a 4-methylbenzoyl group, a 2-ethylbenzoyl group, a 3-ethylbenzoyl group, a 4-ethylbenzoyl group, a 3-isopropylbenzoyl group, a 4-hexylbenzoyl group, a 3,4-dimethylbenzoyl group, a 2,5-dimethylbenzoyl group, a 3,4,5-trimethylbenzoyl group, a 2-methoxybenzoyl group, a 3-methoxybenzoyl group, a 4-methoxybenzoyl group, a 2-ethoxybenzoyl group, a 3-ethoxybenzoyl group, a 4-ethoxybenzoyl group, a 4-isopropoxybenzoyl group, a 4-hexyloxybenzoyl group, a 3,4-dimethoxybenzoyl group, a 3,4-diethoxybenzoyl group, a 3,4,5-trimethoxybenzoyl group, a 2,5-dimethoxybenzoyl group, a 2-nitrobenzoyl group, a 3-nitrobenzoyl group, a 4-nitrobenzoyl group, a 2,4-dinitrobenzoyl group, a 2-aminobenzoyl group, a 3-aminobenzoyl group, a 4-aminobenzoyl group, a 2,4-diaminobenzoyl group, a 2-cyanobenzoyl group, a 3-cyanobenzoyl group, a 4-cyanobenzoyl group, a 2,4-dicyanobenzoyl group, a 3,4-methylenedioxybenzoyl group, a 3,4-ethylenedioxybenzoyl group, a 2,3-methylenedioxybenzoyl group, a 3-methyl-4-chlorobenzoyl group, a 2-chloro-6-methylbenzoyl group, a 2-methoxy-3-chlorobenzoyl group, a 2-hydroxybenzoyl group, a 3-hydroxybenzoyl group, a 4-hydroxybenzoyl group, a 3,4-dihydroxybenzoyl group, a 3,4,5-trihydroxybenzoyl group, a 2-formylaminobenzoyl group, a 3-acetylaminobenzoyl group, a 4-acetylaminobenzoyl group, a 2-acetylaminobenzoyl group, a 3-propionylaminobenzoyl group, a 4-butyrylaminobenzoyl group, a 2-isobutyrylaminobenzoyl group, a 3-pentanoylaminobenzoyl group, a 3-tert-butylcarbonylamino group, a 4-hexanoylaminobenzoyl group, a 2,6-diacetylaminobenzoyl group, a 2-methylthiobenzoyl group, a 3-methylthiobenzoyl group, a 4-methylthiobenzoyl group, a 2-ethylthiobenzoyl group, a 3-ethylthiobenzoyl group, a 3-isopropylthiobenzoyl group, a 4-hexylthiobenzoyl group, a 3,4-dimethylthiobenzoyl group, a 2,5-dimethylthiobenzoyl group, a 3,4,5-trimethylthiobenzoyl group, a 2-formyloxybenzoyl group, a 3-acetyloxybenzoyl group, a 4-acetyloxybenzoyl group, a 2-acetyloxybenzoyl group, a 3-propionyloxybenzoyl group, a 4-butyryloxybenzoyl group, a 2-isobutyryloxybenzoyl group, a 3-pentanoyloxybenzoyl group, a 3-tert-butyryloxybenzoyl group, a 4-hexanoyloxybenzoyl group, a 3,4-diacetyloxybenzoyl group, a 3,4,5-triacetyloxybenzoyl group and the like.

The term "phenyl-lower alkyl group subsituted with 1 to 3 of a lower alkoxy group, a halogen atom, a lower alkyl group, a cyano group, a nitro group, an amino group, a hydroxy group, a lower alkanoylamino group, a lower alkylthio group and a lower alkanoyloxy group or with a lower alkylenedioxy group" refers to a phenyl-lower alkyl group subsituted with 1 to 3 of a straight or branched chain alkoxy group having 1 to 6 carbon atoms, a halogen atom, a straight or branched chain alkyl group having 1 to 6 carbon atoms, a cyano group, a nitro group, an amino group, a hydroxy group, a straight or branched chain alkanoylamino group having 1 to 6 carbon atoms, a straight or branched chain alkylthio group having 1 to 6 carbon atoms and a straight or branched chain alkanoyloxy group having 1 to 6 carbon atoms, or with an alkylenedioxy group having 1 to 4 carbon atoms such as a 2-chlorobenzyl group, a 2-(3-chlorophenyl)ethyl group, a 1-(4-chlorophenyl)ethyl group, a 3-(2-cluorophenyl)propyl group, a 4-(3-fluorophenyl)butyl group, a 1,1-dimethyl-2-(4-fluorophenyl)ethyl group, a 5-(2-bromophenyl)pentyl group, a 6-(3-bromophenyl)hexyl group, a 2-methyl-3-(4-bromophenyl)propyl group, a 3-iodobenzyl group, a 2-(4-iodophenyl)ethyl group, a 1-(3,5-dichlorophenyl)ethyl group, a 2-(3,4-dichlorophenyl)ethyl group, a 3-(2,6-dichlorophenyl)propyl group, a 4-(3,4-dichlorophenyl)butyl group, a 1,1-dimethyl-2-(3,4-difluorophenyl)ethyl group, a 5-(3,5-dibromophenyl)pentyl group, a 6-(3,4,5-trichlorophenyl)hexyl group, a 4-methylbenzyl group, a 2-(2-methylphenyl)ethyl group, a 1-(3-methylphenyl)ethyl group, a 3-(3-ethylphenyl)propyl group, a 4-(2-ethylphenyl)butyl group, a 5-(4-ethylphenyl)pentyl group, a 6-(3-iospropylphenyl)hexyl group, a 2-methyl-3-(4-hexylphenyl)propyl group, a 2-(3,4-dimethylphenyl)ethyl group, a 2-(2,5-dimethylphenyl)ethyl group, a 2-(3,4,5-trimethylphenyl)ethyl group, a 4-methoxybenzyl group, a 3,4-dimethoxybenzyl group, a 3,4,5-trimethoxybenzyl group, a 1-(3-methoxyphenyl)ethyl group, a 2-(2-methoxyphenyl)ethyl group, a 3-(2-ethoxyphenyl)propyl group, a 4-(4-ethoxyphenyl)butyl group, a 5-(3-ethoxyphenyl)pentyl group, a 6-(4-isopropoxyphenyl)hexyl group, a 1,1-dimethyl-2-(4-hexyloxyphenyl)ethyl group, a 2-methyl-3-(3,4-dimethoxyphenyl)propyl group, a 2-(3,4-dimethoxyphenyl)ethyl group, a 2-(3,4-diethoxyphenyl)ethyl group, a 2-(-b 3,4,5-trimethoxyphenyl)ethyl group, a 1-(2,5-dimethoxyphenyl)ethyl group, a 3-nitrobenzyl group, a 1-(2-nitrophenyl)ethyl group, a 2-(4-nitrophenyl)ethyl group, a 3-(2,4- dinitrophenyl)propyl group, a 4-(2-aminophenyl)butyl group, a 5-(3-aminophenyl)pentyl group, a 6-(4-aminophenyl)hexyl group, a 2,4-diaminobenzyl group, a 2-cyanobenzyl group, a 1,1-dimethyl-2-(3-cyanophenyl)ethyl group, a 2-methyl-3-(4-cyanophenyl)propyl group, a 2,4-dicyanobenzyl group, a 3,4-methylenedioxybenzyl group, a 3,4-ethylenedioxybenzyl group, a 2,3-methylenedioxybenzyl group, a 2-(3,4-methylenedioxyphenyl)ethyl group, a 1-(3,4-ethylenedioxyphenyl)ethyl group, a 3-methyl-4-chlorobenzyl group, a 2-chloro-6-methylbenzyl group, a 2-methoxy-3-chlorobenzyl group, a 2-hydroxybenzyl group, a 2-(3,4-dihydroxyphenyl)ethyl group, a 1-(3,4-dihydroxyphenyl)ethyl group, a 2-(3-hydroxyphenyl)ethyl group, a 3-(4-hydroxyphenyl)propyl group, a 6-(3,4-dihydroxyphenyl)hexyl group, a 3,4-dihydroxybenzyl group, a 3,4,5-trihydroxybenzyl group, a 2-formylaminobenzyl group, a 3-acetylaminobenzyl group, a 3-(2-acetylaminophenyl)propyl group, a 4-(4-acetylaminophenyl)butyl group, a 2-propionylaminobenzyl group, a 3-(3-butyrylaminophenyl)propyl group, a 4-(4-isobutyrylaminophenyl)butyl group, a 5-(2-tert-butylcarbonylaminophenyl)pentyl group, a 6-(3-pentanoylaminophenyl)hexyl group, a (2,4-diacetylamino)benzyl group, a 4-methylthiobenzyl group, a 2-(2-methylthiophenyl)ethyl group, a 1-(3-methylthiophenyl)ethyl group, a 3-(3-ethylthiophenyl)propyl group, a 4-(2-ethylthiophenyl)butyl group, a 5-(4-ethylthiophenyl)pentyl group, a 6-(3-isopropylthiophenyl)hexyl group, a 2-methyl-3-(4-hexylthiophenyl)propyl group, a 2-(3,4-dimethylthiophenyl)ethyl group, a 2-(2,5-dimethylthiophenyl)ethyl group, a 2-(3,4,5-trimethylthiophenyl)ethyl group, a 4-acetyloxybenzyl group, a 3,4-acetyloxybenzyl group, a 3,4,5-triacetyloxybenzyl group, a 1-(3-acetyloxyphenyl)ethyl group, a 2-(2-acetyloxyphenyl)ethyl group, a 3-(2-propionyloxyphenyl)propyl group, a 4-(4-pentanoyloxyphenyl)butyl group, a 5-(3-propionyloxyphenyl)pentyl group, a 6-(4-isobutyryloxyphenyl)hexyl group, a 1,1-dimethyl-2-(4-hexanoyloxyphenyl)ethyl group, a 4-butyryloxybenzyl group and the like.

The term "lower alkanoylamino" as used herein refers to a straight or branched chain alkanoylamino group having 1 to 6 carbon atoms such as a formylamino group, an acetylamino group, a propionylamino group, a butyrylamino group, an isobutyrylamino group, a pentanoylamino group, a tert-butylcarbonylamino group, a hexanoylamino group and the like.

The term "lower alkylthio" as used herein refers to a straight or branched chain alkylthio group having 1 to 6 carbon atoms such as methylthio group, an ethylthio group, a propylthio group, an isopropylthio group, a butylthio group, a tert-butylthio group, a pentylthio group, a hexylthio group and the like.

The term "lower alkanoyloxy" as used herein refers to a straight or branched chain alkanoyloxy group having 1 to 6 carbon atoms such as a formyloxy group, an acetyloxy group, a propionyloxy group, a butyryloxy group, an isobutyryloxy group, a pentanoyloxy group, a tert-butylcarbonyloxy group, a hexanoyloxy group and the like.

The term "phenyl-lower alkanoyl" as used herein refers to a phenylalkanoyl group having a straight or branched chain alkanoyl group having 1 to 6 carbon atoms in the alkanoyl moiety such as a 2-phenylacetyl group, a 3-phenylpropionyl group, a 4-phenylbutyryl group, a 2-phenylbutyryl group, a 6-pehnylhexanoyl group, a 2-phenylpropionyl group, a 3-phenylbutyryl group, a 4-phenyl-3-methylbutyryl group, a 5-phenylpentanoyl group, a 2-methyl-3-phenylpropionyl group, and the like.

The term "phenyl-lower alkanoyl group substituted with 1 to 3 of a lower alkoxy group, a halogen atom, a lower alkyl group, a cyano group, a nitro group, an amino group, a hydroxy group, a lower alkanoylamino group, a lower alkylthio group and a lower alkanoyloxy group or with a lower alkylenedioxy group" refers to a phenyl-lower alkyl group substituted with 1 to 3 of a straight or branched chain alkoxy group having 1 to 6 carbon atoms, a halogen atom, a straight or branched chain alkyl group having 1 to 6 carbon atoms, a cyano group, a nitro group, an amino group, a hydroxy group, a straight or branched chain alkanoylamino group having 1 to 6 carbon atoms, a straight or branched chain alkylthio group having 1 to 6 carbon atoms and a straight or branched chain alkanoyloxy group having 1 to 6 carbon atoms, or with a straight or branched chain alkylenedioxy group having 1 to 4 carbon atoms such as a 2-(2-chlorophenyl)acetyl group, a 2-(3-chlorophenyl)acetyl group, a 2-(4-chlorophenyl)acetyl group, a 3-(2-fluorophenyl)propionyl group, a 4-(3-fluorophenyl)butyryl group, a 2-(4-fluorophenyl)acetyl group, a 5-(2-bromophenyl)pentanoyl group, a 6-(3-bromophenyl)hexanoyl group, a 2-methyl-3-(4-bromophenyl)propionyl group, a 2-(3-iodophenyl)acetyl group, a 2-(4-iodophenyl)acetyl group, a 2-(3,5-dichlorophenyl)acetyl group, a 2-(3,4-dichlorophenyl)acetyl group, a 3-(2,6-dichlorophenyl)propionyl group, a 4-(3,4-dichlorophenyl)butyryl group, a 2-(3,4-difluorophenyl)acetyl group, a 5-(3,5-dibromophenyl)pentanoyl group, a 6-(3,4,5-trichlorophenyl)hexanoyl group, a 2-(4-methylphenyl)acetyl group, a 2-(2-methylphenyl)acetyl group, a 2-(3-methylphenyl)acetyl group, a 3-(3-ethylphenyl)propionyl group, a 4-(2-ethylphenyl)butyryl group, a 5-(4-ethylphenyl)pentanoyl group, a 6-(3-isopropylphenyl)hexanoyl group, a 2-methyl-3-(4-hexylphenyl)propionyl group, a 2-(3,4-dimethylphenyl)acetyl group, a 2-(2,5-dimethylphenyl)acetyl group, a 2-(3,4,5-trimethylphenyl)acetyl group, a 2-(4-methoxyphenyl)acetyl group, a 2-(3,4-dimethoxyphenyl)acetyl group, a 2-(3,4,5-trimethoxyphenyl)acetyl group, a 2-(3-methoxyphenyl)acetyl group, a 2-(2-methoxyphenyl)acetyl group, a 3-(2-ethoxyphenyl)propionyl group, a 4-(4-ethoxyphenyl)butyryl group, a 5-(3-ethoxyphenyl)pentanoyl group, a 6-(4-isopropoxyphenyl)hexanoyl group, a 2-(4-hexyloxyphenyl)acetyl group, a 2-methyl-3-(3,4-dimethoxyphenyl)propionyl group, a 2-(3,4-dimethoxyphenyl)acetyl group, a 2-(3,4-diethoxyphenyl)acetyl group, a 2-(3,4,5-trimethoxyphenyl)acetyl group, a 2-(2,5-dimethoxyphenyl)acetyl group, a 2-(3-nitrophenyl)acetyl group, a 2-(2-nitrophenyl)acetyl group, a 2-(4-nitrophenyl)acetyl group, a 3-(2,4-dinitrophenyl)propionyl group, a 4-(2-aminophenyl)butyryl group, a 5-(3-aminophenyl)pentanoyl group, a 6-(4-aminophenyl)hexanoyl group, a 2-(2,4-diaminophenyl)acetyl group, a 2-(2-cyanophenyl)acetyl group, a 2-(3-cyanophenyl)acetyl group, a 2-methyl-3-(4-cyanophenyl)propionyl group, a 2-(2,4-dicyanophenyl)acetyl group, a 2-(3,4-methylenedioxyphenyl)acetyl group, a 2-(3,4-ethylenedioxyphenyl)acetyl group, a 2-(2,3-methylenedioxyphenyl)acetyl group, a 2-(3,4-methylenedioxyphenyl)acetyl group, a 2-(3,4-ethylenedioxyphenyl)acetyl group, a 2-(3-methyl-4-chlorophenyl)acetyl group, a 2-(2-chloro-6-methylphenyl)acetyl group, a 2-(2-methoxy-3-chlorophenyl)acetyl group, a 2-(2-hydroxyphenylacetyl group, a 2-(2,4-dihydroxyphenyl)acetyl group, a 2-(3-hydroxyphenyl)acetyl group, a 3-(4-hydroxyphenyl)propionyl group, a 6-(3,4-dihydroxyphenyl)hexanoyl group, a 2-(3,4-dihydroxyphenyl)acetyl group, a 2-(3,4,5-trihydroxyphenyl)acetyl group, a 2-(2-formylaminophenyl)acetyl group, a 2-(3-acetylaminophenyl)acetyl group, a 3-(2-acetylaminophenyl)propionyl group, a 4-(4-acetylaminophenyl)butyryl group, a 2-(2-propionylaminophenyl)acetyl group, a 3-(3-butyrylaminophenyl)propionyl group, a 4-(4-isobutyrylaminophenyl)butyryl group, a 5-(2-tert-butylcarbonylaminophenyl)pentanoyl group, a 6-(3-pentanoylaminophenyl)hexanoyl group, a 2-(2,4-diacetylaminophenyl)acetyl group, a 2-(4-methylthiophenyl)acetyl group, a 2-(2-methylthiophenyl)acetyl group, a 2-(3-methylthiophenyl)acetyl group, a 3-(3-ethylthiophenyl)propionyl group, a 4-(2-ethylthiophenyl)butyryl group, a 5-(4-ethylthiophenyl)pentanoyl group, a 6-(3-isopropylthiophenyl)hexanoyl group, a 2-methyl-3-(4-hexylthiophenyl)propionyl group, a 2-(3,4-dimethylthiophenyl)acetyl group, a 2-(2,5-dimethylthiophenyl)acetyl group, a 2-(3,4,5-trimethoxyphenyl)acetyl group, a 2-(4-acetyloxyphenyl)acetyl group, a 2-(3,4-acetyloxyphenyl)acetyl group, a 2-(3,4,5-triacetyloxyphenyl)acetyl group, a 2-(3-acetyloxyphenyl)acetyl group, a 2-(2-acetyloxyphenyl)acetyl group, a 3-(2-propionyloxyphenyl)propionyl group, a 4-(4-pentanoyloxyphenyl)butyryl group, a 5-(3-propionyloxyphenyl)pentanoyl group, a 6-(4-isobutyryloxyphenyl)hexanoyl group, a 2-(4-hexanoyloxyphenyl)acetyl group, a 2-(4-butyryloxyphenyl)acetyl group, and the like.

The compounds of this invention of the formula (I) can be prepared by various alternative procedures. A preferred example thereof is a process according to Reaction Scheme-1 below.

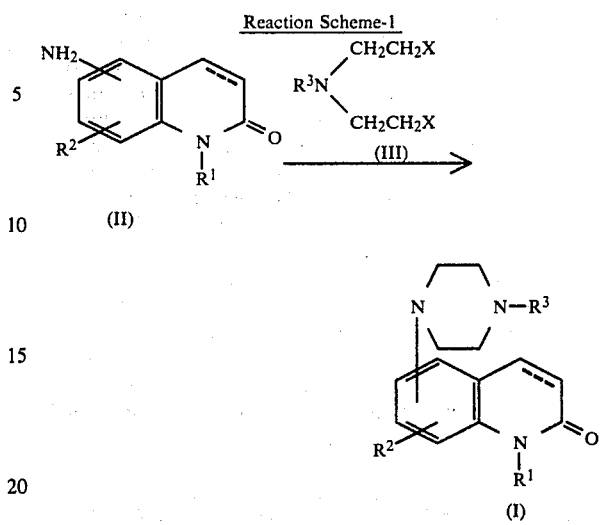

In the above formulae, X represents a halogen atom, a lower alkanesulfonyloxy group, an arylsulfonyloxy group, an aralkylsulfonyloxy group or a hydroxy group, and $R^1$, $R^2$, $R^3$ and the bonding between the 3- and 4-positions of the carbostyril nucleus have the same meanings as defined above.

In the formula (III), examples of the halogen arom represented by X include chlorine, fluorine, bromine and iodine; examples of the lower alkanesulfonyloxy group represented by X include a methanesulfonyloxy group, an ethanesulfonyloxy group, an isopropanesulfonyloxy group, a propanesulfonyloxy group, a butanesulfonyloxy group, a tert-butanesulfonyloxy group, a pentanesulfonyloxy group, a hexanesulfonyloxy group and the like; examples of the arylsulfonyloxy group represented by X include a substituted or unsubstituted arylsulfonyloxy group such as a phenylsulfonyloxy group, a 4-methylphenylsulfonyloxy group, a 2-methylphenylsulfonyloxy group, a 4-nitrophenylsulfonyloxy group, a 4-methoxyphenylsulfonyloxy group, a 3-chlorophenylsulfonyloxy group, an α-naphthylsulfonyloxy group and the like; and examples of the aralkylsulfonyloxy group represented by X include a substituted or unsubstituted aralkylsulfonyloxy group such as a benzylsulfonyloxy group, a 2-phenylethylsulfonyloxy group, a 4-phenylbutylsulfonyloxy group, a 4-methylbenzylsulfonyloxy group, a 2-methylbenzylsulfonyloxy group, a 2-nitrobenzylsulfonyloxy group, a 4-methoxybenzylsulfonyloxy group, a 3-chlorobenzylsulfonyloxy group, a α-naphthylmethylsulfonyloxy group and the like.

In the case where, of the compounds of the formula (III), those in which X represents a halogen atom, a lower alkanesulfonyloxy group, an arylsulfonyloxy group or an aralkylsulfonyloxy group are used as a starting material, the reaction between the compound of the formula (II) and the compound of the formula (III) can be carried out generally in a suitable inert solvent in the presence or absence of a basic condensing agent.

Examples of the suitable inert solvent which can be used include aromatic hydrocarbons such as benzene, toluene, xylene and the like, lower alcohols such as methanol, ethanol, isopropanol, butanol and the like, acetic acid, ethyl acetate, dimethyl sulfoxide, dimethylformamide, hexamethylenephosphoric triamide and the like.

Examples of the basic condensing agent include carbonates such as sodium carbonate, potassium carbonate, sodium hydrogencarbonate, potassium hydrogencarbonate and the like, metal hydroxides such as sodium hydroxide, potassium hydroxide and the like, metal alcoholates such as sodium methylate, sodium ethylate and the like, tertiary amines such as pyridine, triethylamine and the like.

In the above reaction, the proportion of the compound of the formula (III) to the compound of the formula (II) is not particularly limited, and can be varied broadly. Usually the reaction is carried out using at least an equimolar amount, and preferably from 1 to 5 mols, of the compound of the formula (III) per mol of the compound of the formula (II). The reaction can be carried out usually at about 40° to 120° C., preferably 50° to 100° C., and completed generally in about 5 to 30 hours.

On the other hand, in the case where, of the compounds of the formula (III), that in which X represents a hydroxy group is used as a starting material, the reaction between the compound of the formula (II) and the compound of the formula (III) can be carried out in the presence of a dehydrocondensing agent without solvents or in a suitable solvent.

Examples of the dehydrocondensing agent include polyphosphoric acids, phosphoric acids such as orthophosphoric acid, pyrophosphoric acid, metaphosphoric acid and the like, phosphorus acids such as orthophosphorus acid and the like, phosphoric anhydrides such as phosphorus pentoxide and the like, inorganic acids such as hydrochloric acid, sulfuric acid, boric acid and the like, metal phosphates such as sodium phosphate, boron phosphate, ferric phosphate, aluminum phosphate and the like, activated alumina, sodium hydrogensulfate, Raney nickel and the like.

As for the solvent, high boiling point solvents such as dimethylformamide, tetralin and the like can be used.

In the above reaction, the proportion of the compound of the formula (III) to the compound of the formula (II) is not particularly limited, and can be varied broadly. Usually, the reaction is carried out using at least an equimolar amount, and preferably 1 to 2 mols, of the compound of the formula (III) per mol of the compound of the formula (II).

The amount of the dehydrocondensing agent is not particularly limited, and can be varied broadly. Usually, at least a catalytic amount, preferably 0.5 to 5 mols, of the dehydrocondensing agent per mol of the compound of the formula (II) is used.

Preferably, the above reaction is carried out in a stream of an inert gas such as carbon dioxide, nitrogen in order to prevent oxidation reaction which is undesirable.

The reaction can be carried out either at atmospheric pressure or under pressure. Preferably, the reaction is carried out at atmospheric pressure.

The reaction can proceed advantageously usually at about 100° to 350° C., preferably 125° to 255° C. and completed generally in about 3 to 10 hours.

It should be noted that the compound of the formula (III) can be used in form of its pharmaceutically acceptable salt.

Of the compounds of the formula (I), those in which $R^3$ represents a lower alkanoyl group, a phenylcarbonyl group or a phenyl-lower alkanoyl group which may be substituted with 1 to 3 of a lower alkoxy group, a halogen atom, a lower alkyl group, a cyano group, a nitro group, an amino group, a lower alkanoylamino group, a lower alkylthio group, a lower alkanoyloxy group and a hydroxy group, or with a lower alkylenedioxy group on the benzene ring thereof; a furoyl group, a pyridylcarbonyl group or a lower alkoxycarbonyl group; $X^1$ represents a hydroxy group, $R^1$, $R^2$ and the bonding between the 3- and 4-positions of the carbostyril nucleus have the same meanings as defined above, can be prepared according to Reaction Scheme-2 below.

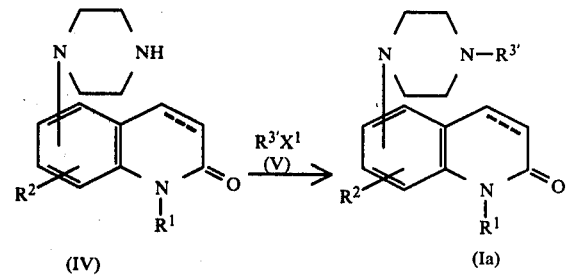

Reaction Scheme-2

In the above formulae, $R^{3'}$ represents a lower alkanoyl group, a phenylcarbonyl group or a phenyl-lower alkanoyl group which may be substituted with 1 to 3 of a lower alkoxy group, a halogen atom, a lower alkyl group, a cyano group, a nitro group, an amino group, a lower alkanoylamino group, a lower alkylthio group, a lower alkanoyloxy group and a hydroxy group, or with a lower alkylenedioxy group, a furoyl group, a pyridylcarbonyl group or a lower alkoxycarbonyl group; $X^1$ represents a hydroxy group; $R^1$, $R^2$ and the bonding between the 3- and 4-positions of the carbostyril nucleus have the same meanings as defined above.

The process shown in Reaction Scheme-2 above is a reaction between a carbostyril derivative of the formula (IV) and a carboxylic acid of the formula (V) using a conventional amido formation reaction. The process can readily be achieved with applying conditions for known amido formation reaction. Representative examples of the processes include:

(a) Mixed Acid Anhydride Process

The compound of the formula (V) is reacted with an alkyl haloformate to form mixed acid anhydride thereof which is then reacted with an amine of the formula (IV).

(b) Activated Ester Process

The carboxylic acid compound of the formula (V) is converted into a reactive ester such as a p-nitrophenyl ester, an N-hydroxy-succinimide ester, a 1-hydroxybenzotriazole ester, etc., which is then reacted with an amine of the formula (IV).

(c) Carbodiimide Process

The carboxylic acid compound of the formula (V) and an amine of the formula (IV) are condensed in the presence of an activating agent such as dicyclohexylcarbodiimide, carbonyldiimidazole, etc.

(d) Other Process

The carboxylic acid compound of the formula (V) is converted into an acid anhydride using a dehydrating agent such as acetic anhydride, etc., followed by reacting the product with an amine of the formula (IV);

process in which the lower alcohol ester of the carboxylic acid compound of the formula (V) is reacted with an amine of the formula (IV) at a high temperature under pressurized conditions; or the carboxylic acid compound of the formula (V) is converted into an acid halide using a halogenating agent followed by reacting the product with an amine of the formula (IV).

In the mixed acid anhydride process, the mixed acid anhydrides can be prepared in accordance with conventional Schötten-Baumann reaction and subjected further to reaction with the amine of the formula (VI) without isolation to give the compound of the formula (Ia).

The Schötten-Baumann reaction can be carried out in the presence of a basic compound. As for the basic compound, any conventional basic compounds conventionally used in Schötten-Baumann reaction can be used. Examples of suitable basic compounds include organic bases such as triethylamine, trimethylamine, pyridine, N,N-dimethylaniline, N-methylmorpholine, 1,5-diazabicyclo[4,3,0]nonene-5(DBN), 1,5-diazabicyclo[5,4,0]undecene-5(DBU), 1,4-diazabicyclo[2,2,2]octane (DABCO), etc., inorganic bases such as potassium carbonate, sodium carbonate, potassium hydrogencarbonate, sodium hydrogencarbonate, etc.

The reaction can proceed at about −20° to 100° C., preferably 0° to 50° C. and continued for about 5 minutes to 10 hours, preferably 5 minutes to 2 hours.

The reaction between the mixed acid anhydride and the amine of the formula (IV) can proceed at about −20° to 150° C., preferably 10° to 50° C. for about 5 minutes to 10 hours, preferably 5 minutes to 5 hours.

The mixed acid anhydride process can generally proceed in a solvent. As for the solvent any solvents used conventionally in the mixed acid anhydride processes can be used. Examples of suitable solvent include halogenated hydrocarbons such as methylene chloride, chloroform, dichloroethane, etc., aromatic hydrocarbons such as benzene, toluene, xylene, etc., ethers such as diethyl ether, tetrahydrofuran, dimethoxyethane, etc., ester such as methyl acetate, ethyl acetate, etc., and aprotic polar solvents such as N,N-dimethylformamide, dimethyl sulfoxide, hexamethylphosphoric triamide, etc.

Examples of suitable alkyl haloformate which can be used in the mixed acid anhydride process include methyl chloroformate, methyl bromoformate, ethyl chloroformate, ethyl bromoformate, isobutyl chloroformate, etc.

In the above reaction, the alkyl haloformate and the carboxylic acid compound of the formula (V) can be used usually in equimolar amounts relative to the amine of the formula (IV). However, 1 to 1.5 mols of the alkyl haloformate or the carboxylic acid compound of the formula (V) per mol of the amine of the formula (IV) can also be used.

On the other hand, the reaction between the carboxylic acid halide and the amine of the formula (IV) can be carried out in an appropriate solvent in the presence of a basic compound. As for the basic compound various known compounds can be used. For example, sodium hydroxide, potassium hydroxide, sodium hydride, potassium hydride, etc., in addition to the basic compounds used in the above Schötten-Baumann reaction can be used. Examples of suitable solvent include, in addition to those used in the above Schötten-Baumann reaction, alcohols such as methanol, ethanol, propanol, butanol, 3-methoxy-1-butanol, ethyl cellosolve, methyl cellosolve, etc., pyridine, acetone and the like.

Proportion of the carboxylic acid halide to the amine of the formula (IV) is not limited but can be varied widely. Usually, at least 1 mol, preferably 1 to 5 mols, of the carboxylic acid halide per mol of the amine of the formula (IV) is used.

The reaction can proceed usually at −20° to 180° C., preferably 0° to 150° C. and completed generally in 5 minutes to 30 hours.

Of the compounds of the formula (I), those in which $R^3$ represents a lower alkanesulfonyl group, a lower alkoxycarbonyl-lower alkyl group, a phenylsulfonyl group which may be substituted with a lower alkyl group on the benzene ring thereof, a lower alkyl group, a lower alkenyl group, a lower alkynyl group, or a phenyl-lower alkyl group which may be substituted with 1 to 3 of a lower alkoxy group, a lower alkyl group, a halogen atom, a nitro group, a cyano group, an amino group, a lower alkanoylamino group, a lower alkylthio group, a lower alkanoyloxy group and a hydroxy group or with a lower alkylenedioxy group on the benzene ring thereof can be prepared according to Reaction Scheme-3 below.

Reaction Scheme-3

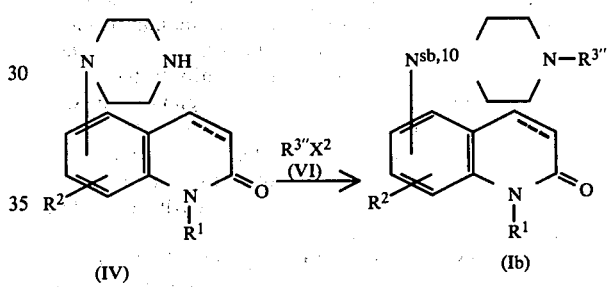

In the above formula $R^{3''}$ represents a lower alkanesulfonyl group, a lower alkoxycarbonyl-lower alkyl group, a phenylsulfonyl group which may be substituted with a lower alkyl group on the benzene ring thereof, a lower alkyl group, a lower alkenyl group, a lower alkynyl group, or a phenyl-lower alkyl group which may be substituted with 1 to 3 of a lower alkoxy group, a lower alkyl group, a halogen atom, a nitro group, a cyano group, an amino group, a lower alkanoylamino group, a lower alkylthio group, a lower alkanoyloxy group and a hydroxy group or with a lower alkylenedioxy group on the benzene ring thereof, $X^2$ represents a halogen atom, and $R^1$, $R^2$ and the bonding between the 3- and 4-positions of the carbostyril nucleus have the same meanings as defined above.

The reaction between the compound of the formula (IV) and the compound of the formula (VI) can be carried out under conditions similar to those used in the reaction between the compound of the formula (IV) and the carboxylic acid halide above.

Of the compounds of the formula (I), those in which $R^3$ represents a lower alkoxycarbonyl-lower alkyl group, a lower alkyl group, a lower alkenyl group, a lower alkynyl group or a phenyl-lower alkyl group which may be substituted with 1 to 3 of a lower alkoxy group, a lower alkyl group, a halogen atom, a nitro group, a cyano group, an amino group, a lower alkanoylamino group, a lower alkylthio group, a lower alkanoyloxy group and a hydroxy group or with a lower alkylenedioxy group can be prepared according to Reaction Scheme-4 below.

Reaction Scheme-4

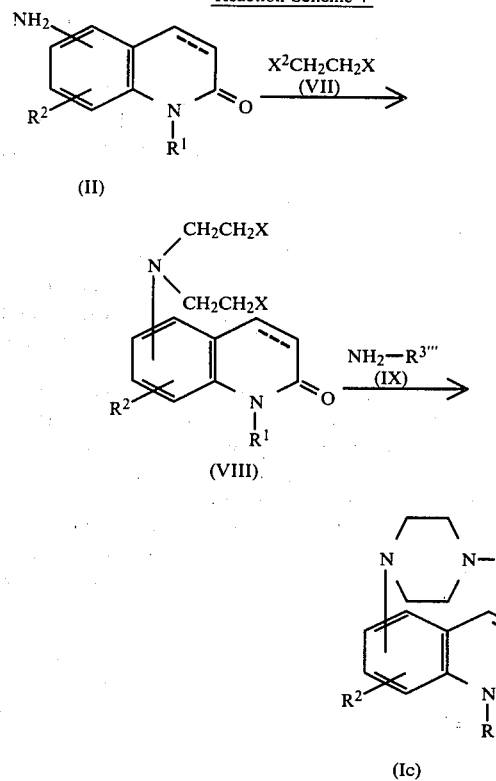

In the above formulae, $R^{3'''}$ represents a lower alkoxycarbonyl-lower alkyl group, a lower alkyl group, a lower alkenyl group, a lower alkynyl group or a phenyllower alkyl group which may be substituted with 1 to 3 of a lower alkoxy group, a lower alkyl group, a halogen atom, a nitro group, a cyano group, an amino group, a lower alkanoylamino group, a lower alkylthio group, a lower alkanoyloxy group and a hydroxy group or with a lower alkylenedioxy group on the benzene ring thereof, and $R^1$, $R^2$, X, $X^2$ and the bonding between the 3- and 4-positions of the carbostyril nucleus have the same meanings as defined above.

The reaction between the compound of the formula (II) and the compound of the formula (VII) can be carried out in the presence of a basic compound. As for the basic compound there can be used various known compounds, for example, inorganic salts such as sodium hydroxide, potassium hydroxide, sodium carbonate, potassium carbonate, sodium hydrogencarbonate, potassium hydrogencarbonate, silver carbonate, etc. alcoholates such as sodium methylate, sodium ethylate, etc., organic bases such as triethylamine, pyridine, N,N-dimethylaniline, etc.

The reaction can proceed either in the absence of solvents or in the presence of a solvent. As for the solvent, any inert solvents that do not affect the reaction adversely can be used.

Examples of suitable inert solvent include alcohols such as methanol, ethanol, propanol, ethylene glycol, etc., ethers such as dimethyl ether, tetrahydrofuran, dioxane, monoglyme, diglyme, etc., ketones such as acetone, methyl ethyl ketone, etc., aromatic hydrocarbons such as benzene, toluene, xylene, etc., esters such as methyl acetate, ethyl acetate, etc., aprotic polar solvents such as N,N-dimethylformamide, dimethyl sulfoxide, hexamethylphosphoric triamide, etc.

The reaction can be carried out advantageously in the presence of a metal iodide such as potassium iodide.

Proportion of the compound of the formula (VII) to the compound of the formula (II) is not limited particularly but can be varied widely. It is preferred that the compound of the formula (VII) be used usually in large excess amount when the reaction proceeds without solvents, and in an amount of 2 to 10 mols, preferably 2 to 4 mols, per mol of the compound of the formula (II) when the reaction proceeds in the presence of a solvent.

The reaction temperature is not limited particularly, but usually the reaction is carried out at about room temperature to 200° C., preferably 50° to 160° C. Usually, the reaction is continued for 1 to 30 hours.

The reaction between the compound of the formula (VIII) and the compound of the formula (IX) can be carried out under conditions analogous to those under which the reaction between the compound of the formula (II) and the compound of the formula (III) is carried out. Of the compounds of the formula (I), those in which $R^3$ represents a lower alkoxycarbonyl-lower alkyl group, a lower alkyl group, a lower alkenyl group, a lower alkynyl group or a phenyl-lower alkyl group which may be substituted with 1 to 3 of a lower alkoxy group, a lower alkyl group, a halogen atom, a nitro group, a cyano group, an amino group, a lower alkanoylamino group, a lower alkylthio group, a lower alkanoyloxy group and a hydroxy group or with a lower alkylenedioxy group on the benzene ring thereof can be prepared also according to Reaction Scheme-5 below.

Reaction Scheme-5

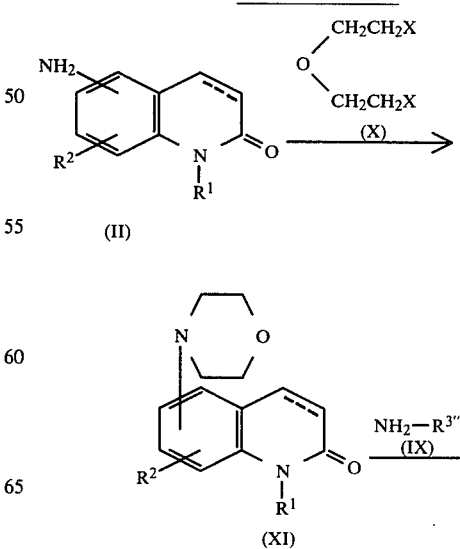

-continued
Reaction Scheme-5

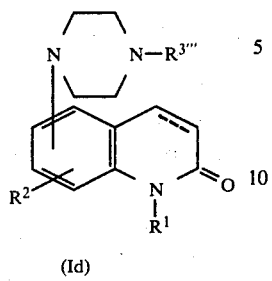

(Id)

In the above formulae, $R^1$, $R^2$, $R^{3'''}$, X and the bonding between the 3- and 4-positions of the carbostyril nucleus have the same meanings as defined above.

The reaction between the compound of the formula (II) and the compound of the formula (X) can be carried out under conditions similar to those used in the reaction between the compound of the formula (II) and the compound of the formula (III).

The reaction between the compound of the formula (XI) and the compound of the formula (IX) can be carried out either in the absence of solvents or in the presence of an appropriate solvent using an acid. Examples of the solvent which can be used include high boiling point solvents such as tetralin, dimethylformamide, dimethyl sulfoxide, hexamethylphosphoric triamide, etc. As for the acid, there can be used hydrochloric acid, sulfuric acid, hydrobromic acid, etc.

Proportion of the compound of the formula (IX) to the compound of the formula (XI) is not limited particularly, and can be varied widely. Usually, at least about 1 mol, preferably 1 to 2 mols, of the compound of the formula (IX) per mol of the compound of the formula (XI) is used.

The reaction can proceed usually at about 50° to 250° C., preferably 150° to 200° C. and completed generally in about 1 to 24 hours.

Further, the compounds of the formula (I) can be prepared according to Reaction Scheme-6 below.

Reaction Scheme-6

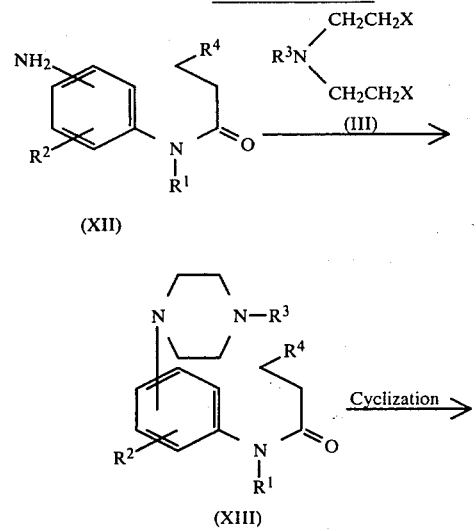

-continued
Reaction Scheme-6

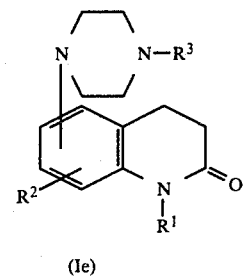

(Ie)

In the above formulae, $R^4$ represents a halogen atom, and $R^1$, $R^2$, $R^3$, X and the bonding between the 3-and 4-positions of the carbostyril nucleus have the same meanings as defined above.

The reaction between the compound of the formula (XII) and the compound of the formula (III) can be carried out under conditions similar to those used in the reaction between the compound of the formula (II) and the compound of the formula (III).

Cyclization reaction of the compound of the formula (XIII) which is called generally Friedel Crafts reaction can be carried out in a solvent in the presence of a Lewis acid.

As for the solvent, there can be used those conventionally employed in this type of reactions, for example, carbon disulfide, nitrobenzene, chlorobenzene, dichloromethane, dichloroethane, trichloroethane, tetrachloroethane, etc.

In the above reaction, any conventionally used Lewis acid can be used advantageously, for example, aluminum chloride, zinc chloride, ferrous chloride, tin chloride, boron tribromide, boron trifluoride, concentrated sulfuric acid, etc. The amount of Lewis acid which is used is not limited particularly but can be varied appropriately. Usually, about 2 to 6 mols, preferably 3 to 4 mols of Lewis acid per mol of the compound of the formula (XIII) is used.

The reaction temperature can be varied appropriately but usually is about 20° to 120° C., preferably 40° to 70° C. The reaction time depends on starting materials, catalysts, reaction temperature, etc., and cannot be set uniquely. Usually, the reaction is completed in about 0.5 to 6 hours.

The compound of the formula (I) can be prepared according to Reaction Scheme-7 below.

Reaction Scheme-7

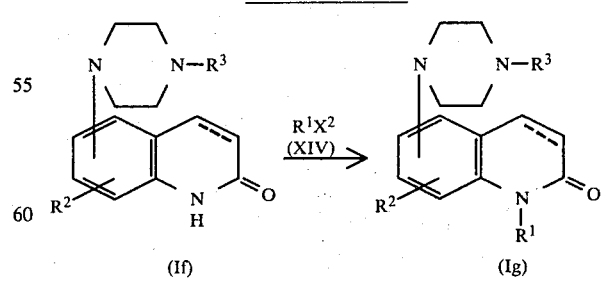

In the above formulae, $R^1$, $R^2$, $R^3$, $X^2$ and the bonding between the 3- and 4-positions of the carbostyril nucleus have the same meanings as defined above with the proviso that $R^1$ and $R^3$ should not be a hydrogen atom simultaneously.

The reaction between the compound of the formula (If) and the compound of the formula (XIV) can be carried out advantageously, for example, in an appropriate solvent in the presence of a basic compound.

As for the basic compound there can be used, for example, sodium hydride, potassium metal, sodium metal, sodium amide, potassium amide, etc. Examples of the solvent include ethers such as dioxane, diethylene glycoldimethyl ether, etc., aromatic hydrocarbons such as toluene, xylene, etc., aprotic polar solvents such as dimethylformamide, dimethyl sulfoxide, hexamethylphosphoric triamide, etc.

Proportion of the compounds of the formula (If) to the compound of the formula (XIV) is not limited particularly and can be varied freely. Usually, at least about 1 mol, preferably 1 to 2 mols, of the compound of the formula (XIV) per mol of the compound of the formula (If) is used.

The reaction can be carried out usually at about 0° to 70° C, preferably 0° C. to room temperature and completed generally in about 0.5 to 12 hours.

Of the compounds of the formula (I), those in which the bonding between the 3- and 4-positions of the carbostyril nucleus is a double bond (a single bond) can be prepared from the corresponding compounds in which such bonding is a single bond (a double bond) according to Reaction Scheme-8 below.

palladium-carbon, palladium black, vanadium oxide, Raney nickel, etc.

The amount of the oxidizing agent which is used is not limited particularly and can be varied widely. Usually, 1 to 5 mols, preferably 1 to 2 mols, of the oxidizing agent per mol of the compound of the formula (Ih) is used. When the hydrogenation catalysts are used, they are used in ordinary catalytic amounts.

Examples of suitable solvent include ethers such as dioxane, THF, methoxyethanol, dimethoxyethane, etc., aromatic hydrocarbons such as benzene, toluene, xylene, cumene, etc., halogenated hydrocarbons such as dichloromethane, dichloroethane, chloroform, carbon tetrachloride, etc., alcohols such as butanol, amyl alcohol, hexanol, etc., protic polar solvents such as acetic acid, etc., aprotic polar solvents such as DMF, DMSO, hexamethylphosphoric triamide, etc.

The reaction can be carried out usually at room temperature to 300° C., preferably at room temperature to 200° C. and completed generally in about 1 to 40 hours.

Of the compounds of the formula (I), those in which $R^1$ represents a hydrogen atom and the bonding between the 3- and 4-positions of the carbostyril nucleus is a double bond can be in the form of lactamlactim tautomers as shown below.

Reaction Scheme-8

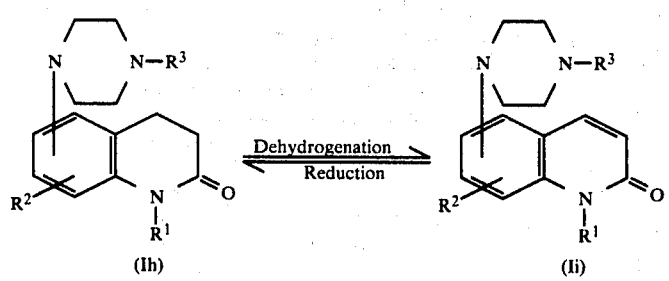

In the above formulae, $R^1$, $R^2$ and $R^3$ have the same meanings as defined above.

Reduction reaction of the compounds of the formula (Ii) can proceed under conventional conditions for catalytic reductions. Examples of the catalyst which can be used include metals such as palladium, palladium-carbon, platinum, Raney nickel, etc., in catalytic amounts usually used.

As for the solvent there can be used, for example, methanol, ethanol, isopropanol, dioxane, THF, hexane, cyclohexane, ethyl acetate, etc.

The reduction reaction can be carried out either at atmospheric pressure or superatomospheric pressure of hydrogen gas. Usually, the reaction is carried out at atmospheric to 20 kg/cm², preferably atmospheric to 10 kg/cm².

The reaction temperature is usually about 0° to 150° C., preferably at room temperature to 100° C.

Dehydrogenation reaction of the compound of the formula (Ih) can be carried out in an appropriate solvent using an oxidizing agent. Examples of suitable oxidizing agent include benzoquinones such as 2,3-dichloro-5,6-dicyanobenzoquinone, chloranil (2,3,5,6-tetrachlorobenzoquinone), etc., halogenating agents such as N-bromosuccinimide, N-chlorosuccinimide, bromine, etc., hydrogenation catalysts such as selenium dioxide,

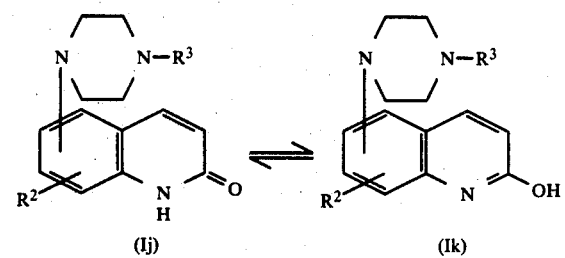

In the above formulae, $R^2$ and $R^3$ have the same meanings as defined above.

Further, the compound of the formula (I) can be prepared also according to Reaction Scheme-9 below.

Reaction Scheme-9

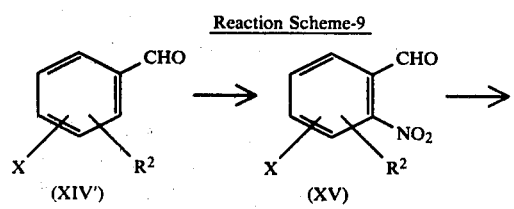

-continued
Reaction Scheme-9

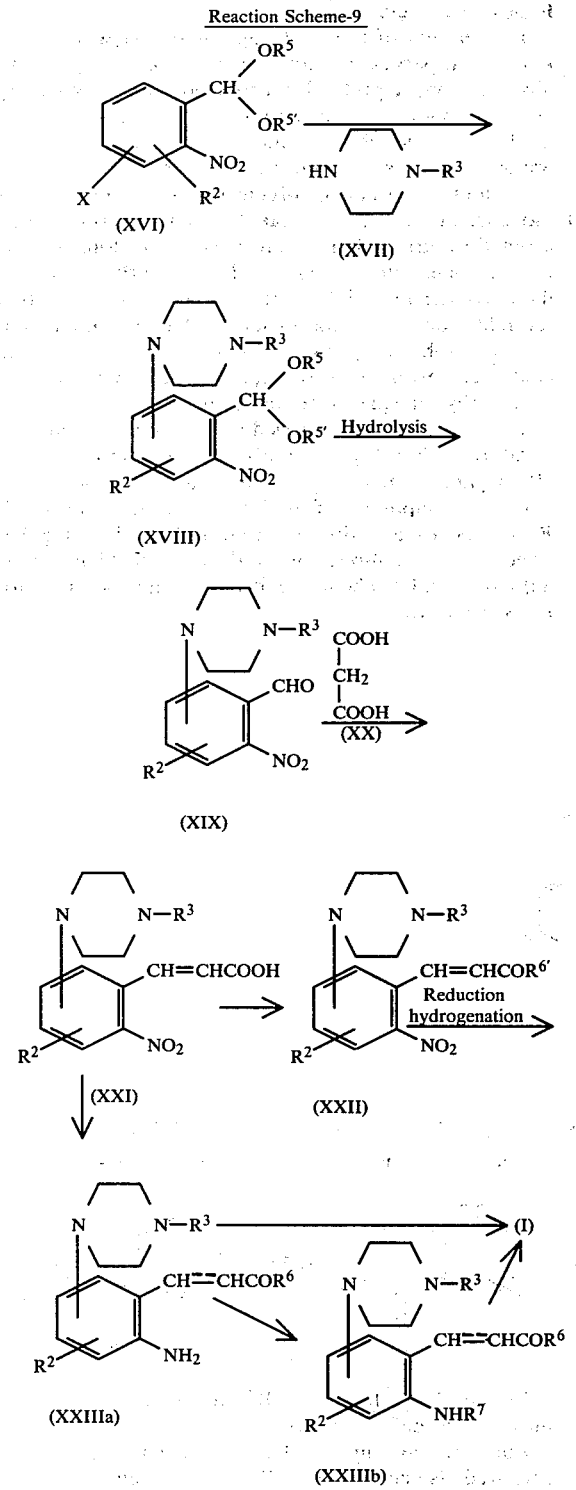

In the above formulae, $R^2$ and $R^3$ have the same meanings as defined above, $R^5$ and $R^{5'}$ each represents a lower alkoxy group or $R^5$ and $R^{5'}$ taken together with the oxygen atoms to which they are attached can combine to form a lower alkylenedioxy group, X represents a halogen atom, $R^6$ represents a hydroxy group or a lower alkoxy group, $R^{6'}$ represents a lower alkoxy group and $R^7$ represents a lower alkanoyl group.

Examples of the halogen atom represented by X include fluorine, chlorine, bromine, and iodine.

Examples of the lower alkylenedioxy group include a methylenedioxy group, an ethylenedioxy group, a trimethylenedioxy group, etc.

Of the compounds of the formula (XV), some are novel compounds and others are known compounds and can be prepared, for example, by nitration of the compounds of the formula (XIV').

Nitration reaction of the compound of the formula (XIV') can be carried out under conditions similar to those used in conventional nitration reactions of aromatic compounds, for example, using a nitration agent in the absence of solvents or in the presence of an appropriate inert solvent.

As for the inert solvent there can be illustrated, for example, acetic anhydride, concentrated sulfuric acid, etc., and as for the nitration agent there can be exemplified, for example, acids such as fuming nitric acid, concentrated nitric acid, mixed acid (a mixture of nitric acid with sulfuric acid, fuming sulfuric acid, phosphoric acid or acetic anhydride), a combination of sulfuric acid and alkali metal nitrates such as potassium nitrate, sodium nitrate, etc. The amount of the nitration agent to be used is usually at least equimolar amount, preferably excess amount relative to the starting compound, and the reaction can be carried out advantageously at about 0° C. to room temperature for 1 to 4 hours.

Acetalization reaction of the formyl group in the compound of the formula (XV) can be carried out in an appropriate solvent in the presence of an acetalization agent and an acid. In the reaction, any solvents that do not affect the reaction adversely can be used. For example, there can be used aromatic hydrocarbons such as benzene, toluene, xylene, etc., alcohols such as methanol, ethanol, etc., dimethylformamide, dimethyl sulfoxide, etc.

Examples of the acetalization agent include alcohols such as methanol, ethanol, isopropanol, ethylene glycol, etc., orthocarboxylic acid esters such as ethyl orthoformate, etc. As for the acid there can be illustrated, for example, mineral acids such as hydrochloric acid, sulfuric acid, etc., organic acids such as p-toluenesulfonic acid, etc.

The amount of acetalization agent to be used is at least 1 mol, preferably 1 to 1.5 mols, of the acetalization agent per mol of the compound of the formula (XV) when orthocarboxylic acid esters are used. On the other hand, when alcohols are used, at least 2 mols, usually large excess amount, of the acetalization agent per mol of the compound of the formula (XV) is used.

The reaction can be carried out at a temperature of usually at 0° to 50° C., preferably at about room temperature and completed in about 30 minutes to 5 hours.

The reaction between the compounds of the formula (XVI) and the compound of the formula (XVII) can be carried out in the presence of a solvent. As for the solvent there can be illustrated, for example, aromatic hydrocarbons such as benzene, toluene, xylene, etc., lower alcohols such as methanol, ethanol, isopropanol, etc., ethers such as dioxane, tetrahydrofuran, ethylene glycol dimethyl ether, diethyl ether, etc., polar solvents such as N-methylpyrrolidone, N,N-dimethylformamide, dimethyl sulfoxide, hexamethylphosphoric triamide, etc.

More advantageously, the reaction can be carried out using a basic compound as an acid acceptor. Examples of the basic compound include potassium carbonate, sodium carbonate, sodium hydroxide, sodium hydrogencarbonate, sodium amide, sodium hydride, tertiary amines such as triethylamine, tripropylamine, etc., pyridine, quinoline and the like.

In the above reaction, a suitable amount of the piperazine derivative of the formula (XVII) to be used is usually 1 to 10 mols, preferably 3 to 7 mols, of the compound of the formula (XVII) per mol of the compound of the formula (XVI).

The reaction can proceed usually at 50° to 150° C., preferably 50° to 100° C. and completed generally in about 1.5 to 10 hours.

Hydrolysis reaction of the compound of the formula (XVIII) can be carried out in an alcohol such as methanol, ethanol, isopropanol, etc., using mineral acid such as hydrochloric acid, sulfuric acid, etc., at a reaction temperature of from room temperature to the boiling point of solvent to be used for 30 minutes to 3 hours.

The reaction between the compound of the formula (XIX) and malonic acid of the formula (XX) can be carried out in an appropriate solvent in the presence of a basic compound. As the solvent, there can be used any solvents that can be used in the reaction between the compound of the formula (XVI) and the compound of the formula (XVII). In addition, polar solvents such as pyridine can also be used.

Examples of suitable basic compound include potassium carbonate, sodium carbonate, sodium hydroxide, sodium hydrogencarbonate, sodium amide, sodium hydride, tertiary amines such as triethylamine, tripropylamine, piperidine, etc., pyridine, quinoline, and the like.

In the above reaction, a suitable amount of malonic acid of the formula (XX) is at least equimolar amount, preferably 2 to 7 mols, of the compound of the formula (XX) per mol of the compound of the formula (XIX).

The reaction can proceed usually at about 0° to 200° C. and be completed generally in about 1 to 10 hours.

Esterification reaction of the compound of the formula (XXI) can be carried out in an alcohol such as methyl alcohol, ethyl alcohol, isopropyl alcohol, etc., in the presence of an acid such as hydrochloric acid, sulfuric acid, etc., or a halogenating agent such as thionyl chloride, phosphoric oxychloride, phosphorus pentachloride, phosphorus trichloride, etc., at a reaction temperature of about 0° to 150° C., preferably 50° to 100° C., for about 1 to 10 hours.

In the above reaction, a suitable amount of the acid to be used is usually 1 to 1.2 mols per mol of the compound of the formula (XXI) and the amount of the halogenating agent to be used is at least equimolar amount, preferably 1 to 5 mols, of the halogenating agent per mol of the compound of the formula (XXI).

Reduction reaction of the compounds of the formula (XXI) and of the formula (XXII) can be carried out either (1) by effecting reduction in an appropriate solvent using a catalyst for catalytic reduction, or (2) by effecting reduction using a reducing agent such as mixture of a metal or metal salt and an acid, a mixture of a metal or metal salt and an alkali metal hydroxide, sulfate or ammonium salt, and the like.

When catalytic reduction (1) is used, examples of the solvent which can be used include water, acetic acid, alcohols such as methanol, ethanol, isopropanol, etc., hydrocarbons such as hexane, cyclohexane, etc., ethers such as diethylene glycol dimethyl ether, dioxane, tetrahydrofuran, diethyl ether, etc., esters such as ethyl acetate, methyl acetate, etc., aprotic polar solvents such as N,N-dimethylformamide, etc. As for the catalyst there can be used palladium, palladium black, palladium-carbon, platinum, platinum oxide, copper chromite, Raney nickel, etc. A suitable amount of the catalyst to be used is 0.02 to 1.00 part by weight per part by weight of the compound of the formula (XXI) or (XXII). The reaction can be carried out at about −20° C. to room temperature, preferably 0° C. to room temperature, at a hydrogen gas pressure of 1 to 10 atm for about 0.5 to 10 hours.

On the other hand, when the reaction (2) above is used, a mixture of iron, zinc, tin or stannous chloride and a mineral acid such as hydrochloric acid, sulfuric acid, etc., or a mixture of iron, ferrous sulfate, zinc or tin and an alkali metal hydroxide such as sodium hydroxide, etc., sulfates such as ammonium sulfate, etc., ammoniacal water or an ammonium salt such as ammonium chloride, etc., can be used as a reducing agent.

Examples of suitable inert solvent which can be used include water, acetic acid, metahnol, ethanol, dioxane, etc.

Conditions for the above reduction reaction can be selected appropriately depending upon the reducing agent to be used. For example, when a mixture of stannous chloride and hydrochloric acid is used as a reducing agent, the reaction can proceed advantageously at about 0° C. to room temperature for about 0.5 to 10 hours. A suitable amount of the reducing agent is at least equimolar amount, preferably 1 to 5 mols, of the reducing agent per mol of the starting compound.

Further, when the reaction (1) above is carried out preferably at 50° to 150° C., the compound of the formula (I) can be obtained by direct cyclization without isolation of the compound of the formula (XXIIIa) or (XXIIIb).

Acylation reaction of the compound of the formula (XXIIIa) can be carried out under conditions analogous to those under which the compounds of the formula (I) in which $R^3$ represents a lower alkanoyaminobenzoyl group can be prepared as described hereinafter.

Cyclization reaction of the compound of the formula (XXIII) to form the compound of the formula (I) can proceed in an appropriate solvent in the absence or in the presence of a basic compound or an acid, preferably in the presence of an acid.

Examples of suitable basic compounds include organic bases such as triethylamine, trimethylamine, pyridine, dimethylaniline, N-methylmorpholine, 1,5-diazabicyclo[4,3,0]nonene-5 (DBN), 1,5-diazabicyclo[5,4,0]undecene-5 (DBU), 1,4-diazabicyclo[2,2,2]octane (DABCO), etc., inorganic bases such as potassium carbonate, sodium carbonate, sodium hydroxide, potassium hydroxide, sodium hydride, potassium hydride, potassium hydrogencarbonate, sodium hydrogencarbonate, etc .

Examples of suitable acids include hydrochloric acid, sulfuric acid, polyphosphoric acid, etc.

As for the solvent any solvents which do not affect the reaction adversely can be used. Examples of suitable solvent include alcohols such as methanol, ethanol, propanol, butanol, 3-methoxy-1-butanol, ethyl cellosolve, methyl cellosolve, etc., pyridine, acetone, halogenated hydrocarbons such as methylene chloride, chloroform, dichloroethane, etc., aromatic hydrocarbons such as benzene, toluene, xylene, etc., ethers such as diethyl ether, tetrahydrofuran, dimethoxyethane, etc., esters such as methyl acetate, ethyl acetate, etc., and aprotic polar solvents such as N,N-dimethylformamide, dimethyl sulfoxide, hexamethylphosphoric triamide, etc., and a mixture thereof.

The reaction can proceed usually at −20° to 150° C., preferably 0° to 150° C. and can be completed generally in 5 minutes to 30 hours.

Of the compounds of the formula (If) according to this invention, those in which $R^3$ represents a phenylcarbonyl group, a phenyl-lower alkyl group or a phenyl-lower alkanoyl group, each of which has 1 to 3 amino groups on the benzene ring thereof can be prepared readily by reducing a corresponding compound in which $R^3$ represents a phenylcarbonyl group, a phenyl-lower alkyl group or a phenyl-lower alkanoyl group each of which has 1 to 3 nitro groups on the benzene ring thereof. This reduction reaction can be carried out in an analogous manner as in conventional reactions in which an aromatic nitro compound is reduced to corresponding aromatic amino compound. More particularly, a process in which a reducing agent such as sodium nitrite, sulfurous acid gas, etc., a catalytic reduction, a process using a reducing catalyst such as palladium-carbon, etc., and the like processes can be used.

Of the compounds of the formula (I) those in which $R^2$ represents a hydrogen atom can also be prepared by subjecting to ether decomposition a corresponding compound of the formula (I), wherein $R^2$ represents a lower alkoxy group. The ether decomposition can be carried out in the presence of a Lewis acid, for example, boron tribromide, boron trifluoride, aluminium chloride, etc., usually in an excess amount relative to the starting compound at a temperature usually at about −30° C. to room temperature.

Of the compounds of the formula (I), those in which $R^3$ represents a phenylcarbonyl group, a phenyl-lower alkyl group or a phenyl-lower alkanoyl group, each of which is substituted with 1 to 3 of a lower alkanoylamino group and a lower alkanoyloxy group on the benzene ring thereof can be prepared by acylating a corresponding compound of the formula (I) in which $R^3$ represents a phenylcarbonyl group, a phenyl-lower alkyl group or a phenyl-lower alkanoyl group, each of which is substituted with 1 to 3 of an amino group and a hydroxy group on the benzene ring thereof.

As for the acylating agent there can be illustrated, for example, lower alkanoic acids such as acetic acid, etc., lower alkanoic acid anhydrides such as acetic anhydride, etc., lower alkanoic acid chlorides such as acetyl chloride, etc.

When a lower alkanoic acid anhydride or a lower alkanoic acid halide is used as an acylating agent, the acylation reaction can be used in the presence of a basic compound. As for the basic compound there can be illustrated, for example, alkali metals such as sodium metal, potassium metal, etc., hydroxides, carbonates and hydrogencarbonates thereof, aromatic amines such as pyridine, piperidine, etc.

The reaction can be proceed either in the absence of solvents or in the presence of a solvent. Usually, it can be carried out in an appropriate solvent. As for the solvent there can be illustrated, for example, ketones such as acetone, methyl ethyl ketone, etc., ethers such as diethyl ether, dioxane, etc., aromatic hydrocarbons such as benzene, toluene, xylene, etc., water and the like.

A suitable amount of acylating agent to be used is an equimolar amount to a large excess amount, preferably 5 to 10 mols, of the acylating agent per mol of the starting compound.

The reaction can proceed at 0° to 150° C., preferably 0° to 80° C.

When a lower alkanoic acid is used as an acylating agent, the reaction can proceed advantageously in the presence of a dehydrating agent, for example, mineral acids such as sulfuric acid, hydrochloric acid, etc., sulfonic acids such as p-toluenesulfonic acid, benzenesulfonic acid, ethanesulfonic acid, etc., with keeping the reaction temperature preferably at 50° to 120° C.

Of the compounds of the formula (I), those in which $R^3$ represents a phenylcarbonyl group, a phenyl-lower alkyl group or a phenyl-lower alkanoyl group, each of which is substituted with 1 to 3 of a hydroxy and an amino group on the benzene ring thereof can be prepared by hydrolyzing a corresponding compound of the formula (I) in which $R^3$ represents a phenylcarbonyl group, a phenyl-lower alkyl group or a phenyl-lower alkanoyl group, each of which is substituted with 1 to 3 of a lower alkanoylamino group and a lower alkanoyloxy group on the benzene ring thereof.

The hydrolysis reaction can be carried out in an appropriate solvent in the presence of an acid or a basic compound. As for the solvent there can be illustrated, for example, water, lower alcohols such as methanol, ethanol, isopropanol, etc., ethers such as dioxane, tetrahydrofuran, etc., and a mixture thereof. Examples of suitable acid include mineral acids such as hydrochloric acid, sulfuric acid, hydrobromide, etc., and examples of suitable basic compound include metal hydroxides such as sodium hydroxide, potassium hydroxide, calcium hydroxide, etc.

The reaction can proceed advantageously at room temperature to 150° C., preferably 80° to 120° C. and can be completed generally in about 1 to 15 hours.

The compounds of the formula (I) can also be prepared according to Reaction Scheme-10 below.

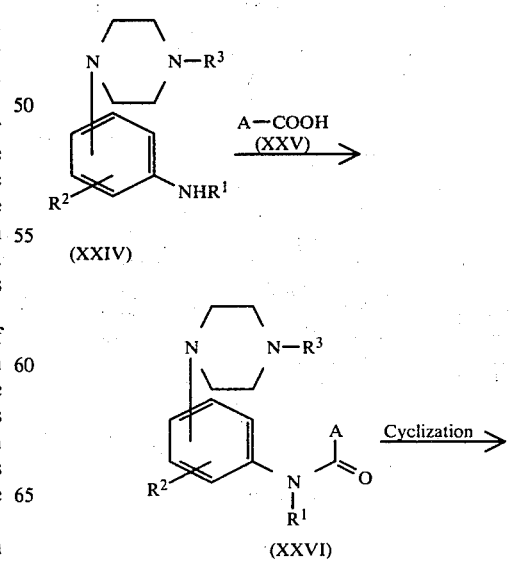

-continued
Reaction Scheme-10

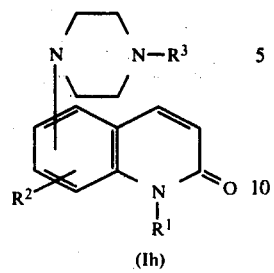

(Ih)

In the above formulae, $R^1$, $R^2$ and $R^3$ have the same meanings as defined above, A represents a group of the formula $R^{7'}CH=CH-$ where $R^{7'}$ represents a lower alkoxy group or a halogen atom, a group of the formula

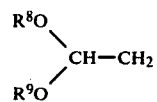

where $R^8$ and $R^9$ each represents a lower alkyl group, or a $CH\equiv C-$ group.

The compound of the formula (XXIV) and the compound of the formula (XXV) are known compounds and the reaction between them can be carried out in an analogous manner as in the reaction between the compounds (IV) and (V) described hereinbefore.

Cyclization reaction of the aniline derivative of the formula (XXVI) can be carried out in the presence of an acid without solvents or in an appropriate solvent. Acid is not limited particularly and a wide variety of inorganic and organic acids commonly used can be used. More particularly, inorganic acids such as hydrochloric acid, hydrobromic acid, sulfuric acid, etc., Lewis acids such as aluminum chloride, boron trifluoride, titanium tetrachloride, etc., organic acids such as formic acid, acetic acid, ethanesulfonic acid, p-toluenesulfonic acid, etc. can be used. Of these acids, hydrochloric acid, hydrobromic acid and sulfuric acid are preferred.

The amount of acid to be used is not limited particularly and can be selected appropriately within a wide range. Usually, at least equimolar amount, preferably 10 to 50 parts by weight, of the acid per part by weight of the compound of the formula (XXVI) is used.

As for the solvent, any inert solvents that are used conventionally can be used. Examples of suitable solvent include water, lower alcohols such as methanol, ethanol, propanol, etc., ethers such as dioxane, tetrahydrofuran, aromatic hydrocarbons such as benzene, toluene, etc., halogenated hydrocarbons such as methylene chloride, chloroform, carbon tetrachloride, etc., acetone, dimethyl sulfoxide, dimethylformamide, hexamethylphosphoric triamide, etc. Of these, watersoluble solvents such as the lower alcohols, the ethers, acetone, dimethyl sulfoxide, dimethylformamide, hexamethylphosphoric triamide, etc., are preferred.

The above reaction can proceed at 0° to 100° C., preferably room temperature to 60° C, and can be completed usually in about 5 minutes to 6 hours.

Further, the compounds of the formula (I) can be prepared according to Reaction Scheme-11 below.

Reaction Scheme-11

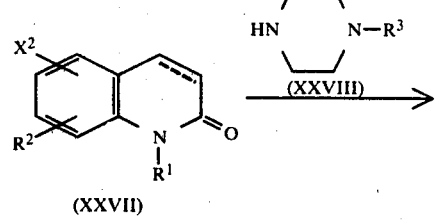

(XXVII)

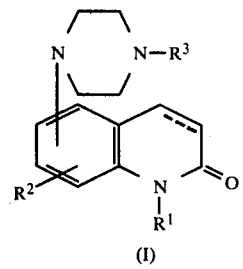

(I)

In the above formulae, $R^1$, $R^2$, $R^3$ and $X^2$ have the same meanings as defined above.

The reaction between the compounds of the formula (XXVII) and the compound of the formula (XXVIII) can be carried out in an appropriate inert solvent with or without the addition of a basic condensing agent. As for the inert solvent there can be illustrated, for example, aromatic hydrocarbons such as benzene, toluene, xylene, etc., alcohols such as methanol, ethanol, propanol, butanol, 3-methoxy-1-butanol, ethyl cellosolve, methyl cellosolve, etc., pyridine, acetone, dimethyl sulfoxide, dimethylformamide, hexamethylphosphoric triamide, etc.

Examples of suitable basic agent include sodium carbonate, potassium carbonate, sodium hydrogencarbonate, potassium hydrogencarbonate, sodium hydroxide, potassium hydroxide, sodium hydride, potassium hydride, triethylamine, etc.

Proportion of the compounds of the formula (XXVIII) to (XXVII) is not limited particularly and can be changed widely. Usually, at least about equimolar amount, preferably 1 to 5 mols, of the compound of the formula (XXVIII) per mol of the compound of the formula (XXVII) is used.

The reaction can be carried out usually at about room temperature to 180° C., preferably 100° to 150° C. and completed generally in about 3 to 30 hours. Further, the reaction can proceed advantageously in the presence of copper powder as a catalyst.

Of the compounds of the formula (II), those in which an amino group is present on the 8-position can also be prepared according to Reaction Scheme-12 below.

Reaction Scheme-12

-continued

Reaction Scheme-12

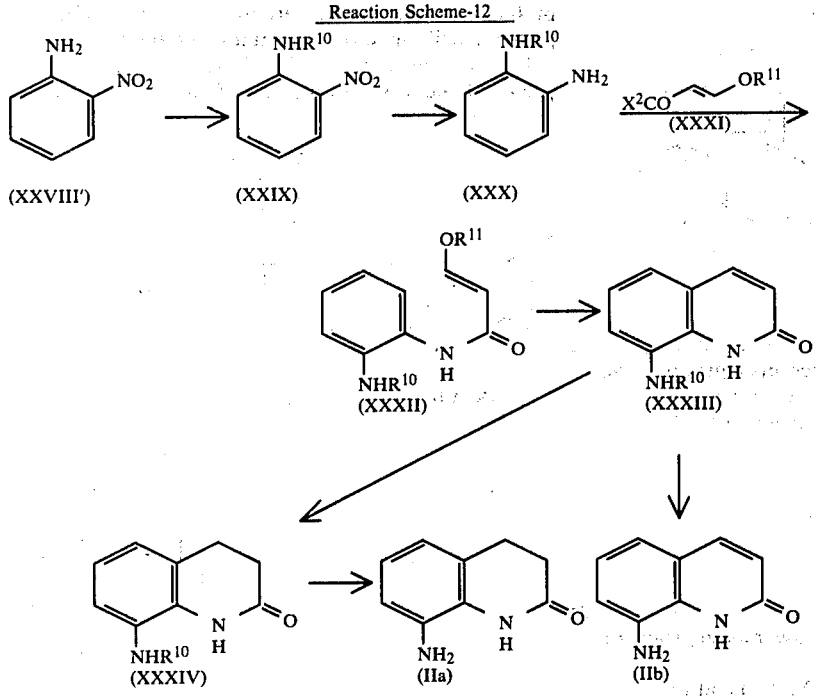

In the above formulae, $R^{10}$ represents a lower alkanoyl group, $R^{11}$ represents a lower alkyl group; and $X^2$ represents a halogen atom.

Acylation reaction of the compound of the formula (XXVIII') can be carried out in an analogous manner as in the acylation reaction of the compound of the formula (XXIIIa) above.

Reduction reaction of the nitro group in the compound of the formula (XXIX) can be carried out in an analogous manner as in the reduction reaction of the compound of the formula (XXI) or (XXII).

Reaction between the compound of the formula (XXX) and the compound of the formula (XXXI) can be carried out under conditions analogous to those under which the compound of the formula (IV) is reacted with the compound of the formula (V) except that the reaction conditions of using carboxylic acid halide as compound of the formula (V) and its ratio to be used are different. Although this reaction can proceed in the absence of basic compounds, it can proceed advantageously with at least equimolar amount, preferably 1 to 5 mols, of the compound of the formula (XXX) per mol of the compound of the formula (XXXI).

Cyclization reaction of the compound of the formula (XXXII) can be carried out under the conditions analogous to those under which the cyclization reaction of the compound of the formula (XXVI) is carried out.

Reduction reaction of the carbostyril derivative of the formula (XXXIII) can be carried out in an analogous manner as in the reduction reaction of the carbostyril derivative of the formula (Ii).

Hydrolysis reaction of the carbostyril derivative of the formula (XXXIII) or (XXXIV) can be carried out in an analogous manner as in the reduction reaction of the compound of the formula (I) in which $R^3$ represents a lower alkanoylamino benzoyl group.

The compounds of this invention represented by the formula (I) prepared as described above can form pharmaceutically acceptable salts with acids and this invention also includes within its scope such pharmaceutically acceptable salts. The pharmaceutically acceptable acids which can be used for the salt formation can be various inorganic acids, for example, hydrochloric acid, sulfuric acid, phosphoric acid, hydrobromic acid, organic acids such as oxalic acid, maleic acid, fumaric acid, malic acid, tartaric acid, citric acid, benzoic acid and the like.

The compounds of the formula (I) can be converted into a corresponding salt when they have an acid group by reacting the acid group with a pharmaceutically acceptable basic compound. Examples of basic compounds are inorganic basic compounds such as sodium hydroxide, potassium hydroxide, calcium hydroxide, sodium carbonate, potassium hydrogencarbonate and the like.

The compounds of the formula (I) and the salts thereof obtained as described above can be isolated from the respective reaction mixtures upon completion of the reaction and purified by conventional procedures, for example, solvent extraction, dilution method, precipitation, recrystallization, column chromatography, preparative thin layer chromatography and the like.

As is apparent to those skilled in the art, the compounds of the formula (I) can exist in optically active forms and this invention includes such optical isomers within its scope.

In using the compounds of this invention of the formula (I) and the salts thereof as therapeutic agents, these compounds can be formulated into pharmaceutical compositions together with ordinary pharmaceutically acceptable carriers. Suitable carriers which can be used are, for example, solvents or excipients such as fillers, extenders, binders, wetting agents, disintegrants, surface active agents and lubricants which are usually employed to prepare such drugs depending on the type of dosage form.

Various dosage forms of the therapeutic agents as an cardiotonic agent can be selected according to the purpose of the therapy. Typical dosage forms which can be used are tablets, pills, powders, liquid preparations, suspensions, emulsions, granules, capsules, suppositories, and injectable preparations (solutions, suspensions, etc.).

In molding a pharmaceutical composition containing the compounds of the formula (I) or the pharmaceutically acceptable salt thereof as an active ingredient into a tablet form, a wide range of carriers known in the art can be used. Examples of suitable carriers include excipients such as lactose, white sugar, sodium chloride, glucose solution, urea, starch, calcium carbonate, kaolin, crystalline cellulose and silicic acid, binders such as water, ethanol, propanol, simple syrup, glucose, starch solution, gelatin solution, carboxymethyl cellulose, shellac, methyl cellulose, potassium phosphate and polyvinyl pyrrolidone, disintegrants such as dried starch, sodium alginate, agar powder, laminaria powder, sodium hydrogen carbonate, calcium carbonate, Tween, sodium lauryl sulfate, stearic acid monoglyceride, starch, and lactose, disintegration inhibitors such as white sugar, stearic acid glyceryl ester, cacao butter and hydrogenated oils, absorption promotors such as quaternary ammonium bases and sodium lauryl sulfate, humectants such as glycerol and starch, adsorbents such as starch, lactose, kaolin, bentonite and colloidal silicic acid, and lubricants such as purified talc, stearic acid salts, boric acid powder, Macrogol (trade name for a polyethylene glycol produced by Shinetsu Chemical Industry Co., Ltd.) and solid polyethylene glycol.

The tablets, if desired, can be coated, and made into sugar-coated tablets, gelatin-coated tablets, enteric-coated tablets, film-coated tablets, or tablets comprising two or more layers.

In molding the pharmaceutical composition into pills, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar.

In molding the pharmaceutical composition into a suppository form, a wide variety of carriers known in the art can be used. Examples of suitable carriers include polyethylene glycol, cacao butter, higher alcohols, esters of higher alcohols, gelatin, and semisynthetic glycerides.

When the pharmaceutical composition is formulated into an injectable preparation, the resulting solution and suspension are preferably sterilized, and are isotonic with respect to the blood. In formulating the pharmaceutical composition into the form of a solution or suspension, all diluents customarily used in the art can be used. Examples of suitable diluents are water, ethyl alcohol, propylene glycol, ethoxylated isostearyl alcohol, polyoxyethylene sorbitol, and sorbitan esters. Sodium chloride, glucose or glycerol may be incorporated into a therapeutic agent, e.g., as a nephritis treating agent in an amount sufficient to prepare isotonic solutions. The therapeutic agent may further contain ordinary dissolving aids, buffers, pain-alleviating agents, and preservatives, and optionally coloring agents, perfumes, flavors, sweeteners, and other drugs.

The amount of the compound of the formula (I) and the pharmaceutically acceptable salts thereof of this invention as an active ingredient to be incorporated into a pharmaceutical composition useful as a cardiac stimulant is not particularly limited, and can vary over a wide range. A suitable therapeutically effective amount of the compound of the general formula (I) and the pharmaceutically acceptable salts thereof of this invention is usually about 1 to about 70% by weight, preferably 1 to 30% by weight, based on the entire composition.

There is no particular restriction on the manner of using the cardiotonic agent, and it can be administered by routes suitable for the particular forms thereof. For example, the tablets, pills, liquid preparations, suspensions, emulsions, granules, and capsules are orally administered. The injectable preparations are intravenously administered either alone or together with ordinary auxiliary agents such as glucose and amino acids. Furthermore, as required, the cardiotonic agent can be singly administered intramuscularly, intracutaneously, subcutaneously, or intraperitoneally. The suppository is administered intrarectally and the ointment is coated on the skin.

The dosage of the cardiotonic agent is suitably selected according to the purpose of use, the symptoms, etc. Usually, a preferred dosage of the compound of this invention is about 0.1 to 10 mg/kg body weight per day. It is advantageous that the active ingredient is contained in a single unit dose form in an amount of 2 to 200 mg.

Hereinafter, this invention will be described in greater detail with reference to Reference Examples, Examples and Preparation Examples.

REFERENCE EXAMPLE 1

Concentrated nitric acid (29.3 ml) was added dropwise to 500 ml of concentrated sulfuric acid with ice cooling externally while stirring. In addition, 50 g of m-chlorobenzaldehyde was added dropwise to the resulting mixture at 5° C. or less. After stirring was continued at room temperature for 1 hour the reaction mixture was poured onto ice to precipitate solids which were collected by filtration. After washing with water the solids thus-obtained were dissolved in methylene chloride and the methylene chloride layer was washed with a dilute aqueous sodium hydroxide, washed with water and dried over sodium sulfate. Removal of the solvent by distillation gave 62.3 g of 2-nitro-5-chlorobenzaldehyde, m.p. 65°–69° C.

REFERENCE EXAMPLE 2

2Nitro-5-chlorobenzaldehyde (100 g) was dissolved in 1,000 ml of toluene and then, 10 g of p-toluenesulfonic acid and 87.8 g of ethyl orthoformate were added to the resulting solution. The mixture was stirred at room temperature for 1 hour, and the reaction mixture was neutralized with a dilute aqueous sodium hydroxide solution. After washing with water the toluene layer was dried over anhydrous sodium sulfate and concentrated to obtain 138 g of oily product of 2-nitro-5-chlorobenzaldehyde diethyl acetal.

REFERENCE EXAMPLE 3

2-Nitro-5-chlorobenzaldehyde diethyl acetal (138 g) was dissolved in 750 ml of dimethylformamide (DMF) and to the solution was added 250 g of anhydrous piperazine and stirred at 80° C. for 4 hours. After removing excessive piperazine and DMF by evaporation under reduced pressure, and a dilute aqueous sodium hydroxide solution was added to the residue to dissolve. Then, the solution was extracted with methylene chloride. The methylene chloride layer was washed with water and dried over sodium sulfate followed by removal of the solvent by distillation. To the residue was added 850 ml of isopropyl alcohol to dissolve, and to the solution was added 65 ml of concentrated hydrochoric acid and heated under reflux for 1 hour. After cooling, the crystals which precipitated were collected by filtration to give 93 g of 2-nitro-5-piperazinylbenzaldehyde hydrochloride, m.p. 195°–201° C.

REFERENCE EXAMPLE 4

2-Nitro-5-piperazinylbenzaldehyde hydrochloride (47 g) was dissolved in 500 ml of pyridine and 5 g of piperidine and 100 g of malonic acid were added to the solution followed by heating under reflux for 5 hours. After cooling, crystals which formed were collected by filtration to give 42 g of 2-nitro-5-piperazinylcinnamic acid, m.p. 229°–237° C.

REFERENCE EXAMPLE 5

2-Nitro-5-piperazinylcinnamic acid (10 g) was suspended in 100 ml of ethyl alcohol and to the suspension was added dropwise 3 ml of thionyl chloride with ice cooling externally while stirring. After completion of addition, the mixture was heated under reflux for 3 hours and ethyl alcohol and thionyl chloride were removed by distillation. The residue was added to isopropyl alcohol and heated to dissolve. After cooling, yellow crystals which precipitated were collected by filtration to give 4.3 g of 2-nitro-5-piperazinylcinnamic acid ethyl ester hydrochloride, m.p. 210°–220° C.

REFERENCE EXAMPLE 6

2-Nitro-5-piperazinylbenzaldehyde (5 g) was suspended in 50 ml of DMF and 6 ml of triethylamine was added to the suspension. A solution of 4.4 g of 3,4-dimethoxybenzoyl chloride in 20 ml of DMF was added dropwise thereto with ice cooling externally while stirring and the mixture was stirred at room temperature for 2 hours and poured into saturated saline and extracted with methylene chloride. After washing with water, the methylene chloride layer was dried over anhydrous sodium sulfate. Then, the solvent was removed by distillation and to the residue was added methyl alcohol and the mixture was heated and cooled and crystals which formed were recrystallized form DMF to give 4.5 g of 2-nitro-5-[4-(3,4-dimethoxybenzoyl)-1-piperazinyl]benzaldehyde, m.p. 196°–198° C., yellow crystal.

REFERENCE EXAMPLE 7

2-Nitro-5-[4-(3,4-dimethoxybenzoyl)-1-piperazinyl]-benzaldehyde (4 g) was dissolved in 20 ml of pyridine followed by adding 2.1 g of malonic acid and 0.4 ml of piperidine, and the mixture was stirred at 80° C. for 4 hours. After evaporating pyridine and piperidine the reaction mixture was poured in a dilute aqueous hydrogen chloride solution and extracted with methylene chloride. After washing the methylene chloride layer with water the solvent was distilled off and methanol was added to the residue. After cooling, crystals which formed were collected by filtration to give 3.7 g of 2-nitro-5-[4-(3,4-dimethoxybenzoyl)-1-piperazinyl]-cinnamic acid, m.p. 197°–202° C.

REFERENCE EXAMPLE 8

2-Nitro-5-[4-(3,4-dimethoxybenzoyl)-1-piperazinyl]-cinnamic acid (12 g) was dissolved in 60 ml of concentrated hydrochloric acid and to the resulting solution was added dropwise a solution of 20 g of stannous chloride in 40 ml of concentrated hydrochloric acid at room temperature. After stirring for 2 hours crystals which precipitated were collected by filtration. The crystals thus-obtained was dissolved in 240 ml of methanol and the solution was neutralized with 10% aqueous sodium hydroxide solution to precipitate crystals, which then were collected by filtration. After concentrating the methanol solution, the residue was recrystallized from ethanol to give 6.3 g of 2-amino-5-[4-(3,4-dimethoxybenzoyl)-1-piperazinyl]cinnamic acid, m.p. 168°–170.5° C., pale yellow powders.

REFERENCE EXAMPLE 9

2-Amino-5-[4-(3,4-dimethoxybenzoyl)-1-piperazinyl]-cinnamic acid (5 g) was dissolved in a mixed solvent consisting of ethanol and water. After adding 5% palladium-carbon (0.5 g), the mixture was reduced at atmospheric pressure of hydrogen gas. After absorption of theoretical amount of hydrogen gas, the catalyst was removed by filtration and the ethanol-water phase was concentrated to dryness. The residue was dissolved in chloroform and separated through silica gel column chromatography to give 1.5 g of 3-{2-amino- 5-[4-(3,4-dimethoxybenzoyl)-1-piperazinyl]phenyl}-propionic acid, m.p. 98°–101° C.

REFERENCE EXAMPLE 10

3-{2-Amino-5-[3,4-dimethoxybenzoyl)-1-piperazinyl]phenyl}propionic acid (4.4 g) was dissolved in acetic acid (40 ml). To this solution was added acetic anhydride (1.1 g) and the mixture was stirred for 1 hour at room temperature. After concentrating acetic acid, water was added to the reaction mixture. Crystals which precipitated were collected by filtration, washed with water and recrystallized from a mixed solvent consisting of acetone and water to give 1.5 g of 3-}2-aminoacetyl-5-[4-(3,4-dimethoxybenzoyl)-1-piperazinyl]-phenyl}propionic acid, m.p. 78.5°–80.5° C.

REFERENCE EXAMPLE 11 o-Nitroaniline (300 g, 2.17 mols) was dissolved in acetic anhydride (620 ml) and stirred at 40°–50° C. for 3 hours. The reaction mixture was poured in ice water. Crystals which formed were collected by filtration and dried. o-Acetylaminonitrobenzene thus-obtained was suspended in methanol (2.4 l). After adding 20 g of 10% palladium-carbon, the suspension was subjected to catalytic reduction at room temperature and atmospheric pressure. After completion of reaction, the catalyst was removed by filtration and the solvent was distilled off under reduced pressure to precipitate crystals which then were washed with ethanol and dried over phosphorus pentoxide under reduced pressure to give 248 g of o-aminoacetanilide.

REFERENCE EXAMPLE 12 o-Acetylaminoaniline (248 g, 1.65 mols) was dissolved in DMF (1 l) and a solution of β-ethoxyacryl chloride (114 g, 0.87 mol) in 0.4 l of DMF was added dropwise to the mixture in 3.5 hours at room temperature while stirring. Then, the resulting mixture was stirred at the same temperature as above for 30 minutes. The reaction mixture was poured into ice water to precipitate crystals, which are collected by filtration to give 84.9 g of 1-acetylamino-2-(β-ethoxyacryloylamido)benzene.

REFERENCE EXAMPLE 13

1-Acetylamino-2-(β-ethoxyacryloylamido)benzene (84.9 g, 0.34 mol) was added portionwise to concentrated sulfuric acid while stirring at room temperature. After completion of addition the mixture was stirred at room temperature for 2 hours. The reaction mixture was poured into a large amount of ice water to precipitate crystals, which were collected by filtration to give 49.5 g of 8-acetylaminocarbostyril.

REFERENCE EXAMPLE 14

8-Acetylaminocarbostyril (15.0 g, 74.2 mols) was suspended in 300 ml of dioxane. After adding 2.0 g of 10% palladium-carbon, the suspension was subjected to catalytic reduction at 70° to 80° C. under atmospheric pressure. After completion of reaction, the catalyst was removed by filtration and the solvent was distilled off under reduced pressure to give 14.3 g of 8-acetylamino-3,4-dihydrocarbostyril.

REFERENCE EXAMPLE 15

8-Acetylamino-3,4-dihydrocarbostyril (11.8 g, 57.8 mols) was suspended in 90 ml of 20% hydrochloric acid and the suspension was stirred while heating under reflux for 1 hours. The reaction mixture was poured into ice water and neutralized with 5 N sodium hydroxide followed by adjusting to pH of about 8. Crystals which precipitated were collected by filtration to give 7.87 g of 8-amino-3,4-dihydrocarbostyril.

REFERENCE EXAMPLE 16

8-Acetylaminocarbostyril (21.5 g, 0.106 mol) was suspended in 190 ml of 20% hydrochloric acid and the suspension was stirred while heating under reflux for 1 hour. The reaction mixture was poured into ice water and neutralized with 5 N sodium hydroxide. Crystals which formed were collected by filtration to give 15.47 g of 8-aminocarbostyril.

EXAMPLE 1

A mixture of 9.36 g of 6-amino-3,4-dihydrocarbostyril, 18 g of bis(β-bromoethyl)amine monohydrobromide and 70 ml of methanol was refluxed for 15 hours while stirring. After cooling, 3.06 g of sodium carbonate was added and the resulting mixture was refluxed for 8 hours while stirring. The reaction mixture was cooled to precipitate crystals which then were collected by filtration, the crystals were washed with methanol to give 9.1 g of 6-(1-piperazinyl)-3,4-dihydrocarbostyril hydrobromide, m.p. 289°-293° C. (decomp.) (methanol-water), colorless needles.

Elemental Analysis for

|  | C | H | N |
|---|---|---|---|
| Calc'd (%) | 50.00 | 5.77 | 13.46 |
| Found (%) | 49.95 | 5.82 | 13.50 |

EXAMPLE 2

In an analogous manner as in Example 1 was obtained 5-(1-piperazinyl)-3,4-dihydrocarbostyril monohydrochloride monohydrate, m.p. above 300° C. (methanol), colorless needles.

EXAMPLE 3

A mixture of 9.36 g of 6-amino-3,4-dihydrocarbostyril, 18.3 g of N,N-(di-β-bromoethyl)-3,4-dimethoxybenzamide and 70 ml of methanol was refluxed for 15 hours while stirring. After cooling 3.06 g of potassium carbonate was added and the mixture was refluxed for 8 hours while stirring. The reaction mixture was cooled to precipitate crystals which then were collected by filtration. Recrystallization from ethanol-chloroform gave 8.5 g of 6-[4-(3,4-dimethoxybenzoyl)-1-piperazinyl]-3,4-dihydrocarbostyril, m.p. 238°-239.5° C., colorless granules.

Elemental Analysis for

|  | C | H | N |
|---|---|---|---|
| Calc'd (%) | 66.84 | 6.33 | 10.63 |
| Found (%) | 66.71 | 6.51 | 10.52 |

EXAMPLES 4–48

In an analogous manner as in Example 3, the following compounds were prepared using appropriate starting materials.

EXAMPLE 4

6-[4-(4-Methoxybenzyl)-1-piperazinyl]3,4-dihydrocarbostyril, m.p. 196°-198° C. (ethanol), colorless needles.

EXAMPLE 5

5-[4-(p-Toluenesulfonyl)-1-piperazinyl]-3,4-dihydrocarbostyril, m.p. 302°-304° C. (dimethylformamide), colorless powder.

EXAMPLE 6

6-(4-Butyl-1-piperazinyl)3,4-dihydrocarbostyril monohydrochloride hemihydrate, m.p. 279°-281° C. (decomp.) (methanol).

EXAMPLE 7

5-(4-Benzoyl-1-piperazinyl)-3,4-dihydrocarbostyril, m.p. 248°-251° C. (ethanol), colorless needles.

EXAMPLE 8

6-(4-Benzoyl-1-piperazinyl)-3,4-dihydrocarbostyril, m.p. 221°-22.5° C. (ethanol), pale yellow granules.

EXAMPLE 9

5-[4-(3,4-dimethoxybenzoyl)-1-piperazinyl]-3,4-dihydrocarbostyril, m.p. 207°-208° C. (ethanol), colorless powder.

EXAMPLE 10

5-[4-(3,4,5-Trimethoxybenzoyl)-1-piperazinyl]-3,4-dihydrocarbostyril, m.p. 250°-251.5° C. (isopropanol), colorless granules.

EXAMPLE 11

6-[4-(3,4,5-Trimethoxybenzoyl)-1-piperazinyl]-3,4-dihydrocarbostyril, m.p. 180°-182° C. (isopropanol), colorless granules.

EXAMPLE 12

6-[4-(4-Methoxybenzoyl)-1-piperazinyl]-3,4-dihydrocarbostyril hemihydrate, m.p. 212°-213° C. (methanol), colorless needles.

EXAMPLE 13

6-(4-Acetyl-1-piperazinyl)-3,4-dihydrocarbostyril, m.p. 203°-205° C. (isopropanol), pale yellowish brown needles.

EXAMPLE 14

6-(4-Furoyl-1-piperazinyl)-3,4-dihydrocarbostyril, m.p. 206.5°-207.5° C. (ethanol), pale yellow granules.

EXAMPLE 15

6-[4-(2-Propynyl)-1-piperazinyl]-3,4-dihydrocarbostyril, m.p. 174°-176° C. (isopropanol).

EXAMPLE 16

6-[4-(4-Chlorobenzoyl)-1-piperazinyl]-3,4,-dihydrocarbostyril, m.p. 233°-235° C., pale yellow needles, (methanol).

EXAMPLE 17

5-[4-(3,4-Dichlorobenzoyl)-1-piperazinyl]-3,4-dihydrocarbostyril, m.p. 250°-252° C. (methanol), colorless powders.

EXAMPLE 18

5-[4-(3,5-Dichlorobenzoyl)-1-piperazinyl]-3,4-dihydrocarbostyril, m.p. 255°-257° C. (methanol-chloroform), colorless needles.

EXAMPLE 19

6-[4-(4-Bromobenzoyl)-1-piperazinyl]-3,4-dihydrocarbostyril, m.p. 233°-234.5° C., colorless granules, (methanol-chloroform).

EXAMPLE 20

5-[4-(4-Cyanobenzoyl)-1-piperazinyl]-3,4-dihydrocarbostyril, m.p. 266°-269° C., colorless granules, methanol-chloroform).

EXAMPLE 21

6-[4-(4-Nitrobenzoyl)-1-piperazinyl]-3,4-dihydrocarbostyril, m.p. 235.5°-236.5° C. (methanol-chloroform), yellow scales.

EXAMPLE 22

6-[4-(3,5-Dinitrobenzoyl)-1-piperazinyl]-3,4-dihydrocarbostyril, m.p. 262°-264° C. (methanol-chloroform), reddish black needles.

EXAMPLE 23

6-[4-(4-Aminobenzoyl)-1-piperazinyl]-3,4-dihydrocarbostyril, m.p. 244°-246° C., pale yellow needles (ethanol).

EXAMPLE 24

5-[4-(4-Hydroxybenzoyl)-1-piperazinyl]-3,4-dihydrocarbostyril, m.p. above 300° C. (methanol-chloroform), colorless granules.

EXAMPLE 25

6-[4-(3,4-Methylenedioxybenzoyl)-1-piperazinyl]-3,4-dihydrocarbostyril, m.p. 191°-192.5° C. (methanol), colorless needles.

EXAMPLE 26

5-[4-(4-Methylbenzoyl)-1-piperazinyl]-3,4-dihydrocarbostyril, m.p. 239.5°-240° C. (chloroform-ether), colorless powders.

EXAMPLE 27

6-[4-(Methanesulfonyl)-1-piperazinyl]-3,4-dihydrocarbostyril, m.p. 241.5°-243° C., colorless granules (methanol).

EXAMPLE 28

5-(4-Ethyl-1-piperazinyl)-3,4-dihydrocarbostyril monohydrochloride, m.p. 293°-296° C. (decomp.) (methanol), colorless granules.

EXAMPLE 29

6-(4-Allyl-1-piperazinyl)-3,4-dihydrocarbostyril, m.p. 175°-176° C. (chloroform-ether), colorless scales.

EXAMPLE 30

5-[4-(2-Propynyl)-1-piperazinyl]-3,4-dihydrocarbostyril, m.p. 225°-226° C. (chloroform), pale yellow powders.

EXAMPLE 31

6-[4-(2-Butenyl)-1-piperazinyl]-3,4-dihydrocarbostyril, m.p. 242°-245° C. (decomp.).

EXAMPLE 32

1-Benzyl-6-[4-(3,4-dimethoxybenzoyl)-1-piperazinyl]-3,4-dihydrocarbostyril hemihydrate, m.p. 131.5°-132.5° C. (ethanol), yellow powders.

EXAMPLE 33

1-Allyl-5-[4-(3,4-dimethoxybenzoyl)-1-piperazinyl]-3,4-dihydrocarbostyril hemihydrate, m.p. 120°-122° C. (methanol-ether), colorless granules.

EXAMPLE 34

1-(2-Propynyl)-6-[4-(3,4-dimethoxybenzoyl)-1-piperazinyl]-3,4-dihydrocarbostyril, m.p. 152°-154° C. (ethanol), pale yellow needles.

EXAMPLE 35

1-Methyl-6-[4-(3,4-dimethoxybenzoyl)-1-piperazinyl]-3,4-dihydrocarbostyril, m.p. 146.5°-147.5° C. (isopropanol), pale yellow granules.

EXAMPLE 36

8-Methoxy-6-[4-(3,4-dimethoxybenzoyl)-1-piperazinyl]-3,4-dihydrocarbostyril, m.p. 162.5°-163.5° C. (isopropanol), colorless needles.

EXAMPLE 37

6-[4-(3-Chlorobenzoyl)-1-piperazinyl]-3,4-dihydrocarbostyril, m.p. 195°-197.5° C., colorless scales (methanol).

EXAMPLE 38

5-[4-(4-Methoxybenzoyl)-1-piperazinyl]-3,4-dihydrocarbostyril, m.p. 219°-220° C. (methanol-chloroform), colorless needles.

EXAMPLE 39

5-(4-Ethoxycarbonylmethyl-1-piperazinyl)-3,4-dihydrocarbostyril, m.p. 206°-208° C. (methanol), colorless needles.

EXAMPLE 40

5-[4-(4-Formyl)-1-piperazinyl]-3,4-dihydrocarbostyril, m.p. 263°-265° C., colorless granules (methanol).

EXAMPLE 41

6-(4-Ethoxycarbonyl-1-piperazinyl)-3,4-dihydrocarbostyril, m.p. 182.5°–184° C., colorless needles (isopropanol).

EXAMPLE 42

5-[4-(4-Methoxybenzyl)-1-piperazinyl]-3,4-dihydrocarbostyril, m.p. 194°–196° C. (methanol), colorless needles.

EXAMPLE 43

6-[4-(2-Phenethyl)-1-piperazinyl]-3,4-dihydrocarbostyril monohydrochloride, m.p. 274°–276° C. (decomp.) (methanol), colorless powders.

EXAMPLE 44

4-[4-(4-Chlorobenzyl)-1-piperazinyl]-3,4-dihydrocarbostyril, m.p. 190°–191.5° C. (chloroform-methanol), colorless needles.

EXAMPLE 45

5-[4-(3,4-Dichlorobenzyl)-1-piperazinyl]-3,4-dihydrocarbostyril monohydrochloride monohydrate, m.p. 298.5°–300° C. (decomp.) (methanol), colorless granules.

EXAMPLE 46

5-[4-Nitrobenzyl)-1-piperazinyl]-3,4-dihydrocarbostyril, m.p. 268°–271° C. (decomp.) (methanol), pale yellow powders.

EXAMPLE 47

5-[4-(4-Aminobenzyl)-1-piperazinyl]-3,4-dihydrocarbostyril dihydrochloride monohydrate, m.p. 224°–227° C. (decomp.) (methanol-ether), yellow granules.

EXAMPLE 48

6-[4-(4-Methylbenzyl)-1-piperazinyl]-3,4-dihydrocarbostyril dihydrochloride, m.p. 272°–273° C. (decomp.) (methanol-water), colorless powders.

EXAMPLE 49

5-[4-(3,4-Dimethoxybenzyl)-1-piperazinyl]-3,4-dihydrocarbostyril dihydrochloride, m.p. 270°–272.5° C. (decomp.).

EXAMPLE 50

6-(4-Ethoxycarbonyl-1-piperazinyl)carbostyril, m.p. 223°–224° C. (methanol), yellow needles.

EXAMPLE 51

6-[4-(3-Chlorobenzoyl)-1-piperazinyl]carbostyril, m.p. 250.5°–252° C. (methanol-chloroform), yellow powders.

EXAMPLE 52

6-[4-(4-Chlorobenzoyl)-1-piperazinyl]carbostyril, m.p. 265°–266° C. (methanol-chloroform), yellow powders.

EXAMPLE 53

6-[4-(4-Methoxybenzoyl)-1-piperazinyl]carbostyril, m.p. 230°–233° C. (methanol-chloroform), yellow needles.

EXAMPLE 54

6-[4-(3,4-Dimethoxybenzoyl)-1-piperazinyl]-carbostyril, m.p. 265°–266.5° C. (decomp.) (methanol-chloroform), yellow granules.

EXAMPLE 55

6-[4-(3,4,5-Trimethoxybenzoyl)-1-piperazinyl]-carbostyril, m.p. 249.5°–250° C. (methanol-chloroform), yellow needles.

EXAMPLE 56

6-[4-(4-Cyanobenzoyl)-1-piperazinyl]carbostyril, m.p. 300°–301° C. (decomp.) (ethanol-chloroform), yellow powders.

EXAMPLE 57

6-[4-(3,4-Methylenedioxybenzoyl)-1-piperazinyl]-carbostyril, m.p. 266°–267° C. (decomp.) (methanol-chloroform), yellow powders.

EXAMPLE 58

6-[4-(4-Nitrobenzoyl)-1-piperazinyl]carbostyril, m.p. 265°–266° C. (decomp.) (methanol-chloroform), yellow needles.

EXAMPLE 59

6-[4-(4-Aminobenzoyl)-1-piperazinyl]carbostyril, m.p. 287°–290° C. (chloroform-methanol), yellow powders.

EXAMPLE 60

6-(4-Benzoyl-1-piperazinyl)carbostyril, m.p. 264°–265° C. (ethanol-chloroform), yellow needles.

EXAMPLE 61

5-[4-(4-Acetylaminobenzoyl)-1-piperazinyl]-3,4-dihydrocarbostyril, m.p. above 300° C. (chloroform-methanol), colorless powders

EXAMPLE 62

6-[4-(4-Formyl)-1-piperazinyl]carbostyril, m.p. 286.5°–288° C. (methanol), yellow scales.

EXAMPLE 63

6-[4-(4-Methylthiobenzoyl)-1-piperazinyl]-carbostyril, m.p. 247.5°–249.5° C. (chloroform-methanol), yellow needles.

EXAMPLE 64

6-[4-(3-Pyridylcarbonyl-1-piperazinyl]-3,4-dihydrocarbostyril, m.p. 250°–252° C. (ethanol), yellow needles.

EXAMPLE 65

6-[4-(4-Methoxyphenylacetyl)-1-piperazinyl]-3,4-dihydrocarbostyril, m.p. 266°–268.5° C. (methanol), yellow powders.

EXAMPLE 66

6-(4-Phenylpropionyl-1-piperazinyl)-3,4-dihydrocarbostyril, m.p. 189.5°–191° C. (chloroform-methanol), yellow granules.

EXAMPLE 67

8-(4-Benzoyl-1-piperazinyl)carbostyril, m.p. 244°–245° C. (ethanol), colorless powders.

EXAMPLE 68

8-[4-(4-Chlorobenzoyl)-1-piperazinyl]carbostyril, m.p. 255.5°-257° C. (ethanol-chloroform), colorless powders.

EXAMPLE 69

8-[4-(3-Chlorobenzoyl)-1-piperazinyl]carbostyril, m.p. 208°-209° C. (ethanol), colorless granules.

EXAMPLE 70

8-[4-(2-Chlorobenzoyl)-1-piperazinyl]carbostyril, m.p. 239°-240.5° C. (ethanol), colorless needles.

EXAMPLE 71

8-[4-(4-Methoxybenzoyl)-1-piperazinyl]carbostyril, m.p. 208°-210° C. (ethanol), colorless scales.

EXAMPLE 72

8-[4-(3,4-Dimethoxybenzoyl)-1-piperazinyl]carbostyril, m.p. 197°-198° C. (ethanol-ether), colorless scales.

EXAMPLE 73

8-[4-(3,4-Methylenedioxybenzoyl)-1-piperazinyl]-3,4-dihydrocarbostyril, m.p. 195°-197° C. (ethanol), colorless scales.

EXAMPLE 74

8-[4-(3-Chlorobenzoyl)-1-piperazinyl]-3,4-dihydrocarbostyril, m.p. 152°-154° C. (ethanol), colorless scales.

EXAMPLE 75

8-[4-(3,4-Dimethoxybenzoyl)-1-piperazinyl]-3,4-dihydrocarbostyril, m.p. 145°-148° C., colorless scales, (ethanol).

EXAMPLE 76

8-[4-(4-Methylthiobenzoyl)-1-piperazinyl]-3,4-dihydrocarbostyril, m.p. 178°-179.5° C., colorless granules, (ethanol).

EXAMPLE 77

7-[4-(2-Chlorobenzoyl)-1-piperazinyl]-3,4-dihydrocarbostyril, m.p. 194°-195.5° C. (methanol), colorless needles.

EXAMPLE 78

7-[4-(3-Chlorobenzoyl)-1-piperazinyl]-3,4-dihydrocarbostyril, m.p. 136.5°-138.5° C. (ethanol), colorless powders.

EXAMPLE 79

7-[4-(4-Chlorobenzoyl)-1-piperazinyl]-3,4-dihydrocarbostyril, m.p. 289°-291° C., colorless powders, (chloroform-methanol).

EXAMPLE 80

7-[4-(4-Methoxybenzoyl)-1-piperazinyl]-3,4-dihydrocarbostyril, m.p. 231°-233° C., colorless needles, (ethanol).

EXAMPLE 81

7-[4-(3,4-Methylenedioxybenzoyl)-1-piperazinyl]-3,4-dihydrocarbostyril, m.p. 207°-208° C. (ethanol), colorless powders.

EXAMPLE 82

7-[4-(4-Nitrobenzoyl)-1-piperazinyl]-3,4-dihydrocarbostyril, m.p. 240°-242° C. (chloroform-methanol), yellow granules.

EXAMPLE 83

7-[4-(3,4,5-Trimethoxybenzoyl)-1-piperazinyl]-3,4-dihydrocarbostyril, m.p. 195°-196.5° C. (methanol), colorless rhombic crystals.

EXAMPLE 84

7-(4-Benzoyl-1-piperazinyl)-3,4-dihydrocarbostyril, m.p. 264.5°-265.5° C. (chloroform-methanol), colorless needles.

EXAMPLE 85

7-[4-(3,4-Dimethoxybenzoyl)-1-piperazinyl]-3,4-dihydrocarbostyril, m.p. 118°-120° C. (ethanol; dried under reduced pressure at 80° C. for 5 hours), colorless granules.

EXAMPLE 86

7-[4-(4-Methylthiobenzoyl)-1-piperazinyl]-3,4-dihydrocarbostyril, m.p. 258°-260° C. (chloroform-methanol), colorless rhombic crystals.

EXAMPLE 87

7-(4-Phenylpropionyl-1-piperazinyl)-3,4-dihydrocarbostyril, m.p. 183°-184° C., colorless needles (ethanol).

EXAMPLE 88

6-[4-(4-Methoxyphenylacetyl)-1-piperazinyl]-carbostyril, m.p. 224°-225° C. (ethanol), yellow needles.

EXAMPLE 89

6-[4-(4-Hydroxyphenylacetyl)-1-piperazinyl]-carbostyril, m.p. above 300° C. (DMF), yellow powders.

EXAMPLE 90

5-[4-(4-Nitrobenzoyl)-1-piperazinyl]-3,4-dihydrocarbostyril, m.p. 292°-294° C. (decomp) (methanol-chloroform), yellow granules.

EXAMPLE 91

5-[4-(4-Aminobenzoyl)-1-piperazinyl]-3,4-dihydrocarbostyril.

EXAMPLE 92

6-(1-Piperazinyl)-3,4-dihydrocarbostyril monohydrobromide (3.5 g) was suspended in 40 ml of dimethylformamide (hereafter referred to as DMF for brevity). After adding 960 mg of sodium hydrogencarbonate, the suspension was stirred at room temperature for 30 minutes to convert the starting compound to 6-(1-piperazinyl)-3,4-dihydrocarbostyril. Then, to the mixture was added 2.34 ml of triethylamine and the mixture was stirred at room temperature while slowly adding dropwise 10 ml of DMF solution containing 2.9 g of 3,4-dimethoxybenzoyl chloride. After completion of addition the reaction mixture was stirred for 30 minutes. The reaction mixture was poured into a large amount of saturated saline solution and extracted with chloroform. The extract was washed with saturated sodium hydrogen carbonate solution and subsequently with water and dried over anhydrous sodium sulfate. Chloroform was distilled off and residual crystals were recrystallized from chloroform-ethanol to give 3.8 g of 6-[4-(3,4-dimethoxybenzoyl)-1-piperazinyl]-3,4-dihydrocarbostyril, m.p. 238°-239.5° C., colorless granules.

Elemental Analysis for

|  | C | H | N |
|---|---|---|---|
| Calc'd (%) | 66.84 | 6.33 | 10.63 |
| Found (%) | 66.69 | 6.49 | 10.51 |

In an analogous manner as in Example 92, the same compounds as those obtained in Examples 7-14, 32-36, 41, 50-61 and 63-91 were prepared using appropriate starting materials.

EXAMPLE 93

6-(1-Piperazinyl)-3,4-dihydrocarbostyril monohydrobromide (1 g) was suspended in 15 ml of DMF. After adding 296 mg of sodium hydrogencarbonate, the suspension was stirred at room temperature for 30 minutes to convert the starting compound to 6-(1-piperazinyl)-3,4-dihydrocarbostyril. Then, to the mixture was added 0.62 ml of triethylamine and the mixture was stirred at room temperature while slowly adding dropwise 5 ml of DMF solution containing 532 mg of m-chlorobenzoyl chloride. After completion of addition the reaction mixture was stirred for at room temperature 1 hour. The reaction mixture was poured into a large amount of water and extracted with chloroform. The extract was washed with saturated sodium hydrogencarbonate solution and subsequently with water and dried over anhydrous sodium sulfate. Chloroform was distilled off and residual crystals were recrystallized from methanol to give 0.4 g of 6-[4-(3-chlorobenzoyl)-1-piperazinyl]-3,4-dihydrocarbostyril, m.p. 197°-197.5° C., colorless scales.

Elemental Analysis for

|  | C | H | N |
|---|---|---|---|
| Calc'd (%) | 65.04 | 5.42 | 11.38 |
| Found (%) | 64.99 | 5.35 | 11.45 |

EXAMPLE 94

6-(1-Piperazinyl)-3,4-dihydrocarbostyril monohydrobromide (3.5 g) was suspended in 40 ml of DMF. After adding 960 mg of sodium hydrogencarbonate, the suspension was stirred at room temperature for 30 minutes to convert the starting compound to 6-(1-piperazinyl)-3,4-dihydrocarbostyril. Then, to the mixture was added 2.34 ml of triethylamine and the mixture was stirred at room temperature while slowly adding dropwise 10 ml of DMF solution containing 2.5 g of 4-chlorobenzoyl chloride. After completion of addition the reaction mixture was stirred for 30 minutes. The reaction mixture was poured into a large amount of water and extracted with chloroform. The extract was washed with saturated sodium hydrogen carbonate solution and subsequently with water and dried over anhydrous sodium sulfate. Chloroform was distilled off and residual crystals were recrystallized from methanol to give 0.7 g of 6-[4-(4-chlorobenzoyl)-1-piperazinyl]-3,4-dihydrocarbostyril, m.p. 233°-235° C., pale yellow needles.

Elemental Analysis for

|  | C | H | N |
|---|---|---|---|
| Calc'd (%) | 65.04 | 5.42 | 11.38 |
| Found (%) | 64.89 | 5.30 | 11.51 |

EXAMPLE 95

5-(1-Piperazinyl)-3,4-dihydrocarbostyril monohydrobromide (2.6 g) and 2.34 ml of triethylamine were dissolved in 40 ml of DMF. The mixture was stirred at room temperature while slowly adding dropwise 10 ml of DMF solution containing 2.5 g of 4-methoxybenzoyl chloride. After completion of addition the reaction mixture was stirred for 30 minutes. The reaction mixture was poured into a large amount of water and extracted with chloroform. The extract was washed with saturated sodium hydrogencarbonate solution and subsequently with water and dried over anhydrous sodium sulfate. Chloroform was distilled off and residual crystals were recrystallized from methanol-chloroform to give 1.1 g of 5-[4-(4-methoxybenzoyl)-1-piperazinyl]-3,4-dihydrocarbostyril, m.p. 219°-220° C., colorless needles.

Elemental Analysis for

|  | C | H | N |
|---|---|---|---|
| Calc'd (%) | 69.04 | 6.30 | 13.15 |
| Found (%) | 68.95 | 6.21 | 13.24 |

EXAMPLE 96

5-(1-Piperazinyl)-3,4-dihydrocarbostyril monohydrobromide (3.5 g) was suspended in 40 ml DMF. After adding 960 mg of sodium hydrogencarbonate, the suspension was stirred at room temperature for 30 minutes to convert the starting compound to 5-(1-piperazinyl)-3,4-dihydrocarbostyril. Then, to the mixture was added 2.34 ml of triethylamine and the mixture was stirred at room temperature while slowly adding dropwise 10 ml of DMF solution containing 3.0 g of 3,5-dichlorobenzoyl chloride. After completion of addition the reaction mixture was stirred for 40 minutes. The reaction mixture was poured into a large amount of saturated saline solution and extracted with chloroform. The extract was washed with saturated sodium hydrogencarbonate solution and subsequently with water and dried over anhydrous sodium sulfate. Chloroform was distilled off and residual crystals were recrystallized from methanol-chloroform to give 1.8 g of 5-[4-(3,5-dichlorobenzoyl)-1-piperazinyl]-3,4-dihydrocarbostyril, m.p. 255°-257° C., colorless needles.

Elemental Analysis for

|  | C | H | N |
|---|---|---|---|
| Calc'd (%) | 59.55 | 4.71 | 10.42 |
| Found (%) | 59.43 | 4.83 | 10.31 |

EXAMPLE 97

6-(1-Piperazinyl)-3,4-dihydrocarbostyril (2.6 g) and 1 g of sodium hydrogencarbonate was added to 50 ml of dimethyl sulfoxide and the mixture was stirred with ice cooling while slowly adding dropwise 20 ml of dimethyl sulfoxide solution containing 3.2 g of 4-bromobenzoyl chloride. After completion of addition the reaction mixture was stirred at room temperature for 60 minutes. The reaction mixture was poured into a large amount of water and extracted with chloroform. The extract was washed with saturated sodium hydrogencarbonate solution and subsequently with water and dried over anhydrous sodium sulfate. Chloroform was distilled off and residual crystals were recrystallized from methanol-chloroform to give 0.8 g of 6-[4-(4-bromobenzoyl)-1-piperazinyl]-3,4-dihydrocarbostyril, m.p. 233°–234.5° C., colorless granules.

Elemental Analysis for

|  | C | H | N |
|---|---|---|---|
| Calc'd (%) | 57.97 | 4.83 | 10.14 |
| Found (%) | 57.79 | 4.71 | 10.23 |

EXAMPLE 98

5-(1-Piperazinyl)-3,4-dihydrocarbostyril (2.6 g) and 2 ml of trimethylamine were added to 40 ml of DMF. The mixture was stirred at room temperature while slowly adding dropwise 10 ml of DMF solution containing 2.4 g of 4-cyanobenzoyl chloride. After completion of addition, the reaction mixture was stirred at 40° to 50° C. for 30 minutes. The reaction mixture was poured into a large amount of water and extracted with chloroform. The extract was washed with sodium hydrogencarbonate solution and subsequently with water and dried over anhydrous sodium sulfate. Chloroform was distilled off and residual crystals were recrystallized from methanol-chloroform to give 1.9 g of 5-[4-(4-cyanobenzoyl)-1-piperazinyl]-3,4-dihydrocarbostyril, m.p. 266°–269° C., colorless granules.

Elemental Analysis for

|  | C | H | N |
|---|---|---|---|
| Calc'd (%) | 70.00 | 5.56 | 15.56 |
| Found (%) | 70.14 | 5.71 | 15.43 |

EXAMPLE 99

6-(1-Piperazinyl)-3,4-dihydrocarbostyril (2.6 g) and 2 ml of pyridine were added to 40 ml of DMF. The mixture was stirred at room temperature while slowly adding dropwise 10 ml of DMF solution containing 2.7 g of 4-nitrobenzoyl chloride. After completion of addition, the reaction mixture was stirred at the same temperature for 30 minutes. The reaction mixture was poured into a large amount of water and extracted with chloroform. The extract was washed with sodium hydrogencarbonate solution and subsequently with water and dried over anhydrous sodium sulfate. Chloroform was distilled off and residual crystals were recrystallized from methanol-chloroform to give 2.4 g of 6-[4-(4-nitrobenzoyl)-1-piperazinyl]-3,4-dihydrocarbostyril, m.p. 235.5°–236.5° C.

Elemental Analysis for

|  | C | H | N |
|---|---|---|---|
| Calc'd (%) | 63.15 | 5.30 | 14.73 |
| Found (%) | 63.09 | 5.35 | 14.77 |

EXAMPLE 100

6-(1-Piperazinyl)-3,4-dihydrocarbostyril (2.6 g) and 2.34 ml of triethylamine was added to 40 ml of dimethyl sulfoxide and the mixture was stirred at room temperature while slowly adding dropwise 10 ml of dimethyl sulfoxide solution containing 3.3 g of 3,5-dinitrobenzoyl chloride. After completion of addition the reaction mixture was stirred at room temperature for 30 minutes. The reaction mixture was poured into a large amount of water and extracted with chloroform. The extract was washed with saturated sodium hydrogencarbonate solution and subsequently with water and dried over anhydrous sodium sulfate, chloroform was distilled off and residual crystals were recrystallized from methanol-chloroform to give 0.3 g of 6-[4-(3,5-dinitrobenzoyl)-1-piperazinyl]-3,4-dihydrocarbostyril, m.p. 262°–264° C., reddish black needles.

Elemental Analysis for

|  | C | H | N |
|---|---|---|---|
| Calc'd (%) | 56.47 | 4.47 | 16.47 |
| Found (%) | 56.34 | 4.61 | 16.35 |

EXAMPLE 101

6-[4-(4-Nitrobenzoyl)-1-piperazinyl]-3,4-dihydrocarbostyril (400 mg) was added to 20 ml of methanol and reduced at room temperature at atmospheric pressure using 50 mg of 10% palladium-carbon as a catalyst. After completion of absorption of hydrogen gas the catalyst was removed by filtration. The filtrate was subjected to distillation under reduced pressure and the residue was purified through silica gel column chromatography. Recrystallization from ethanol gave 210 mg of 6-[4-(4-aminobenzoyl)-1-piperazinyl]-3,4-dihydrocarbostyril, m.p. 244°–246° C., pale yellow needles.

Elemental Analysis for

|  | C | H | N |
|---|---|---|---|
| Calc'd (%) | 68.57 | 6.29 | 16.00 |
| Found (%) | 68.70 | 6.18 | 16.14 |

In an analogous manner as in Example 101 was prepared 5-[4-(4-aminobenzyl)-1-piperazinyl]-3,4-dihydrocarbostyril dihydrochloride monohydrate, m.p. 224°–227° C. (decomp.), (methanol-ether), yellow granules.

EXAMPLE 102

A mixture of 300 mg of 5-[4-(4-methoxybenzoyl)-1-piperazinyl]-3,4-dihydrocarbostyril and 7 ml of methylene chloride was stirred at 0°–5° C. while slowly adding dropwise 2 ml of methylene chloride solution containing 226 mg of boron tribromide. After completion of addition, the reaction mixture was stirred at the same temperature as above for 30 minutes and the temperature was elevated to room temperature in about 1 hour. Then, the reaction mixture was poured into a large amount of water and crystals which precipitated were collected by filtration. Recrystallization of the crystals from methanol-chloroform gave 150 mg of 5-[4-(4-hydroxybenzoyl)-1-piperazinyl-3,4-dihydrocarbostyril, m.p. above 300° C., colorless granules.

Elemental Analysis for

|           | C     | H     | N     |
|-----------|-------|-------|-------|
| Calc'd (%) | 63.38 | 5.98  | 11.97 |
| Found (%)  | 68.21 | 6.11  | 11.83 |

EXAMPLE 103

5-(1-Piperazinyl)-3,4-dihydrocarbostyril (2.6 g) and 4 ml of DBU were added to 40 ml of DMF. The mixture was stirred at room temperature while slowly adding dropwise 10 ml of DMF solution containing 3.0 g of 3,4-dichlorobenzoyl chloride. After completion of addition, the reaction mixture was stirred for 30 minutes. The reaction mixture was poured into a large amount of water and extracted with chloroform. The extract was washed with sodium hydrogencarbonate solution and subsequently with water and dried over anhydrous sodium sulfate. Chloroform was distilled off and residual crystals were recrystallized from methanol to give 1.2 g of 5-[4-(3,4-dichlorobenzoyl)-1-piperazinyl]-3,4-dihydrocarbostyril, m.p. 250°-252° C., colorless powders.

Elemental Analysis for

|           | C     | H     | N     |
|-----------|-------|-------|-------|
| Calc'd (%) | 59.55 | 4.71  | 10.42 |
| Found (%)  | 59.38 | 4.82  | 10.34 |

EXAMPLE 104

6-(1-Piperazinyl)-3,4-dihydrocarbostyril (2.6 g) and 2.34 ml of triethylamine were added to 40 ml of DMF. The mixture was stirred at room temperature while slowly adding dropwise 10 ml of DMF solution containing 2.7 g of 3,4-methylenedioxybenzoyl chloride. After completion of addition, the reaction mixture was stirred at room temperature for 30 minutes. The reaction mixture was poured into a large amount of water and extracted with chloroform. The extract was washed with sodium hydrogencarbonate solution and subsequently with water and dried over anhydrous sodium sulfate. Chloroform was distilled off and residual crystals were recrystallized from methanol to give 1.6 g of 6-[4-(3,4-methylenedioxybenzoyl)-1-piperazinyl]-3,4-dihydrocarbostyril, m.p. 191°-192.5° C., colorless needles.

Elemental Analysis for

|           | C     | H     | N     |
|-----------|-------|-------|-------|
| Calc'd (%) | 66.49 | 5.54  | 11.08 |
| Found (%)  | 66.35 | 5.67  | 10.94 |

EXAMPLE 105

5-(1-Piperazinyl)-3,4-dihydrocarbostyril (2.6 g) and 2.34 ml of triethylamine were added to 50 ml of chloroform. The mixture was stirred at room temperature while slowly adding dropwise 10 ml of chloroform solution containing 2.3 g of 4-methylbenzoyl chloride. After completion of addition, the reaction mixture was stirred for 30 minutes. After completion of reaction, 100 ml of chloroform and then a large amount of water was added to separate chloroform and the chloroform layer was washed with sodium hydrogencarbonate solution and subsequently with water and dried over anhydrous sodium sulfate. Chloroform was distilled off and residual crystals were recrystallized from chloroformether to give 1.8 g of 5-[4-(4-methylbenzoyl)-1-piperazinyl]-3,4-dihydrocarbostyril, m.p. 239.5°-240° C., colorless powders.

Elemental Analysis for

|           | C     | H     | N     |
|-----------|-------|-------|-------|
| Calc'd (%) | 72.21 | 6.59  | 12.03 |
| Found (%)  | 72.34 | 6.44  | 11.94 |

EXAMPLE 106

To a mixture of 1.2 g of 6-(1-piperazinyl)-3,4-dihydrocarbostyril, 1.17 g of potassium carbonate and 20 ml of DMF was added 720 mg of 4-methoxybenzyl chloride and the mixture was stirred at 80° C. for 2.5 hours. The reaction mixture was poured into a large amount of saturated saline solution and extracted with chloroform. After washing with water the extract was dried over anhydrous sodium sulfate. Chloroform was distilled off and the residue was purified through silica gel column chromatography. Recrystallization from ethanol gave 950 mg of 6-[4-(4-methoxybenzyl)-1-piperazinyl]-3,4-dihydrocarbostyril, m.p. 196°-198° C., colorless needles.

Elemental Analysis for

|           | C     | H     | N     |
|-----------|-------|-------|-------|
| Calc'd (%) | 70.00 | 7.22  | 11.67 |
| Found (%)  | 69.91 | 7.15  | 11.71 |

In an analogous manner as in Example 106, the same compound as that obtained in Example 44 was prepared using appropriate starting materials.

EXAMPLE 107

A mixture of 1.0 g of 5-(1-piperazinyl)-3,4-dihydrocarbostyril, 1.11 g of potassium carbonate, 760 mg of 4-methoxybenzyl chloride and 20 ml of DMF was stirred at 70°-80° C. for 4 hours. The reaction mixture was poured into a large amount of water and extracted with chloroform. After washing with water the extract was dried over anhydrous sodium sulfate. Chloroform was distilled off and the residue was purified through silica gel column chromatography. Recrystallization from methanol gave 60 mg of 5-[4-(4-methoxybenzyl)-1-piperazinyl]-3,4-dihydrocarbostyril, m.p. 194°-196° C., colorless needles.

Elemental Analysis for

|           | C     | H     | N     |
|-----------|-------|-------|-------|
| Calc'd (%) | 71.79 | 7.12  | 11.97 |
| Found (%)  | 71.84 | 7.05  | 11.89 |

EXAMPLE 108

To a mixture of 1.2 g of 6-(1-piperazinyl)-3,4-dihydrocarbostyril, 1.17 g of potassium carbonate and 20 ml of DMF was added 646 mg of 2-phenethyl chloride and the mixture was stirred at 80°-100° C. for 2.5 hours. The reaction mixture was poured into a large amount of water and extracted with chloroform. After washing with water the extract was dried over anhydrous sodium sulfate. Chloroform was distilled off and the residue was purified through silica gel column chromatography. After conversion to hydrochloric acid salt with methanol-hydrochloric acid, the product was recrystallized from methanol to give 0.6 g of 6-[4-(2-phenethyl)-1-piperazinyl]-3,4- dihydrocarbostyril hydrochloride, m.p. 274°–276° C. (decomp.), colorless powders.

Elemental Analysis for

|  | C | H | N |
|---|---|---|---|
| Calc'd (%) | 67.82 | 7.05 | 11.30 |
| Found (%) | 67.85 | 6.93 | 11.39 |

EXAMPLE 109

To a mixture of 1.2 g of 5-(1-piperazinyl)-3,4-dihydrocarbostyril, 1.17 g of potassium carbonate and 20 ml of DMF was added 858 mg of 3,4-dimethoxybenzyl chloride and the mixture was stirred at 70°–80° C. for 2 hours. The reaction mixture was poured into a large amount of water and extracted with chloroform. After washing with water the extract was dried over anhydrous sodium sulfate. Chloroform was distilled off and the residue was purified through silica gel column chromatography. The residue was converted to hydrochloric acid salt to give 610 mg of 5-[4-(3,4-dimethoxybenzyl)-1-piperazinyl]-3,4-dihydrocarbostyril dihydrochloride, m.p. 270°–272.5° C. (decomp.).

Elemental Analysis for

|  | C | H | N |
|---|---|---|---|
| Calc'd (%) | 58.15 | 6.43 | 9.25 |
| Found (%) | 58.08 | 6.51 | 9.14 |

EXAMPLE 110

To a mixture of 1.0 g of 6-(1-piperazinyl)-3,4-dihydrocarbostyril, 1.11 g of potassium carbonate and 20 ml of DMF was added 780 mg of 4-chlorobenzyl chloride and the mixture was stirred at 70°–80° C. for 4 hours. The reaction mixture was poured into a large amount of water and extracted with chloroform. Chloroform was distilled off and the residue was purified through silica gel column chromatography. Recrystallization from chloroform-methanol gave 500 mg of 6-[4-(4-chlorobenzyl)-1-piperazinyl]-3,4-dihydrocarbostyril, m.p. 190°–191.5° C., colorless needles.

Elemental Analysis for

|  | C | H | N |
|---|---|---|---|
| Calc'd (%) | 67.51 | 6.23 | 11.81 |
| Found (%) | 67.31 | 6.17 | 11.85 |

EXAMPLE 111

To a mixture of 1.2 g of 5-(1-piperazinyl)-3,4-dihydrocarbostyril, 1.17 g of potassium carbonate and 20 ml of DMF was added 895 mg of 3,4-dichlorobenzyl chloride and the mixture was stirred at 60°–70° C. for 3 hours. The reaction mixture was poured into a large amount of water and extracted with chloroform. After washing with water the extract was dried over anhydrous sodium sulfate. Chloroform was distilled off and the residue was purified through silica gel column chromatography. After conversion to hydrochloric acid salt with methanol-hydrochloric acid the product was recrystallized from methanol to give 0.17 g of 5-[4-(3,4-dichlorobenzyl)-1-piperazinyl]-3,4-dihydrocarbostyril monohydrochloride monohydrate, m.p. 298.5°–300° C. (decomp.), colorless granules.

Elemental Analysis for

|  | C | H | N |
|---|---|---|---|
| Calc'd (%) | 54.00 | 5.44 | 9.45 |
| Found (%) | 53.73 | 5.57 | 9.29 |

EXAMPLE 112

To a mixture of 1.2 g of 6-(1-piperazinyl)-3,4-dihydrocarbostyril, 1.17 g of potassium carbonate and 50 ml of benzene was added 789 mg of 4-nitrobenzyl chloride and the mixture was stirred under reflux for 4 hours. After completion of reaction benzene was distilled off and the residue was dissolved in chloroform. The chloroform layer was washed with water and dried over anhydrous sodium sulfate. Chloroform was distilled off and the residue was purified through silica gel column chromatography. Recrystallization from chloroform-ether gave 0.26 g of 5-[4-(4-nitrobenzyl)-1-piperazinyl]-3,4-dihydrocarbostyril, m.p. 268°–271° C. (decomp.), pale yellow powders.

Elemental Analysis for

|  | C | H | N |
|---|---|---|---|
| Calc'd (%) | 65.57 | 6.01 | 15.30 |
| Found (%) | 65.43 | 5.89 | 15.42 |

EXAMPLE 113

To a mixture of 1.2 g of 5-(1-piperazinyl)-3,4-dihydrocarbostyril, 1.17 g of potassium carbonate and 20 ml of dimethyl sulfoxide was added 650 mg of 4-aminobenzyl chloride and the mixture was stirred at 80° C. for 2.5 hours. The reaction mixture was poured into a large amount of water and extracted with chloroform. After washing with water, the extract was dried over anhydrous sodium sulfate. Chloroform was distilled off and the residue was purified through silica gel column chromatography. After conversion to hydrochloric acid salt with methanol-hydrochloric acid, the product was recrystallized from methanol-ether to give 0.4 g of 5-[4-(4-aminobenzyl)-1-piperazinyl]-3,4-dihydrocarbostyril dihydrochloride monohydrate, m.p. 224°–227° C. (decomp.), yellow granules.

Elemental Analysis for

|  | C | H | N |
|---|---|---|---|
| Calc'd (%) | 56.20 | 6.60 | 13.11 |
| Found (%) | 56.19 | 6.57 | 13.31 |

EXAMPLE 114

To a mixture of 1.2 g of 6-(1-piperazinyl)-3,4-dihydrocarbostyril, 1.17 g of potassium carbonate and 20 ml of hexamethylphosphoric triamide was added 651 mg of 4-hydroxybenzyl chloride and the mixture was stirred at 90° C. for 2.5 hours. The reaction mixture was poured into a large amount of water and extracted with chloroform. After washing with water, the extract was dried over anhydrous sodium sulfate. Chloroform was distilled off and the residue was purified through silica gel column chromatography to give 0.3 g of 6-[4-(4-hydroxybenzyl)-1-piperazinyl]-3,4-dihydrocarbostyril.

Elemental Analysis for

|  | C | H | N |
|---|---|---|---|
| Calc'd (%) | 14.24 | 6.82 | 12.46 |
| Found (%) | 14.33 | 6.74 | 12.37 |

|  | C | H | N |
|---|---|---|---|
| Calc'd (%) | 69.04 | 6.30 | 11.51 |
| Found (%) | 68.89 | 6.43 | 11.42 |

EXAMPLE 115

To a mixture of 1.2 g of 6-(1-piperazinyl)-3,4-dihydrocarbostyril, 1.17 g of potassium bicarbonate and 20 ml of DMF was added 646 mg of 4-methylbenzyl chloride and the mixture was stirred at 80° C. for 2.5 hours. The reaction mixture was poured into a large amount of water and extracted with chloroform. After washing with water the extract was dried over anhydrous sodium sulfate. Chloroform was distilled off and the residue was purified through silica gel column chromatography. After conversion to hydrochloric acid salt with methanol-hydrochloric acid, the product was recrystallized from methanol-water to give 0.17 g of 6-[4-(4-methylbenzyl)-1-piperazinyl]-3,4-dihydrocarbostyril dihydrochloride, m.p. 272°–273° C. (decomp.), colorless powders.

Elemental Analysis for

|  | C | H | N |
|---|---|---|---|
| Calc'd (%) | 61.91 | 6.63 | 10.32 |
| Found (%) | 61.86 | 6.59 | 10.39 |

EXAMPLE 116

To a mixture of 1.2 g of 5-(1-piperazinyl)-3,4-dihydrocarbostyril, 1.17 g of potassium carbonate and 50 ml of benzene was added 688 mg of 4-cyanobenzyl chloride and the mixture was stirred under reflux for 3 hours. The reaction mixture was poured into a large amount of saturated saline solution and extracted with chloroform. After washing with water, the extract was dried over anhydrous sodium sulfate. Chloroform was distilled off and the residue was purified through silica gel column chromatography to give 105 mg of 5-[4-(4-cyanobenzyl)-1-piperazinyl]-3,4-dihydrocarbostyril.

Elemental Analysis for

|  | C | H | N |
|---|---|---|---|
| Calc'd (%) | 72.83 | 6.36 | 16.18 |
| Found (%) | 72.92 | 6.51 | 16.07 |

EXAMPLE 117

To a mixture of 1.2 g of 6-(1-piperazinyl)-3,4-dihydrocarbostyril, 1.17 g of potassium bicarbonate and 20 ml of DMF was added 785 mg of 3,4-methylenedioxybenzyl chloride and the mixture was stirred at 80°–90° C. for 3.5 hours. The reaction mixture was poured into a large amount of saturated saline solution and extracted with chloroform. After washing with water the extract was dried over anhydrous sodium sulfate. Chloroform was distilled off and the residue was purified through silica gel column chromatography to give 0.2 g of 6-[4-(3,4-methylenedioxybenzyl)-1-piperazinyl]-3,4-dihydrocarbostyril.

Elemental Analysis for

EXAMPLE 118

5-(1-Piperazinyl)-3,4-dihydrocarbostyril (1.0 g) was added to a mixture of 10 ml of DMF and 0.85 ml of trimethylamine and the mixture was stirred at room temperature while slowly adding dropwise 5 ml of DMF solution containing 1.07 g of p-toluenesulfonyl chloride. After completion of addition, the reaction mixture was stirred at the same temperature as above for 30 minutes. The reaction mixture was poured into a large amount of saturated saline solution and extracted with chloroform. The extract was washed with water and dried over anhydrous sodium sulfate. Chloroform was distilled off and residual crystals were recrystallized from DMF to give 800 mg of 5-[4-(p-toluenesulfonyl)-1-piperazinyl]-3,4-dihydrocarbostyril, m.p. 302°–304° C., colorless powders.

Elemental Analysis for

|  | C | H | N |
|---|---|---|---|
| Calc'd (%) | 62.34 | 5.97 | 10.91 |
| Found (%) | 62.43 | 5.89 | 10.79 |

EXAMPLE 119

6-(1-Piperazinyl)-3,4-dihydrocarbostyril (1.0 g) was added to a mixture of 10 ml of DMF and 0.85 ml of trimethylamine and the mixture was stirred at room temperature while slowly adding dropwise 5 ml of DMF solution containing 440 mg of methanesulfonyl chloride. After completion of addition, the reaction mixture was stirred at the same temperature as above for 30 minutes. The reaction mixture was poured into a large amount of water and extracted with chloroform. The extract was washed with water and dried over anhydrous sodium sulfate. Chloroform was distilled off and residual crystals were recrystallized from methanol to give 0.17 g of 6-(4-methanesulfonyl-1-piperazinyl)-3,4-dihydrocarbostyril, m.p. 241.5°–243° C., colorless granules.

Elemental Analysis for

|  | C | H | N |
|---|---|---|---|
| Calc'd (%) | 54.37 | 6.15 | 13.59 |
| Found (%) | 54.23 | 6.24 | 13.43 |

EXAMPLE 120

To a mixture of 1 g of 6-(1-piperazinyl)-3,4-dihydrocarbostyril, 30 ml of DMF and 900 mg of potassium carbonate was added 2 ml of butyl bromide and the mixture was stirred at 80° C. for 2.5 hours. The reaction mixture was poured into a large amount of saturated saline solution and extracted with chloroform. After washing with water, the extract was dried over anhydrous sodium sulfate. Then, chloroform was distilled off and the residue was purified through silica gel column chromatography. After conversion to hydrochloric acid salt with methanol-hydrochloric acid, the product was recrystallized from methanol to give 700 mg of 6-(4-butyl-1-piperazinyl)-3,4-dihydrocarbostyril hydrochloride hemihydrate, m.p. 279°–281° C. (decomp.).
Elemental Analysis for

|  | C | H | N |
|---|---|---|---|
| Calc'd (%) | 61.46 | 7.53 | 12.65 |
| Found (%) | 61.34 | 7.45 | 12.51 |

In an analogous manner as in Example 116, the same compound as those obtained in Examples 15 and 39 were prepared using appropriate starting materials.

EXAMPLE 121

To a mixture of 1 g of 5-(1-piperazinyl)-3,4-dihydrocarbostyril, 20 ml of DMSO and 1.7 g of potassium carbonate was added 450 mg of ethyl bromide and the mixture was stirred at 70°–100° C. for 4.5 hours. The reaction mixture was poured into a large amount of water and extracted with chloroform. After washing with water, the extract was dried over anhydrous sodium sulfate. Then, chloroform was distilled off and the residue was purified through silica gel column chromatography. After conversion to hydrochloric acid salt with methanol-hydrochloric acid, the product was recrystallized from methanol to give 0.14 g of 5-(4-ethyl-1-piperazinyl)-3,4-dihydrocarbostyril monohydrochloride, m.p. 293°–296° C. (decomp.), colorless granules.
Elemental Analysis for

|  | C | H | N |
|---|---|---|---|
| Calc'd (%) | 61.01 | 7.46 | 14.24 |
| Found (%) | 61.08 | 7.41 | 14.19 |

EXAMPLE 122

To a mixture of 1 g of 6-(1-piperazinyl)-3,4-dihydrocarbostyril, 15 ml of DMF and 1.82 g of potassium carbonate was added 500 mg of allyl bromide and the mixture was stirred at room temperature for 2 hours. The reaction mixture was poured into a large amount of water and extracted with chloroform. After washing with water, the extract was dried over anhydrous sodium sulfate. Then, chloroform was distilled off and the residue was purified through silica gel column chromatography and recrystallized from chloroform-ether to give 0.43 g of 6-(4-allyl-1-piperazinyl)-3,4-dihydrocarbostyril, m.p. 175°–176° C., colorless scales.
Elemental Analysis for

|  | C | H | N |
|---|---|---|---|
| Calc'd (%) | 70.84 | 7.75 | 15.50 |
| Found (%) | 70.73 | 7.81 | 15.38 |

EXAMPLE 123

To a mixture of 1 g of 5-(1-piperazinyl)-3,4-dihydrocarbostyril, 30 ml of DMF and 900 mg of sodium carbonate was added 491 mg of propargyl bromide and the mixture was stirred at 80° C. for 3 hours. The reaction mixture was poured into a large amount of saturated saline solution and extracted with chloroform. After washing with water, the extract was dried over anhydrous sodium sulfate. Then, chloroform was distilled off and the residue was purified through silica gel column chromatography and recrystallized from chloroform to give 0.1 g of 5-[4-(2-propynyl)-1-piperazinyl]-3,4-dihydrocarbostyril, m.p. 225°–226° C., pale yellow powders.
Elemental Analysis for

|  | C | H | N |
|---|---|---|---|
| Calc'd (%) | 71.38 | 7.06 | 15.61 |
| Found (%) | 71.23 | 7.14 | 15.48 |

EXAMPLE 124

To a mixture of 1 g of 6-(1-piperazinyl)-3,4-dihydrocarbostyril, 30 ml of DMF and 900 mg of sodium hydrogencarbonate was added 600 mg of 3-methylallylbromide and the mixture was stirred at 100° C. for 2.5 hours. The reaction mixture was poured into a large amount of saturated saline solution and extracted with chloroform. After washing with water, the extract was dried over anhydrous sodium sulfate. Then, chloroform was distilled off and the residue was purified through silica gel column chromatography. After conversion to hydrochloric acid salt with methanol-hydrochloric acid, the product was recrystallized from methanol to give 0.4 g of 6-[4-(2-butenyl)-1-piperazinyl]-3,4-dihydrocarbostyril dihydrochloride, m.p. 242°–245° C. (decomp.), colorless scales.
Elemental Analysis for

|  | C | H | N |
|---|---|---|---|
| Calc'd (%) | 56.98 | 7.03 | 11.73 |
| Found (%) | 56.92 | 6.72 | 11.77 |

EXAMPLE 125

6-[4-(3,4-Dimethoxybenzoyl)-1-piperazinyl]-3,4-dihydrocarbostyril (500 mg) and 70 mg of 60% oily sodium hydride were mixed with 5 ml of DMF and stirred at room temperature for 1 hour. Then, to the mixture was added dropwise 3 ml of DMF solution containing 0.17 ml of benzylchloride. After stirring for 4 hours at room temperature, the reaction mixture was poured into a large amount of water and organic substances were extracted with chloroform. The chloroform layer was washed with water and dehydrated. Chloroform was distilled off and the residue was recrystallized from ethanol to give 150 mg of 1-benzyl-6-[4-(3,4-dimethoxybenzoyl)-1-piperazinyl]-3,4-dihydrocarbostyril hemihydrate, m.p. 131.5°–132.5° C., yellow powders. Elemental Analysis for

|  | C | H | N |
|---|---|---|---|
| Calc'd (%) | 70.43 | 6.52 | 8.50 |
| Found (%) | 70.60 | 6.45 | 8.46 |

In an analogous manner as in Example 121, the same compound as that obtained in Example 35 was prepared using appropriate starting materials.

EXAMPLE 126

5-[4-(3,4-Dimethoxybenzoyl)-1-piperazinyl]-3,4-dihydrocarbostyril (1.96 g) and 0.20 g of sodium amide were mixed with 60 ml of DMF and stirred at room temperature for 2 hours. Then, to the mixture was added 0.67 g of allyl chloride and the mixture was stirred at room temperature for 10 hours. The reaction mixture was poured into 150 ml of saturated saline solution and organic substances were extracted with chloroform. The chloroform layer was washed with water and dehydrated. Chloroform was distilled off and the residue was purified through silica gel column chromatography followed by recrystallization from methanol-ether to give 1.76 g of 1-allyl-5-[4-(3,4-dimethoxybenzoyl)-1-piperazinyl]-3,4-dihydrocarbostyril hemihydrate, m.p. 120°-122° C., colorless granules.

Elemental Analysis for

|  | C | H | N |
|---|---|---|---|
| Calc'd (%) | 67.57 | 6.53 | 9.46 |
| Found (%) | 67.49 | 6.59 | 9.38 |

EXAMPLE 127

6-[4-(3,4-Dimethoxybenzoyl)-1-piperazinyl]-3,4-dihydrocarbostyril (1.96 g) and 0.25 g of 50% oily sodium hydride were mixed with 60 ml of DMF and stirred at room temperature for 2 hours. Then, to the mixture was added 0.66 g of propargyl chloride and the mixture was stirred at room temperature for 7 hours. The reaction mixture was poured into a 150 ml of saturated saline solution and organic substances were extracted with chloroform. The chloroform layer was washed with water and dehydrated. Chloroform was distilled off and the residue was purified through silica gel column chromatography followed by recrystallization from ethanol to give 0.34 g of 1-(2-propynyl)-6-[4-(3,4-dimethoxybenzoyl)-1-piperazinyl]-3,4-dihydrocarbostyril, m.p. 152°-154° C., pale yellow needles.

Elemental Analysis for

|  | C | H | N |
|---|---|---|---|
| Calc'd (%) | 69.27 | 6.28 | 9.69 |
| Found (%) | 69.36 | 6.39 | 9.57 |

EXAMPLE 128

(a) To a solution of 9.36 g of 6-amino-3,4-dihydrocarbostyril in 70 ml of methanol was added 13.5 g of di-β-bromoethyl ether and stirred under reflux for 10 hours. After cooling, to the reaction mixture was added 3.06 g of potassium carbonate and stirred under reflux for 10 hours. After cooling, crystals which formed were collected by filtration. The crystals thus-obtained were dissolved in 40 ml of water and the solution was rendered weakly alkaline with a dilute aqueous sodium hydroxide solution. The mother liquor was distilled off and to the residue was added isopropanol to precipitate crystals which then were collected by filtration to give 4.7 g of 6-(4-morpholino)-3,4-dihydrocarbostyril. Production of this compound was confirmed by IR and NMR spectra.

Elemental Analysis for

|  | C | H | N |
|---|---|---|---|
| Calc'd (%): | 67.24 | 6.90 | 12.07 |
| Found (%): | 67.12 | 7.02 | 11.98 |

(b) A mixture of 2.32 g of 6-morpholino-3,4-dihydrocarbostyril and 14.7 g of 4-methoxybenzylamine was placed in a sealed tube and heated at 170° to 200° C. for 5 hours. Excessive 4-methoxybenzylamine was distilled off under reduced pressure and the residue was isolated and purified through silica gel column chromatography followed by recrystallization from ethanol to give 0.35 g of 6-[4-(4-methoxybenzyl)-1-piperazinyl]-3,4-dihydrocarbostyril, m.p. 196°-198° C., colorless needles.

Elemental Analysis for

|  | C | H | N |
|---|---|---|---|
| Calc'd (%): | 71.79 | 7.12 | 11.97 |
| Found (%): | 71.65 | 6.98 | 12.10 |

In an analogous manner as in Example 128, the same compounds as those obtained in Examples 1, 2, 6, 15, 28-31, 39 and 42-49 described above and those obtained in Examples 143, 145, 147 and 148 described hereinafter were prepared using appropriate starting materials.

EXAMPLE 129

A mixture of 14.5 g of 6-[bis(2-chloroethyl)amino]-3,4-dihydrocarbostyril, 8.0 g of 4-methoxybenzylamine and 70 ml of methanol was stirred under reflux for 15 hours. After cooling, to the reaction mixture was added 3.06 g of sodium carbonate and the reaction mixture was stirred under reflux for 8 hours. After cooling, crystals which precipitated were collected by filtration and recrystallized from ethanol to give 8.1 g of 6-[4-(4-methoxybenzyl)-1-piperazinyl]-3,4-dihydrocarbostyril, m.p. 196°-198° C., colorless needles.

Elemental Analysis for

|  | C | H | N |
|---|---|---|---|
| Calc'd (%): | 71.79 | 7.12 | 11.97 |
| Found (%): | 71.62 | 7.21 | 11.82 |

In an analogous manner as in Example 129, the same compounds as those obtained in Examples 1, 2, 6, 15, 28-31, 39 and 42-49 described above and those obtained in Examples 143, 145, 147 and 148 described hereinafter were prepared using appropriate starting materials.

EXAMPLE 130

(a) A mixture of 81 g of 6-amino-3,4-dihydrocarbostyril and 82 g of ethylene chlorohydrin was stirred at about 160° C. for 10 hours. After allowing to cool, the reaction mixture was added 100 ml of aqueous 10 N NaOH solution to separate organic layer which then was dried over KOH. After removing KOH by filtration, the liquor was distilled off under reduced pressure to give 90 g of 6-[bis(2-hydroxyethyl)amino]-3,4-dihydrocarbostyril. Production of the compound was confirmed by IR and NMR spectra.

Elemental Analysis for

|  | C | H | N |
|---|---|---|---|
| Calc'd (%): | 62.40 | 7.20 | 11.20 |
| Found (%): | 62.27 | 7.09 | 11.34 |

(b) A mixture of 9 g of 6-[bis(2-hydroxyethyl)amino]-3,4-dihydrocarbostyril, 4.1 g of 4-methoxybenzylamine and 7.6 g of polyphosphoric acid prepared from 3.8 g of phosphorus pentoxide and 3.8 g of phosphoric acid was reacted at 160° to 170° C. for about 6 hours. After allowing to cool, to the reaction mixture was added dropwise about 500 ml of water to dissolve. The solution was neutralized with an aqueous 48% sodium hydroxide solution and extracted with chloroform. After drying the extract over potassium carbonate, chloroform was distilled off. Recrystallization of the residue from ethanol gave 8 g of 6-[4-(4-methoxybenzyl)-1-piperazinyl]-3,4-dihydrocarbostyril, m.p. 196°-198° C., colorless needles.

Elemental Analysis for

|  | C | H | N |
|---|---|---|---|
| Calc'd (%): | 71.79 | 7.12 | 11.97 |
| Found (%): | 71.91 | 7.01 | 11.86 |

In an analogous manner as in Example 130, the same compound as those obtained in Examples 1, 2, 6, 15, 28–31, 39 and 42–49 described above and those obtained in Examples 143, 145, 147 and 148 described hereinafter were prepared using appropriate starting materials.

EXAMPLE 131

A mixture of 2.7 g of 6-amino-3,4-dihydrocarbostyril, 5.9 g of N,N-bis(2-hydroxyethyl)-3,4-dimethoxybenzamide and 8.6 g of 85% phosphoric acid was reacted at 165° to 175° C. for 4.5 hours while stirring. After allowing to cool, to the reaction mixture was added dropwise about 50 ml of water to dissolve. The solution was neutralized with an aqueous 48% sodium hydroxide solution and extracted with chloroform. After drying the extract over potassium carbonate, chloroform was distilled off. Recrystallization of the residue from ethanol-chloroform gave 4.7 g of 6-[4-(3,4-dimethoxybenzoyl)-1-piperazinyl]-3,4-dihydrocarbostyril, m.p. 238°-239.5° C., colorless granules.

Elemental Analysis for

|  | C | H | N |
|---|---|---|---|
| Calc'd (%): | 66.84 | 6.33 | 10.63 |
| Found (%): | 66.95 | 6.23 | 10.51 |

In an analogous manner as in Example 131, the same compound as those obtained in Examples 1, 2 and 4–91 described above and those obtained in Examples 143, 145, 147 and 148 described hereinafter were prepared using appropriate starting materials.

EXAMPLE 132

(a) A solution of 7.02 g of p-aminoaniline in 150 ml of toluene was added 9.12 ml of triethylamine and stirred at 80° C. while adding dropwise a solution of 11 g of β-bromopropionyl chloride in 30 ml of toluene. After the mixture was reacted for 30 minutes colored resinous substance which formed was removed, and the reaction mixture was washed with water and dried. Removal of the solvent by distillation gave 10.1 g of N-(β-bromopropionyl)-p-aminoaniline as oily product. Production of the compound was confirmed by IR and NMR spectra.

Elemental Analysis for

|  | C | H | N |
|---|---|---|---|
| Calc'd (%): | 44.44 | 4.53 | 11.52 |
| Found (%): | 44.32 | 4.61 | 11.43 |

(b) A mixture of 14.0 g of N-(β-bromopropionyl)-p-aminoaniline, 18 g of bis(β-bromoethyl)amine monohydrobromide and 70 ml of methanol was stirred under reflux for 15 hours. After cooling, the reaction mixture was added 3.06 g of potassium carbonate and stirred under reflux for 8 hours. After cooling, crystals which formed were collected by filtration and washed with methanol to give 5.3 g of N-(β-bromopropionyl)-p-piperazinylaniline. Production of the compound was confirmed by IR and NMR spectra.

Elemental Analysis for

|  | C | H | N |
|---|---|---|---|
| Calc'd (%): | 50.00 | 5.77 | 13.46 |
| Found (%): | 49.91 | 5.69 | 13.41 |

(c) A suspension of 2.2 g of N-(β-bromopropionyl)-p-piperazinylaniline and 28 g of pulverized anhydrous aluminum chloride in 50 ml of carbon disulfide was stirred under reflux for 4 hours. The reaction mixture was poured into ice water and the precipitations were collected by filtration, washed with water and then with ether and converted to hydrobromic acid salt followed by recrystallization from methanol-water to give 0.9 g of 6-(1-piperazinyl)-3,4-dihydrocarbostyril monohydrobromide, m.p. 289°-293° C. (decomp.) (methanol-water), colorless needles.

Elemental Analysis for

|  | C | H | N |
|---|---|---|---|
| Calc'd (%): | 50.00 | 5.77 | 13.46 |
| Found (%): | 49.96 | 5.81 | 13.51 |

In an analogous manner as in Example 132, the same compound as those obtained in Examples 2–92 described above and those obtained in Examples 143, 145, 147 and 148 described hereinafter were prepared using appropriate starting materials.

EXAMPLE 133

A mixture of 2.6 g of 3,4-dimethoxybenzoic acid, 1.65 g of 1,8-diazabicyclo[5,4,0]undecene-7 and 100 ml of DMF was stirred with ice-cooling externally while adding dropwise 1.5 ml of isobutyl chloroformate. After completion of addition, the mixture was stirred for 30 minutes and a solution of 2.3 g of 6-(1-piperazinyl)-3,4-dihydrocarbostyril in 40 ml of DMF was added thereto. After stirring at room temperature for 5 hours, the solvent was distilled off and the residue was extracted with about 300 ml of chloroform. The extract was washed sequentially with a dilute aqueous $NaHCO_3$ solution, water, dilute hydrochloric acid and water. Chloroform was distilled off and the residue was recrystallized from ethanol-chloroform to give 1.7 g of 6-[4-(3,4-dimethoxybenzoyl-1-piperazinyl]-3,4-dihydrocarbostyril, m.p. 238°-239.5° C., colorless granules.

Elemental Analysis for

|  | C | H | N |
|---|---|---|---|
| Calc'd (%): | 66.84 | 6.33 | 10.63 |
| Found (%): | 66.72 | 6.45 | 10.52 |

In an analogous manner as in Example 133, the same compound as those obtained in Examples 4, 7–14, 16–26, 32–38, 41, 50–61 and 63–91 were prepared using appropriate starting materials.

EXAMPLE 134

A mixture of 1.22 ml of acetic anhydride and 0.5 ml of formic acid was stirred at 50°–60° C. for 2 hours. After cooling to room temperature, 1.0 g of 5-piperazinyl-3,4-dihydrocarbostyril was added portionwise to the reaction mixture, during which operation the product was solidified. To the solids was added 5 ml of dichloromethane and the mixture was stirred at room temperature for 2 hours. Then, a large amount of water was added thereto and the mixture was extracted with chloroform. After washing with water, the extract was dried over anhydrous sodium sulfate followed by removal of chloroform by distillation. Recrystallization of the residue from methanol gave 420 mg of 5-(4-formyl-1-piperazinyl)-3,4-dihydrocarbostyril, m.p. 263°–265° C., colorless granules.

Elemental Analysis for

|            | C     | H    | N     |
|------------|-------|------|-------|
| Calc'd (%): | 64.84 | 6.61 | 16.21 |
| Found (%):  | 64.64 | 6.57 | 16.22 |

In an analogous manner as in Example 134, the same compound as that obtained in Example 62 was prepared using appropriate starting material.

EXAMPLE 135

Ethyl 2-nitro-5-piperazinylcinnamate hydrochloride (3.5 g) was dissolved in a mixed solvent consisting of 150 ml of ethanol and 45 ml of water and the solution was adjusted to pH of about 7 with an aqueous sodium hydroxide. The solution was added 2 g of Raney nickel catalyst and placed in a glass autoclave followed by stirring at 80° C. under hydrogen gas pressure of 5 kg/cm$^2$ for 4 hours. After removing hydrogen gas the reaction mixture was taken out and the catalyst was removed. The solution was concentrated to dryness and methanol was added to the residue to precipitate crystals, which then were collected by filtration and recrystallized from methanol to give 1.3 g of 6-(1-piperazinyl)-3,4-dihydrocarbostyril, m.p. 224°–231.5° C.

EXAMPLE 136

2-Nitro-5-[4-(3,4-dimethoxybenzoyl)-1-piperazinyl]-cynnamic acid (8.8 g) was dissolved in 88 ml of DMF and to the solution was added 1.6 g of Raney nickel catalyst and the mixture was reacted at 80° C. for 4 hours under hydrogen gas pressure of 3 kg/cm$^2$ using Parr's apparatus. After removing hydrogen gas the reaction mixture was taken out and the catalyst was removed. The solution was concentrated to dryness and methanol was added to the residue to precipitate crystals, which then were collected by filtration and recrystallized from DMF and then from chloroform-methanol to give 5.8 g of 6-[4-(3,4-dimethoxybenzoyl)-1-piperazinyl]-3,4-dihydrocarbostyril, m.p. 238°–239.5° C.

In an analogous manner as in Example 136, the same compounds as those obtained in Examples 2, 4–49, 64–66, 73–87, 90 and 91 were prepared using appropriate starting materials.

EXAMPLE 137

A suspension of 1.0 g of 6-(1-piperazinyl)-3,4-dihydrocarbostyril monohydrobromide in 10 ml of DMF was added 296 mg of sodium hydrogencarbonate and stirred at room temperature for 30 minutes to convert the compound to 6-piperazinyl-3,4-dihydrocarbostyril, to which was added 0.62 ml of triethylamine. Then, a solution of 605 mg of 4-acetyloxybenzoyl chloride in 5 ml of DMF was slowly added dropwise to the mixture. After completion of addition, the mixture was stirred at room temperature for 1 hour. The reaction mixture was poured into a large amount of water and extracted with chloroform. The extract was washed serially with saturated aqueous sodium hydrogencarbonate solution and with water and then dried over anhydrous sodium sulfate. Chloroform was distilled off to give 6-[4-(4-acetyloxybenzoyl)-1-piperazinyl]-3,4-dihydrocarbostyril.

Elemental Analysis for

|            | C     | H    | N     |
|------------|-------|------|-------|
| Calc'd (%): | 67.16 | 5.89 | 10.68 |
| Found (%):  | 67.04 | 5.98 | 10.49 |

EXAMPLE 138

(a) A solution of 11 g of p-[4-(3,4-dimethoxybenzoyl)-1-piperazinyl]aniline in 100 ml of benzene was added 4.56 ml of triethylamine and refluxed while adding dropwise a solution of 3.94 g of β-methoxyacryloyl chloride in 20 ml of benzene. After completion of addition, the mixture was refluxed for 1 hour. After completion of reaction, the reaction mixture was washed with water and dried. The solvent was distilled off and the residue was purified through silica gel column chromatography to give 10 g of N-(β-methoxyacryloyl)-p-[4-(3,4-dimethoxybenzoyl)-1-piperazinyl]aniline.

Elemental Analysis

|            | C     | H    | N    |
|------------|-------|------|------|
| Calc'd (%): | 64.92 | 6.40 | 9.88 |
| Found (%):  | 64.77 | 6.51 | 9.75 |

(b) N-(β-methoxyacryloyl)-p-[4-(3,4-dimethoxybenzoyl)-1-piperazinyl]aniline (5 g) was added portionwise to 50 ml of 60% H$_2$SO$_4$ while stirring at room temperature. After continuing the reaction for 2 hours, the reaction mixture was neutralized with 10 N NaOH to precipitate crystals which then were collected by filtration and washed with water. Recrystallization of the crystals from chloroform-methanol gave 230 mg of 6-[4-(3,4-dimethoxybenzoyl)-1-piperazinyl]carbostyril, m.p. 265°–266.5° C. (decomp.), yellow granules.

Elemental Analysis

|            | C     | H    | N     |
|------------|-------|------|-------|
| Calc'd (%): | 67.16 | 5.89 | 10.68 |
| Found (%):  | 67.03 | 5.78 | 10.81 |

In an analogous manner as in Example 138, the same compounds as those obtained in Examples 50–53, 55–63, 67–72, 88 and 89 were prepared using appropriate starting materials.

EXAMPLE 139

A mixture of 5.6 g of 6-bromo-3,4-dihydrocarbostyril, 2.9 g of 4-(3,4-dimethoxybenzoyl)-1-piperazine, 1.8 g of potassium carbonate, 0.2 g of copper powders and 60 ml of 3-methoxybutanol was refluxed for 5 hours. The reaction mixture was filtered and the filtrate was concentrated to dryness under reduced pressure. The residue was extracted with methanol-chloroform and then chloroform layer was distilled off. The residue thus obtained was purified through preparative silica gel thin layer chromatography and recrystallized from chloroform-ethanol to give 489 mg of 6-[4-(3,4-dimethoxybenzoyl)-1-piperazinyl]-3,4-dihydrocarbostyril, m.p. 238°-239.5° C., colorless granules.

Elemental Analysis for $C_{22}H_{25}N_3O_4$

|  | C | H | N |
|---|---|---|---|
| Calc'd (%): | 66.84 | 6.33 | 10.63 |
| Found (%): | 66.70 | 6.48 | 10.53 |

In an analogous manner as in Example 139, the same compounds as those obtained in Examples 1, 2, and 4–91 described above and those obtained in Examples 143, 145, 147 and 148 described hereinafter were prepared using appropriate starting materials.

EXAMPLE 140

3-{2-Amino-5-[4-(3,4-dimethoxybenzoyl)-1-piperazinyl]phenyl}propionic acid (1 g) was dissolved in a mixed solvent consisting of chloroform and methanol, and 1 ml of concentrated hydrochloric acid was added to the solution. The resulting mixture was stirred for 1 hour at room temperature. After distilling off the solvent, the residue was recrystallized from ethanol-chloroform to give 500 mg of 6-[4-(3,4-dimethoxybenzoyl)-1-piperazinyl]-3,4-dihydrocarbostyril, m.p. 238°-239.5° C., colorless granules.

In an analogous manner as in Example 140, the same compounds as those obtained in Examples 1, 2, 4–49, 64–66 and 73–87 described above and those obtained in Examples 143, 145, 147 and 148 described hereinafter were prepared using appropriate starting materials.

EXAMPLE 141

3-{2-Aminoacetyl-5-[4-(3,4-dimethoxybenzoyl)-1-piperazinyl]phenyl}propionic acid (10 g) was dissolved in diphenyl ether (100 ml) and the solution was stirred at 90°-100° C. After continuing the reaction for 8 hours, the reaction mixture was poured into water and crystals which precipitated were collected by filtration. The crystals thus obtained were subjected to silica gel column chromatography to separate and then recrystallized from methanol-chloroform to give 1.2 g of 6-[4-(3,4-dimethoxybenzoyl)-1-piperazinyl]carbostyril, m.p. 265°-266.5° C. (decomp.), yellow granules.

In an analogous manner as in Example 141, the same compounds as those obtained in Examples 50–53, 55–63 and 67–72 described above and those obtained in Examples 143 and 148 were prepared using appropriate starting materials.

EXAMPLE 142

2-Amino-5-[4-(3,4-dimethoxybenzoyl)-1-piperazinyl]cinnamic acid (5 g) was dissolved in DMF (50 ml), and 5% palladium-carbon (0.5 g) was added to the solution. The mixture was reacted at 80° C. for 4 hours using Parr's apparatus at a hydrogen gas pressure of 3 kg/cm². After removing hydrogen gas, the content was taken out. After removing the catalyst, the reaction mixture was concentrated to half the original volume and poured into a large volume of water. Crystals which precipitated were collected by filtration and recrystallized from ethanol-chloroform to give 2.9 g of 6-[4-(3,4-dimethoxybenzoyl)-1-piperazinyl]-3,4-dihydrocarbostyril, m.p. 238°-239.5° C., colorless granules.

In an analogous manner as in Example 142, the same compounds as those obtained in Examples 1, 2, 4–49, 64–66, 73–87 described above and those obtained in Examples 145, and 147 described hereinafter were prepared using appropriate starting materials.

EXAMPLE 143

A mixture of 25 g of 6-aminocarbostyril, 50 g of bis(β-bromoethyl)amine hydrobromide and DMF was stirred at 80°-90° C. for 3 hours. After cooling to room temperature, 8.2 g of $Na_2CO_3$ was added to the mixture and stirred at 80°-90° C. for 4 hours. After cooling to room temperature, crystals which precipitated were collected by filtration, washed with ethanol and dried to give 22 g of 6-(1-piperazinyl)carbostyril hydrobromide, m.p. above 300° C., pale yellow rhombic crystals (water-ethanol).

EXAMPLE 144

6-(1-Piperazinyl)carbostyril hydrobromide (2.0 g) was suspended in 20 ml of DMF. After adding 2.34 ml of triethylamine, a solution of 1.43 g of 3,4-methylenedioxybenzoyl chloride in 2 ml of DMF was added dropwise to the mixture. After completion of addition, the mixture was stirred at room temperature for 30 minutes and the reaction mixture was poured in a large amount of water. Crystals which formed were collected by filtration and dried. Then, the crystals were purified through silica gel column chromatography and recrystallized from chloroform-methanol to give 1.9 g of 6-[4-(3,4-methylenedioxybenzoyl)-1-piperazinyl]carbostyril, m.p. 266°-267° C. (decomp.), yellow powders.

EXAMPLE 145

A mixture of 23 g of 7-amino-3,4-dihydrocarbostyril, 48 g of bis(β-bromoethyl)amine hydrobromide and 200 ml of methanol was refluxed with stirring for 8 hours. After cooling to room temperature, 7.52 g of sodium carbonate was added to the mixture followed by refluxing while stirring for additional 8 hours. After distilling off methanol under reduced pressure, isopropanol was added to the residue. After cooling, crystals which precipitated were collected by filtration and recrystallized from ethanol 3 times to give 15 g of 7-(1-piperazinyl)-3,4-dihydrocarbostyril hydrobromide, m.p. 174°-177° C., colorless granules.

EXAMPLE 146

To a solution of 800 mg of 7-(1-piperazinyl)-3,4-dihydrocarbostyril hydrobromide in 10 ml of DMF was added 1.2 ml of triethylamine, and then a solution of 730 mg of 4-chlorobenzoyl chloride in 2 ml of DMF was added dropwise to the mixture while stirring. After completion of addition, the mixture was stirred at room temperature for 30 minutes. The reaction mixture was poured into a large amount of water. Crystals which formed were collected by filtration, washed with water and dried. The crystals were purified through silica gel column chromatography and recrystallized from chloroform-methanol to give 700 mg of 7-[4-(4-chlorobenzoyl)-1-piperazinyl]-3,4-dihydrocarbostyril, m.p. 289°-291° C., colorless powders.

EXAMPLE 147

8-Amino-3,4-dihydrocarbostyril (7.5 g, 46.2 mmols) and bis(β-bromoethyl)amine hydrobromide (15.9 g, 50.8 mmols) were suspended in methanol and the suspension was heated under reflux while stirring for 9 hours. After adding 2.5 g of sodium carbonate, the reaction mixture was further heated under reflux for 8 hours while stirring, and stirred on an ice bath for 1 hours. Crystals which precipitated were collected by filtration. The crude crystals thus obtained were recrystallized from methanol-ether to give 2.4 g of 8-(1-piperazinyl)-3,4-dihydrocarbostyril hydrobromide, m.p. above 300° C., colorless needles.

EXAMPLE 148

8-Aminocarbostyril (15.47 g, 96.6 mmols) and bis(β-bromoethyl)amine hydrobromide (33 g, 106 mmols) were suspended in DMF and the suspension was stirred at 70° to 80° C. for 10 hours. After adding 5.1 g of sodium carbonate the reaction mixture was stirred at the same temperature as above for 7 hours. After distilling off the solvent under reduced pressure, methanol was added to the residue to crystallize. The crude crystals thus obtained were recrystallized from methanol-ether to give 5.1 g of 8-(1-piperazinyl)carbostyril hydrobromide, m.p. above 300° C., colorless scales.

EXAMPLE 149

8-(1-Piperazinyl)carbostyril (0.7 g, 2.26 mmols) and sodium hydrogencarbonate (0.2 g) were suspended in 5 ml of DMF and the suspension was stirred at room temperature for 30 minutes. To the resulting mixture was added 0.4 ml of triethylamine, and further a solution of 0.47 g of 2-chlorobenzoyl chloride in 5 ml of DMF dropwise, followed by stirring at room temperature for 30 minutes. The reaction mixture was poured in saturated aqueous sodium hydrogencarbonate and extracted with chloroform. The organic layer was washed with water and then with saturated aqueous sodium hydrogencarbonate and dried over sodium sulfate. After distilling off the solvent, ether was added to the residue to crystallize. The crystals thus obtained were recrystallized from ethanol to give 0.24 g of 8-[4-(2-chlorobenzoyl)-1-piperazinyl]carbostyril, m.p. 239°-240.5° C., colorless needles.

Pharmacological Tests

Pharmacological activity of the compounds of this invention was determined as described below.

I. Isolated Blood-Perfused Sinoatrial Node Preparations

Experiments were carried out on adult mongrel dogs of either sex. The sinoatrial node preparations were obtained from dogs weighing 8013 kg, anesthetized with pentobarbital sodium (30 mg/kg i.v.), given heparin sodium (1000 U/kg i.v.) and exsanguinated. The preparation consisted essentially of the right atrium and was set up in cold Tyrode's solution. The preparation was placed in a glass water jacket maintained at about 38° C. and cross-circulated through the cannulated right coronary artery with blood from a donor dog at a constant pressure of 100 mmHg. Dogs used as donors were 18-27 kg in body weight and were anesthetized with pentobarbital sodium (30 mg/kg i.v.). Heparin sodium was given at a dose of 1000 U/kg i.v. Tension developed by the right atrium was measured with a strain-gauge transducer. The right atrium was loaded with a weight of about 1.5 g. Sinus rate was measured by a cardiotachometer triggered by developed tension of the right atrium. Blood flow through the right coronary artery was measured by an electromagnetic flow meter. Recording of developed tension, sinus rate and blood flow was made on charts with an ink-writing rectigraph. Details of the preparation have been described by Chiba et al. (Japan. J. Pharmacol. 25, 433-439, 1975; Naunyn-Schmiedberg's Arch. Pharmacol. 289, 315-325, 1975). The compounds of 10-30 μl were injected intra-arterially in 4 sec. The inotropic effects of the compounds are expressed as a percentage of the developed tension before the injection of the compounds. The effects of the compounds on sinus rate (beats/min.) or blood flow (ml/min.) are expressed as a difference between the values before and after the injection of the compounds. The results obtained are shown in Table 1 below.

Test Compounds 1. 6-[4-(3,4-Dimethoxybenzoyl)-1-piperazinyl]-3,4-dihydrocarbostyril
2. 6-[4-(4-Methoxybenzoyl)-1-piperazinyl]-3,4-dihydrocarbostyril
3. 6-(4-Acetyl-1-piperazinyl)-3,4-dihydrocarbostyril
4. 6-[4-(4-Methoxybenzyl)-1-piperazinyl]-3,4-dihydrocarbostyril
5. 6-[4-(3,4,5-Trimethoxybenzoyl)-1-piperazinyl]-3,4-dihydrocarbostyril
6. 5-[4-(3,4,5-Trimethoxybenzoyl)-1-piperazinyl]-3,4-dihydrocarbostyril
7. 6-[4-(4-Chlorobenzyl)-1-piperazinyl]-3,4-dihydrocarbostyril
8. 6-(1-Piperazinyl)-3,4-dihydrocarbostyril
9. 6-[4-(4-Nitrobenzoyl)-1-piperazinyl]-3,4-dihydrocarbostyril
10. 6-[4-(4-Aminobenzoyl)-1-piperazinyl]-3,4-dihydrocarbostyril
11. 6-[4-(3,4-Methylenedioxybenzoyl)-1-piperazinyl]-3,4-dihydrocarbostyril
12. 6-[4-(4-Bromobenzoyl)-1-piperazinyl]-3,4-dihydrocarbostyril
13. 6-[4-(4-Cyanobenzoyl)-1-piperazinyl]-3,4-dihydrocarbostyril
14. 5-[4-(3,4-Dimethoxybenzoyl)-1-piperazinyl]-3,4-dihydrocarbostyril
15. 8-Methoxy-6-[4-(3,4-dimethoxybenzoyl)-1-piperazinyl]-3,4-dihydrocarbostyril
16. 1-Methyl-6-[4-(3,4-dimethoxybenzoyl)-1-piperazinyl]-3,4-dihydrocarbostyril
17. 6-(4-Furoyl-1-piperazinyl)-3,4-dihydrocarbostyril
18. 6-(4-Benzoyl-1-piperazinyl)-3,4-dihydrocarbostyril
19. 1-Benzyl-6-[4-(3,4-dimethoxybenzoyl)-1-piperazinyl]-3,4-dihydrocarbostyril hemihydrate
20. 6-[4-(2-Phenethyl)-1-piperazinyl]-3,4-dihydrocarbostyril monohydrochloride
21. 6-(Formyl-1-piperazinyl)-3,4-dihydrocarbostyril
22. 6-(4-Ethoxycarbonylmethyl-1-piperazinyl)-3,4-dihydrocarbostyril
23. 6-(4-Ethoxycarbonyl-1-piperazinyl)-3,4-dihydrocarbostyril
24. 6-[4-(3-Chlorobenzoyl)-1-piperazinyl]-3,4-dihydrocarbostyril
25. 6-(4-Methanesulfonyl-1-piperazinyl)-3,4-dihydrocarbostyril
26. 6-[4-(4-Methylbenzyl)-1-piperazinyl]-3,4-dihydrocarbostyril 27. 5-[4-(3,4-dichlorobenzoyl)-1-piperazinyl]-3,4-dihydrocarbostyril monohydrochloride monohydrate
28. 6-[4-(3,5-Dinitrobenzoyl)-1-piperazinyl]-3,4-dihydrocarbostyril
29. 6-(4-Allyl-1-piperazinyl)-3,4-dihydrocarbostyril
30. 5-[4-(2-Propynyl)-1-piperazinyl]-3,4-dihydrocarbostyril
31. 5-(4-Ethyl-1-piperazinyl)-3,4-dihydrocarbostyril monohydrochloride
32. 1-Allyl-5-[4-(3,4-dimethoxybenzoyl)-1-piperazinyl]-3,4-dihydrocarbostyril hemihydrate
33. 1-(2-Propynyl)-6-[4-(3,4-dimethoxybenzoyl)-1-piperazinyl]-3,4-dihydrocarbostyril
34. 5-[4-(p-Toluenesulfonyl)-1-piperazinyl]-3,4-dihydrocarbostyril
35. 6-[4-(4-Methylthiobenzoyl)-1-piperazinyl]carbostyril
36. 6-[4-(3-Pyridylcarbonyl)-1-piperazinyl]-3,4-dihydrocarbostyril
37. 6-[4-(4-Methoxyphenylacetyl)-1-piperazinyl]-3,4-dihydrocarbostyril hemihydrate
38. 6-(4-Phenylpropionyl-1-piperazinyl)-3,4-dihydrocarbostyril
39. 8-[4-(3,4-Dimethoxybenzoyl)-1-piperazinyl]carbostyril
40. 5-[4-(4-Hydroxybenzoyl)-1-piperazinyl]-3,4-dihydrocarbostyril
41. 6-[4-(3,4-Dimethoxybenzoyl)-1-piperazinyl]carbostyril
42. 6-[4-(3-Chlorobenzoyl)-1-piperazinyl]carbostyril
43. 6-[4-(3,4-Methylenedioxybenzoyl)-1-piperazinyl]carbostyril
44. 6-[4-(4-Nitrobenzoyl)-1-piperazinyl]carbostyril
45. 6-[4-(4-Cyanobenzoyl)-1-piperazinyl]carbostyril
46. 6-(4-Benzoyl-1-piperazinyl)carbostyril
47. 6-[4-(4-Chlorobenzoyl)-1-piperazinyl]carbostyril
48. 6-[4-(3,4-Trimethoxybenzoyl)-1-piperazinyl]carbostyril
49. 6-(4-Ethoxycarbonyl-1-piperazinyl)carbostyril
50. 6-[4-(4-Aminobenzoyl)-1-piperazinyl]carbostyril
51. 6-[4-(4-Formyl)-1-piperazinyl]carbostyril
52. 5-(4-Benzyl-1-piperazinyl)-3,4-dihydrocarbostyril monohydrochloride
53. 7-[4-(3,4-Methylenedioxybenzoyl)-1-piperazinyl]-3,4-dihydrocarbostyril
54. 7-[4-(3,4,5-Trimethoxybenzoyl)-1-piperazinyl]-3,4-dihydrocarbostyril
55. 7-[4-(2-Chlorobenzoyl)-1-piperazinyl]-3,4-dihydrocarbostyril
56. 7-(4-Phenylpropionyl-1-piperazinyl)-3,4-dihydrocarbostyril
57. 7-[4-(3,4-Dimethoxybenzoyl)-1-piperazinyl]-3,4-dihydrocarbostyril
58. Papaverin (Comparison)
59. Amrinone (Comparison)

TABLE 1

| Test Compound | Dose | % Change in Contraction of Atrial Muscle | Change in Rate of Coronary Blood Flow (ml/min) |
|---|---|---|---|
| | (n mole) | | |
| 1 | 100 | 79.6 | 1.2 |
| 2 | 100 | 100 | 0.8 |
| 3 | 300 | 96 | 0.8 |
| 4 | 100 | 25 | — |
| 5 | 300 | 83 | 1.6 |
| 6 | 300 | 35.7 | 0.8 |
| 7 | 100 | 8.0 | — |
| 8 | 100 | 5.7 | 0.4 |

TABLE 1-continued

| Test Compound | Dose | % Change in Contraction of Atrial Muscle | Change in Rate of Coronary Blood Flow (ml/min) |
|---|---|---|---|
| 9 | 100 | 60 | 1.0 |
| 10 | 300 | 50.0 | 1.2 |
| 11 | 100 | 46.9 | 1.6 |
| 12 | 300 | 33 | 1.6 |
| 13 | 300 | 63.2 | 0.6 |
| 14 | 300 | 65.9 | 1.0 |
| 15 | 1000 | 25 | 1.2 |
| 16 | 300 | 10.7 | 2.0 |
| 17 | 100 | 53.8 | 1.2 |
| 18 | 300 | 40 | 1.6 |
| | (n mole/l) | | |
| 19 | 300 | 17.9 | 2.0 |
| 20 | 500 | 18.5 | 0.8 |
| 21 | 100 | 122.2 | 0.4 |
| 22 | 1000 | 15.3 | 0.4 |
| 23 | 100 | 25.0 | 0.4 |
| 24 | 100 | 57.1 | 0.2 |
| 25 | 100 | 24.1 | 0.3 |
| 26 | 100 | 19.0 | 0.2 |
| 27 | 300 | 20.0 | 0.2 |
| 28 | 300 | 14.3 | 1.4 |
| 29 | 100 | 20.3 | 0.2 |
| 30 | 100 | 21.4 | 0.3 |
| 31 | 100 | 20.7 | 0.2 |
| 32 | 300 | 13 | 1.2 |
| 33 | 300 | 12 | 0.8 |
| 34 | 300 | 42 | 1.1 |
| 41 | 300 | 145 | 1.4 |
| 52 | 300 | 37.8 | — |
| 58 | 100 | 73.8 | 2.4 |

II. Isolated Blood-Perfused Papillary Muscle Preparations

Experiments were carried out on adult mongrel dogs of either sex. The papillary muscle preparations were obtained from dogs weighing 8–13 kg, anesthetized with pentobarbital sodium (30 mg/kg i.v.), given heparin sodium (1000 U/kg i.v.) and exsanguinated. The preparation was essentially the anterior papillary muscle excised together with the ventricular septum and was set up in cold Tyrode's solution. The preparation was placed in a glass water jacket maintained at about 38° C. and cross-circulated through the cannulated anterior septal artery with blood from a donor dog at a constant pressure of 100 mmHg. Dogs used as donors were 18–27 kg in body weight and were anesthetized with pentobarbital sodium (30 mg/kg i.v.). Heparin sodium was given at a dose of 1000 U/kg i.v. The papillary muscle was driven with rectangular pulse about 1.5 times the threshold voltage (0.5–3 V) and 5 msec duration at a fixed rate of 120 beats/min. through bipolar pacing electrodes. Tension developed by the papillary muscle was measured with a strain-gauge transducer. The muscle was loaded with a weight of about 1.5 g. Blood flow through the anterior septal artery was measured by an electromagnetic flow meter. Recording of developed tension and blood flow was made on charts with an ink-writing rectigraph. Details of the preparation have ben described by Endoh and Hashimoto (*Am. H. Physiol.* 218, 1459–1463, 1970). The compounds in volumes of 10–30 μl were injected intra-arterially in 4 sec. The inotropic effects of the compounds are expressed as a percentage of the developed tension before the injection of the compounds. The effects of the compounds on blood flow are expressed as a difference (ml/min.) between the values before and after the injection of the compounds. The results obtained are shown in Table 2 below.

TABLE 2

| Test Compound | Dose (n mole/l) | % Change in Contraction of Papillary Muscle | Change in Rate of Coronary Blood Flow (ml/min.) |
|---|---|---|---|
| 29 | 1000 | 12.6 | 1 |
| 30 | 1000 | 11.5 | 0.5 |
| 31 | 1000 | 15 | 2 |
| 35 | 100 | 17.4 | 0.5 |
| 36 | 1000 | 44.4 | 1.5 |
| 37 | 1000 | 18.4 | — |
| 38 | 300 | 60.7 | 1 |
| 39 | 1000 | 27.7 | 2 |
| 40 | 1000 | 17.6 | — |
| 42 | 300 | 56.0 | 2.5 |
| 43 | 300 | 75.0 | 1 |
| 44 | 300 | 32.3 | 3 |
| 45 | 300 | 45.5 | 1 |
| 46 | 200 | 30.0 | 1.5 |
| 47 | 1000 | 28.0 | 4 |
| 48 | 1000 | 38.3 | — |
| 49 | 300 | 56.7 | 3.5 |
| 50 | 100 | 15.8 | 0.5 |
| 51 | 100 | 73.3 | 1 |
| 53 | 1000 | 13.2 | 3.5 |
| 54 | 1000 | 11.5 | 4 |
| 55 | 1000 | 17.4 | 3.5 |
| 56 | 1000 | 14 | 3 |
| 57 | 1000 | 14.2 | 3.5 |
| 59 | 1000 | 30.8 | — |

PREPARATION EXAMPLE 1

6-[4-(3,4-Dimethoxybenzoyl)-1-piperazinyl]-3,4-dihydrocarbostyril—5 mg
Starch—132 mg
Magnesium Stearate—18 mg
Lactose—45 mg Tablets each having the above composition were prepared in a conventional manner.

PREPARATION EXAMPLE 2

6-[4-(4-Methoxybenzoyl)-1-piperazinyl]-3,4-dihydrocarbostyril—10 mg
Starch—127 mg
Magnesium Stearate—18 mg
Lactose—45 mg Tablets each having the above composition were prepared in a conventional manner.

PREPARATION EXAMPLE 3

6-[4-(4-Nitrobenzoyl)-1-piperazinyl]-3,4-dihydrocarbostyril—500 mg
Polyethylene Glycol (molecular weight: 4,000)—0.3 g
Sodium Chloride—0.9 g
Polyoxyethylene Sorbitan Monooleate—0.4 g
Sodium Metabisulfite—0.1 g
Methylparaben—0.18 g
Propylparaben—0.02 g
Distilled water for injection—100 ml The above parabens, sodium metabisulfite and sodium chloride were dissolved in the distilled water at 80° C. while stirring. The resulting solution was cooled to 40° C. and polyethylene glycol and polyoxyethylene sorbitan monooleate were dissolved therein. Then, distilled water for injection was added to adjust the volume to final one. The mixture was filtered using a suitable filter paper to sterilize and then filled in an ampoule of 1 ml, thus forming preparation for injection.

PREPARATION EXAMPLE 4

6-[4-(3,4-Dimethoxybenzoyl)-1-piperazinyl]carbostyril—5 mg
Starch—132 mg
Magnesium Stearate—18 mg
Lactose—45 mg Tablets each having the above composition were prepared in a conventional manner.

While the invention has been described in detail and with reference to specific embodiments thereof, it will be apparent to one skilled in the art that various changes and modifications can be made therein without departing from the spirit and scope thereof.

What is claimed is:

1. A carbostyril compound of the formula (I)

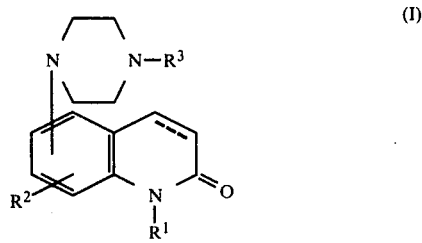

wherein
$R^1$ represents a hydrogen atom, a lower alkyl group, a lower alkenyl group, a lower alkynyl group, or a phenyl-lower alkyl group;
$R^2$ represents a hydrogen atom or a lower alkoxy group;
$R^3$ represents a hydrogen atom, a lower alkanoyl group, a furoyl group, a pyridylcarbonyl group, a lower alkanesulfonyl group, a lower alkoxycarbonyl group, a lower alkoxycarbonyl-lower alkyl group, a phenylsulfonyl group which may be substituted with a lower alkyl group on the benzene ring thereof, a lower alkyl group, a lower alkenyl group, a lower alkynyl group, a phenylcarbonyl group, a phenyl-lower alkyl group, or a phenyl-lower alkanoyl group where each of said phenylcarbonyl group, phenyl-lower alkyl group and phenyl-lower alkanoyl group may be substituted with 1 to 3 of a lower alkoxy group, a halogen atom, a lower alkyl group, a cyano group, a nitro group, an amino group, a hydroxy group, a lower alkanoylamino group, a lower alkylthio group and a lower alkanoyloxy group, or with a lower alkylenedioxy group on the benzene ring thereof; and
the bonding between the 3- and 4-positions of the carbostyril nucleus is a single bond or a double bond;

or its pharmaceutically acceptable salt.

2. A carbostyril compound or its pharmaceutically acceptable salt as claimed in claim 1, wherein $R^3$ represents a phenylcarbonyl group which may be substituted with 1 to 3 of a lower alkoxy group, a halogen atom, a lower alkyl group, a cyano group, a nitro group, an amino group, a hydroxy group, a lower alkanoylamino group, a lower alkylthio group and a lower alkanoyloxy group or with a lower alkylenedioxy group on the benzene ring thereof.

3. A carbostyril compound or its pharmaceutically acceptable salt as claimed in claim 1, wherein $R^3$ represents a lower alkanoyl group, a furoyl group, a pyridylcarbonyl group, a lower alkoxycarbonyl group, or a phenyl-lower alkanoyl group which may be substituted with 1 to 3 of a lower alkoxy group, a halogen atom, a lower alkyl group, a cyano group, a nitro group, an amino group, a hydroxy group, a lower alkanoylamino group, a lower alkylthio group and a lower alkanoyloxy group or with a lower alkylenedioxy group on the benzene ring thereof.

4. A carbostyril compound or its pharmaceutically acceptable salt as claimed in claim 1, wherein $R^3$ represents a lower alkanesulfonyl group, or a phenylsulfonyl group which may be substituted with a lower alkyl group on the benzene ring thereof.

5. A carbostyril compound or its pharmaceutically acceptable salt as claimed in claim 1, wherein $R^3$ represents a hydrogen atom, a lower alkoxycarbonyl-lower alkyl group, a lower alkyl group, a lower alkenyl group, a lower alkynyl group, or a phenyl-lower alkyl group which may be substituted with 1 to 3 of a lower alkoxy group, a halogen atom, a lower alkyl group, a cyano group, a nitro group, an amino group, a hydroxy group, a lower alkanoylamino group, a lower alkylthio group and a lower alkanoyloxy group or with a lower alkylenedioxy group on the benzene ring thereof.

6. A carbostyril compound or its pharmaceutically acceptable salt as claimed in claim 2, wherein $R^1$ and $R^2$ each represents a hydrogen atom.

7. A carbostyril compound or its pharmaceutically acceptable salt as claimed in claim 2, wherein $R^1$ and $R^2$ each is other than a hydrogen atom.

8. A carbostyril compound or its pharmaceutically acceptable salt as claimed in claim 3, wherein $R^1$ and $R^2$ each represents a hydrogen atom.

9. A carbostyril compound or its pharmaceutically acceptable salt as claimed in claim 3, wherein $R^1$ and $R^2$ each is other than a hydrogen atom.

10. A carbostyril compound or its pharmaceutically acceptable salt as claimed in claim 6, wherein the bonding between the 3- and 4-positions of the carbostyril nucleus is a single bond.

11. A carbostyril compound or its pharmaceutically acceptable salt as claimed in claim 6, wherein the bonding between the 3- and 4-positions of the carbostyril nucleus is a double bond.

12. A carbostyril compound or its pharmaceutically acceptable salt as claimed in claim 10 or 11, wherein the substituent of the formula

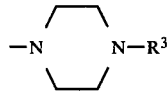

is on the 5- or 6-position of the carbostyril nucleus.

13. A carbostyril compound or its pharmaceutically acceptable salt as claimed in claim 10 or 11, wherein the substituent of the formula

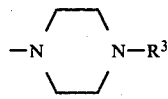

is on the 7- or 8-position of the carbostyril nucleus.

14. A carbostyril compound or its pharmaceutically acceptable salt as claimed in claim 12, wherein $R^3$ represents a benzoyl group which is substituted with 1 to 3 of a lower alkoxy group and a halogen atom, or with a lower alkylenedioxy group on the benzene ring thereof.

15. 6-[4-(3,4-Dimethoxybenzoyl)-1-piperazinyl]-3,4-dihydrocarbostyril according to claim 14.

16. 5-[4-(3,4-Dimethoxybenzoyl)-1-piperazinyl]-3,4-dihydrocarbostyril according to claim 14.

17. 6-[4-(4-Methoxybenzoyl)-1-piperazinyl]-3,4-dihydrocarbostyril according to claim 14.

18. 6-[4-(4-Aminobenzoyl)-1-piperazinyl]-3,4-dihydrocarbostyril according to claim 12.

19. 6-[4-(3,4-Methylenedioxybenzoyl)-1-piperazinyl]-3,4-dihydrocarbostyril according to claim 14.

20. 5-(4-Formyl-1-piperazinyl)-3,4-dihydrocarbostyril according to claim 8.

21. 6-[4-(4-Chlorobenzoyl)-1-piperazinyl]-3,4-dihydrocarbostyril according to claim 14.

22. 6-[4-(3-Chlorobenzoyl)-1-piperazinyl]-3,4-dihydrocarbostyril according to claim 14.

23. 6-[4-(3,4-Dimethoxybenzoyl)-1-piperazinyl]-carbostyril according to claim 12.

24. 6-[4-(3,4-Methylenedioxybenzoyl)-1-piperazinyl]-carbostyril according to claim 12.

25. 6-[4-(3-Chlorobenzoyl)-1-piperazinyl]-carbostyril according to claim 12.

26. 6-[4-(4-Chlorobenzoyl)-1-piperazinyl]-carbostyril according to claim 12.

27. A cardiotonic composition comprising a cardiotonically effective amount of a compound of the formula (I)

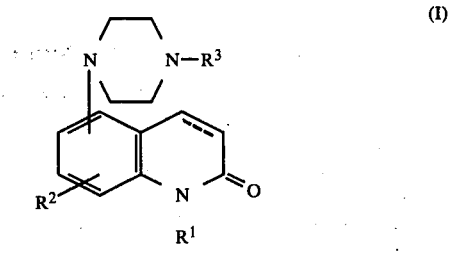

wherein
$R^1$ represents a hydrogen atom, a lower alkyl group, a lower alkenyl group, a lower alkynyl group, or a phenyl-lower alkyl group;
$R^2$ represents a hydrogen atom or a lower alkoxy group;
$R^3$ represents a hydrogen atom, a lower alkanoyl group, a furoyl group, a pyridylcarbonyl group, a lower alkanesulfonyl group, a lower alkoxycarbonyl group, a lower alkoxycarbonyl-lower alkyl group, a phenylsulfonyl group which may be substituted with a lower alkyl group on the benzene ring thereof, a lower alkyl group, a lower alkenyl group, a lower alkynyl group, a phenylcarbonyl group, a phenyl-lower alkyl group, or a phenyl-lower alkanoyl group where each of said phenylcarbonyl group, phenyl-lower alkyl group and phenyl-lower alkanoyl group may be substituted with 1 to 3 of a lower alkoxy group, a halogen atom, a lower alkyl group, a cyano group, a nitro group, an amino group, a hydroxy group, a lower alkanoylamino group, a lower alkylthio group and a lower alkanoyloxy group, or with a lower alkylenedioxy group on the benzene ring thereof; and the bonding between the 3- and 4-positions of the carbostyril nucleus is a single bond or a double bond;
or its pharmaceutically acceptable salt, and a pharmaceutically acceptable carrier.

* * * * *